US012661532B2

(12) United States Patent
Karakuz

(10) Patent No.: US 12,661,532 B2
(45) Date of Patent: Jun. 23, 2026

(54) DEVICE AND METHOD FOR ULTRASOUND TREATMENT OF BIOLOGICAL TISSUE

(71) Applicant: BESHAPE TECHNOLOGIES LTD., Kfar-Saba (IL)

(72) Inventor: Vitaly Karakuz, Kfar-Saba (IL)

(73) Assignee: BESHAPE TECHNOLOGIES LTD., Kfar-Saba (IL)

( * ) Notice: Subject to any disclaimer, the term of this patent is extended or adjusted under 35 U.S.C. 154(b) by 145 days.

(21) Appl. No.: 18/568,785

(22) PCT Filed: Jul. 14, 2022

(86) PCT No.: PCT/IL2022/050761
§ 371 (c)(1),
(2) Date: Dec. 8, 2023

(87) PCT Pub. No.: WO2023/286064
PCT Pub. Date: Jan. 19, 2023

(65) Prior Publication Data
US 2024/0299777 A1 Sep. 12, 2024

Related U.S. Application Data

(60) Provisional application No. 63/222,485, filed on Jul. 16, 2021, provisional application No. 63/222,505,
(Continued)

(51) Int. Cl.
*A61N 7/02* (2006.01)
*A61N 7/00* (2006.01)

(52) U.S. Cl.
CPC ........ *A61N 7/02* (2013.01); *A61N 2007/0008* (2013.01); *A61N 2007/0073* (2013.01); *A61N 2007/0078* (2013.01)

(58) Field of Classification Search
CPC ...... A61F 2007/0052; A61F 2007/0056; A61F 2007/0075; A61F 7/00; A61N 2007/0008;
(Continued)

(56) References Cited

U.S. PATENT DOCUMENTS

| | | |
|---|---|---|
| 2010/0274161 A1 | 10/2010 | Azhari et al. |
| 2012/0277587 A1 | 11/2012 | Adanny et al. |

FOREIGN PATENT DOCUMENTS

| | | |
|---|---|---|
| WO | 2009/013729 A2 | 1/2009 |

OTHER PUBLICATIONS

J. C. Bamber, et al., "Ultrasonic attenuation and propagation speed in mammalian tissues as a function of temperature," Ultrasound in Med. & Biol., vol. 5, pp. 149-157 (1979).

*Primary Examiner* — Mark D Remaly
(74) *Attorney, Agent, or Firm* — Maschoff Brennan

(57) ABSTRACT

A medical device is presented for applying heat-based tissue treatment to an individual's body part. The medical device includes an applicator carrying a transducer arrangement controllably operable to perform a treatment session on at least one region of interest in tissue to achieve a desired treatment effect. The applicator is configured to define a substantially U-shaped surface presenting a U-shaped interface region for attachment with the body part such that the region(s) of interest is/are located between opposite arms of said U-shaped interface region, thereby enabling attachment of tissue being treated in a cavity defined by the U-shaped interface region. The transducer arrangement performs a treatment session on region(s) of interest by delivering heating radiation towards each region, and comprises first and second opposing ultrasound transducer-assemblies defining, respectively, first and second opposing ultrasound-transceiving surfaces located at the opposite arms of the U-shaped interface region.

23 Claims, 35 Drawing Sheets

102

6 Piezo-Element (6PE) Example
Applicator Housing 420
103C
320CA    320CB
424C    424C    424C
424A
320AA
First pair 322A of opposing piezo elements
424B
320BA
320AB
Second pair 322B of opposing piezo elements
320BB
103A    424A
424B    103B

Related U.S. Application Data filed on Jul. 16, 2021, provisional application No. 63/222,500, filed on Jul. 16, 2021.

(58) Field of Classification Search
CPC .... A61N 2007/0034; A61N 2007/0073; A61N 2007/0078; A61N 2007/027; A61N 7/00; A61N 7/02
See application file for complete search history.

Figure 3E:
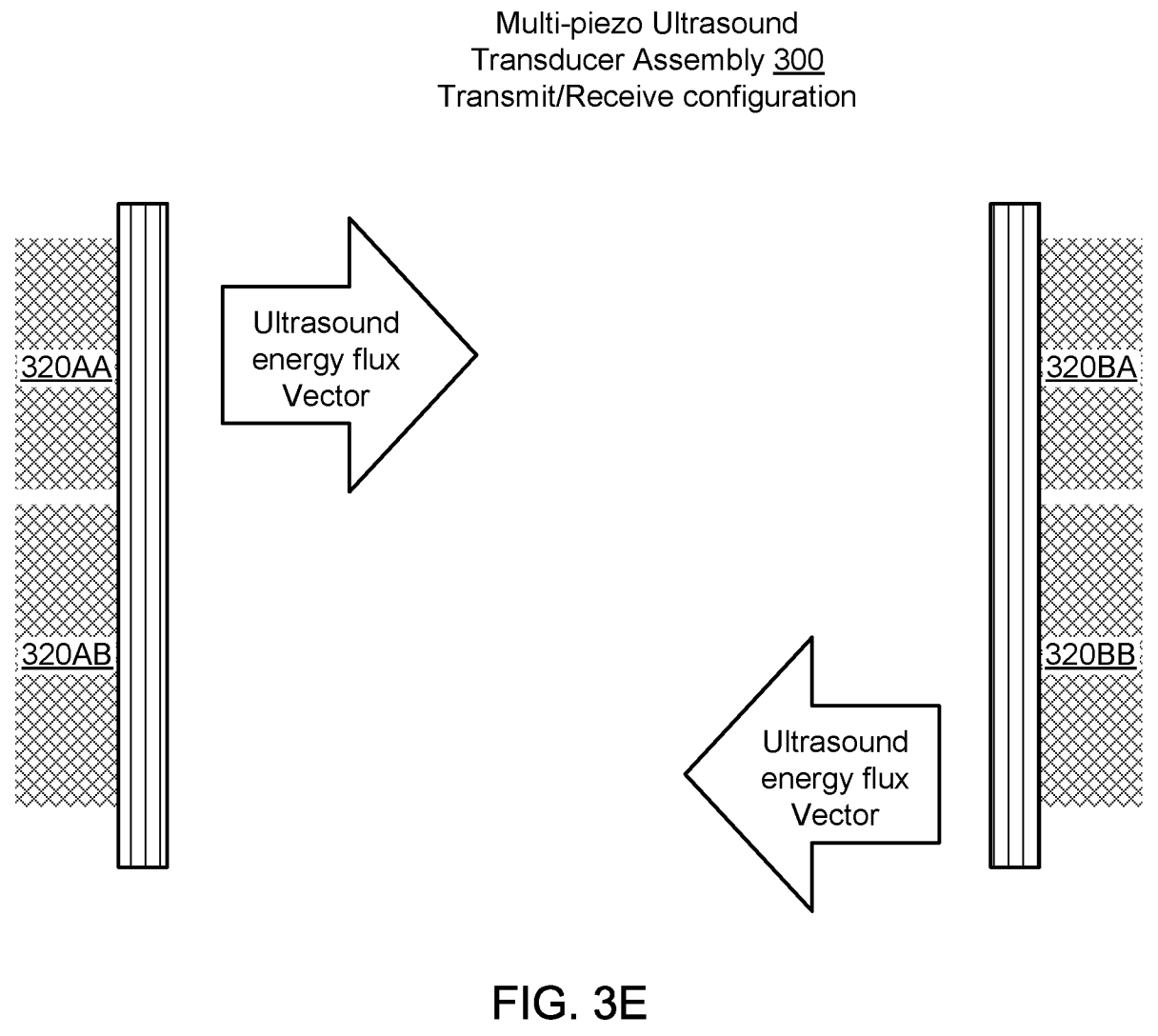

Multi-piezo Ultrasound
Transducer Assembly 300
Transmit/Receive configuration

320BA

320BB

Ultrasound
energy flux
Vector

Ultrasound
energy flux
Vector

Figure 6A:
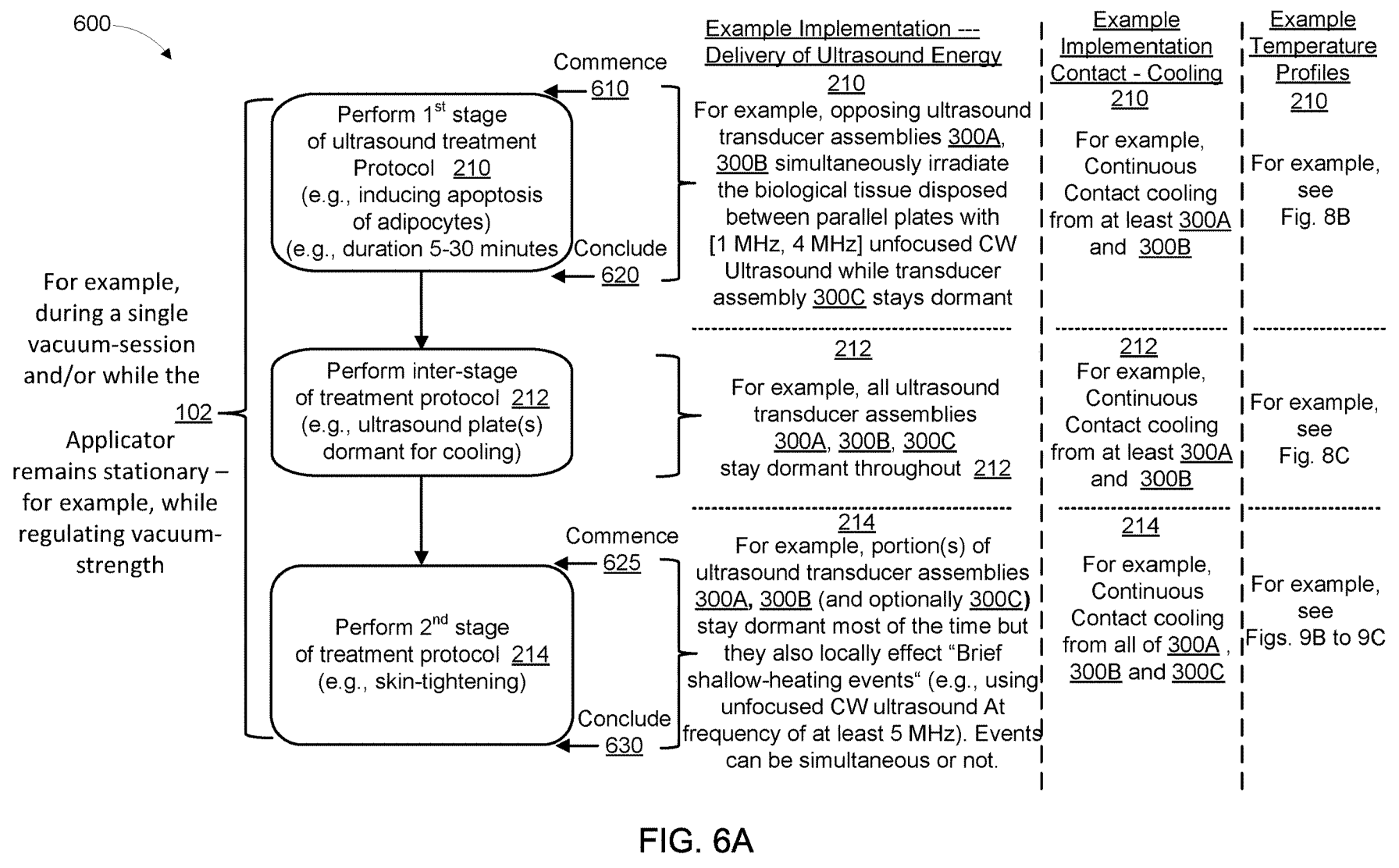

| Example Implementation — Delivery of Ultrasound Energy | Example Implementation Contact - Cooling 210 | Example Temperature Profiles 210 |
|---|---|---|
| 210 For example, opposing ultrasound transducer assemblies 300A, 300B simultaneously irradiate the biological tissue disposed between parallel plates with [1 MHz, 4 MHz] unfocused CW Ultrasound while transducer assembly 300C stays dormant | For example, Continuous Contact cooling from at least 300A and 300B | For example, see Fig. 8B |
| 212 For example, all ultrasound transducer assemblies 300A, 300B, 300C stay dormant throughout 212 | 212 For example, Continuous Contact cooling from at least 300A and 300B | For example, see Fig. 8C |
| 214 For example, portion(s) of ultrasound transducer assemblies 300A, 300B (and optionally 300C) stay dormant most of the time but they also locally effect "Brief shallow-heating events" (e.g., using unfocused CW ultrasound At frequency of at least 5 MHz). Events can be simultaneous or not. | 214 For example, Continuous Contact cooling from all of 300A, 300B and 300C | For example, see Figs. 9B to 9C |

Commence 610

Conclude 620

Perform 1st stage of ultrasound treatment Protocol 210 (e.g., inducing apoptosis of adipocytes) (e.g., duration 5-30 minutes)

Perform inter-stage of treatment protocol 212 (e.g., ultrasound plate(s) dormant for cooling)

Commence 625

Conclude 630

Perform 2nd stage of treatment protocol 214 (e.g., skin-tightening)

102

For example, during a single vacuum-session and/or while the Applicator remains stationary – for example, while regulating vacuum-strength

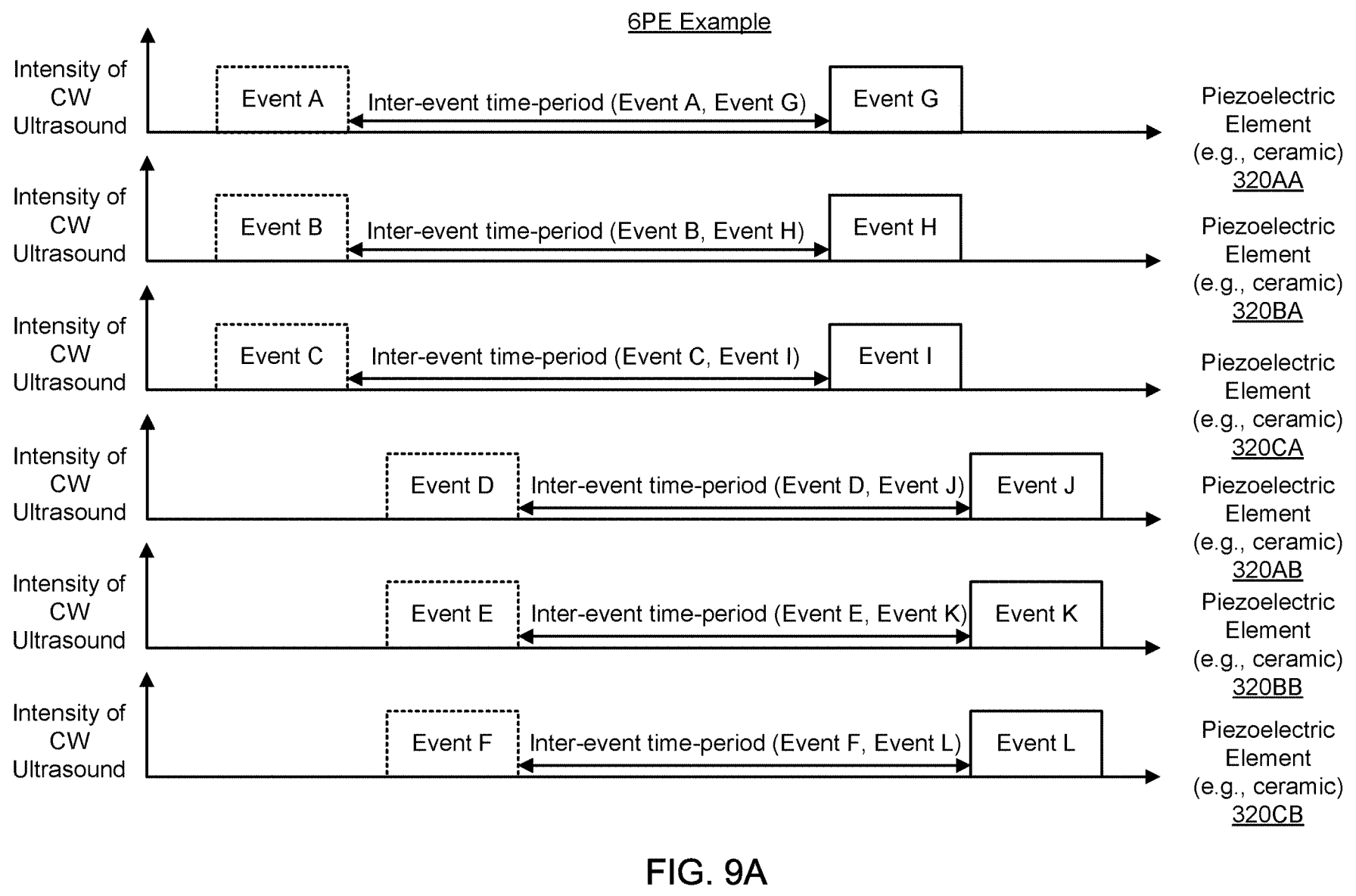

6PE Example

Piezoelectric Element (e.g., ceramic) 320AA

Piezoelectric Element (e.g., ceramic) 320BA

Piezoelectric Element (e.g., ceramic) 320CA

Piezoelectric Element (e.g., ceramic) 320AB

Piezoelectric Element (e.g., ceramic) 320BB

Piezoelectric Element (e.g., ceramic) 320CB

Event G

Event H

Event I

Event J

Event K

Event L

Inter-event time-period (Event A, Event G)

Inter-event time-period (Event B, Event H)

Inter-event time-period (Event C, Event I)

Inter-event time-period (Event D, Event J)

Inter-event time-period (Event E, Event K)

Inter-event time-period (Event F, Event L)

Event A

Event B

Event C

Event D

Event E

Event F

Intensity of CW Ultrasound

Intensity of CW Ultrasound

Intensity of CW Ultrasound

Intensity of CW Ultrasound

Intensity of CW Ultrasound

Intensity of CW Ultrasound

FIG. 9A

DEVICE AND METHOD FOR ULTRASOUND TREATMENT OF BIOLOGICAL TISSUE

TECHNOLOGICAL FIELD

The present disclosure relates to devices and methods for ultrasound treatment of biological tissue.

BACKGROUND

Ultrasound based treatment of biological tissues is generally known for various purposes such as fat reduction, skin tightening, wrinkles elimination, etc. Ultrasound based treatment is a non-invasive technique and is thus generally advantageous over various other techniques invasive or partially invasive treatments.

Ultrasound based fat reduction procedures are widely used in aesthetic medicine as they offer patients the chance for significant reductions in targeted fat deposits while circumventing the risks and side effects of invasive surgical procedures. The main goal of such noninvasive contouring devices is to improve body's appearance by removing the excess adipose tissue, particularly in areas in which fat persists despite optimal diet and exercise routine.

In addition, ultrasound based devices are targeting the deep dermis, subdermal connective tissue, and fibromuscular layers in precise zones without damage to the epidermis, causing gradual skin tightening through collagen contraction and remodeling.

Ultrasound energy based techniques are generally of two types utilizing focused and nonfocused devices depending on how the energy is delivered to the tissues. High-Intensity Focused Ultrasound (HIFU) is an example of focused ultrasound that has already been shown as an effective and safe treatment in body contouring. With HIFU, either relatively low-intensity ($17.5$ W/cm$^2$) or high-intensity ($1000$ W/cm$^2$) focused ultrasound is targeted at the focal zone, causing mechanical cellular membrane disruption or coagulative necrosis of the target tissue, respectively. However, it is often difficult to control high-energy focused ultrasound to satisfy constraints that may be required to perform various procedures for which it is intended.

In contrast, nonfocused low-intensity ultrasound at the intensity level of $0.125$-$7$ W/cm$^2$ is typically used in physiotherapy for thermal treatment. It is not indicated for body contouring because it is generally believed that nonfocused low-intensity ultrasound does not have as significant or as durable of an effect when compared to the HIFU. In practice, however, it is widely used for noninvasive body sculpting on the assumption that its ultrasonic thermal effect may contribute to the reduction of adipose tissue while its lower intensity poses less of a health risk compared to HIFU.

GENERAL DESCRIPTION

There is yet a need in the art to provide safe and efficient noninvasive techniques to apply treatment of deep and/or shallow body tissues to effect body shaping and skin tightening.

It should be emphasized that in order to achieve the desired tissue effect by applying heating radiation to the deep tissue region, in particular effect of lipolysis of fat cells in deeper skin layers, treatments may require higher densities of energy to be directed into the tissue, raising thus the temperature of shallower skin layers closer to skin surface, presenting a serious safety issue.

The present invention provides a novel approach for treatment of biological tissues by heating radiation which enables real time automatic patient-specific treatment, while concurrently performing temperature monitoring (almost continuously). This provides for automatically adjusting parameters of the treatment radiation for each and every individual during the treatment session, thus resulting in controlled, safe, and uniform tissue heating by said radiation along the region of interest.

Thus, according to one broad aspect of the invention, it provides a medical device for applying heat-based tissue treatment to an individual's body part. The device comprises an applicator carrying a transducer arrangement configured and controllably operable to perform a treatment session on at least one region of interest in tissue to achieve a desired treatment effect at each of said at least one region of interest. The applicator is configured to define a substantially U-shaped interface region for attachment with the body part along said interface region such that each of the at least one region of interest is located between opposite arms of said U-shaped interface region, thereby enabling attachment of tissue being treated in a cavity defined by said U-shaped interface region with proper acoustic contact. The transducer arrangement is configured and controllably operable to perform a treatment session on each of said at least one region of interest by delivering heating radiation towards each of said at least one region of interest, and comprises first and second opposing ultrasound transducer-assemblies defining, respectively, first and second opposing ultrasound-transceiving surfaces located at the opposite arms of the U-shaped interface region, said first and second ultrasound transducer-assemblies being configured to transmit ultrasound radiation from one of said ultrasound-transceiving surfaces and detect said ultrasound radiation at the other opposing ultrasound-transceiving surface and generate measured data corresponding to the detected ultrasound radiation which is indicative of at least one of temperature of the region of interest and attachment of the tissue to the interface region.

Preferably, the first and second opposing ultrasound transducer-assemblies are configured and operable to generate said heating radiation, and are configured to generate directional first and second ultrasound heating radiations propagating in opposite directions along substantially coinciding first and second axes towards each of the at least one region of interest in the tissue being engaged between said opposite arms of the interface region.

The applicator also includes a cooling assembly configured and controllably operable to perform cooling of the interface region.

In some embodiments, the applicator is configured such that its surface comprising said interface region is substantially flexible and foldable such that it is adapted to define said substantially U-shaped interface region.

In some other embodiments, a surface of the applicator comprising the U-shaped interface region is substantially rigid.

In some embodiments, the measured data is indicative of time-of-flight data of ultrasound pulse between the first and second transducer assemblies and thereby corresponds to time-of-flight of ultrasound radiation through the tissue engaged between the opposite arms of said interface region. This enables real time extraction, from the time-of-flight data, data indicative of an average temperature of the region of interest being a deep region with respect to the interface region.

To this end, the device may be configured and operable to utilize calibration data indicative of tissue temperature as a function of a change in the time-of-flight of the ultrasound radiation of a given frequency passing through a given biological tissue. Also, in some embodiments, the device may be configured and operable to utilize calibration data indicative of acoustic contact of the tissue surface and the interface region as a function of the time-of-flight of the ultrasound radiation of a given frequency passing through a given biological tissue, to evaluate, from the measured time-of-flight data, data indicative of the acoustic contact.

The medical device may further include a control unit configured and operable to control operation of the applicator to maintain predetermined temperature pattern in the tissue during the treatment session.

The device (e.g. its control unit) may include a temperature control circuitry for monitoring temperature of said at least one region of interest and/or an attachment (acoustic contact) control circuitry configured and operable to monitor acoustic contact between the tissue surface (skim) and at least a part of said interface region and control operation of the transducer arrangement accordingly. The temperature control circuitry may be configured to be responsive to the measured data indicative of the detected ultrasound radiation from the tissue to extract from this measured data at least one of an average temperature of the region of interest at respective location in the tissue. The attachment (acoustic contact) control circuitry may be responsive to said measured data to control operation of the transducer arrangement accordingly.

In some embodiments, the temperature control circuitry may be responsive to measured data indicative of an operative electric current of the cooling assembly required to cool the interface region to provide a predetermined temperature of tissue surface at the interface region to apply, based on this measured data, model-based processing utilizing thermal properties of a biological tissue under treatment and determine an average temperature of said tissue.

In some embodiments, the applicator further comprises at least one temperature sensor located in vicinity of the interface region and configured and operable to provide sensing data indicative of temperature of surface tissue regions.

Preferably, the first and second transducer assemblies are configured and controllably operated to generate the first and second ultrasound radiations of respectively first and second frequencies with a difference between them in a range of 0.5%-20%. The first and second frequencies are selected to avoid creation of a standing wave effect and provide substantially homogeneous temperature along the region of interest during the treatment session.

In some embodiments, the first and second opposing transducer assemblies comprise, respectively, first and second arrays of independently operable transceiver elements. The ultrasound-transceiving surface of each of said first and second transducer assemblies is thus defined by respective one of the first and second arrays of spaced-apart surface segments associated with the first and second arrays of the transceiver elements, By this, at least two opposing pairs of the ultrasound transceiver elements are defined, each pair being formed by the first and second transceiver elements generating the first and second directional ultrasound radiations propagating along substantially coinciding axes in the opposite directions towards the region of interest in the tissue being engaged between said opposing sides of the interface region.

Such transducer arrangement may be configured and controllably operable to substantially concurrently perform treatment sessions on at least two regions of interest being deep and shallow tissue regions with respect to their locations from the interface region.

In some embodiments, the transducer arrangement is configured and controllably operable with a time pattern of alternating tissue treatment intervals of the treatment session and intervals of the control session. For example, the tissue treatment intervals of the treatment session and intervals of the control session are implemented by, respectively, two different pairs of the opposing transceiver elements.

The control session may comprise temperature control of the region of interest being treated based on the detection of the ultrasound radiation passed through the region of interest, enabling real time adjustment of one or more operational parameters of the treatment session.

Also, the control session may comprise control of acoustic contact between the interface region and the tissue surface engaged by said interface region, enabling real time adjustment of the treatment session.

In some embodiments, the transducer arrangement is controllably operated with the continuous wave operational mode during said intervals of the treatment session and controllably operated with the pulsed mode during the intervals of the control session.

The operational frequency of the ultrasound radiation during the treatment session may be in a range of 1 MHz-4 Hz. The region of interest being treated may be a deep region with respect to the interface region.

In some embodiments, the transducer arrangement comprises an additional transducer assembly accommodated to transmit ultrasound radiation through a base portion of the U-shaped interface region.

The transducer arrangement may be configured and operable with a pulsed mode during the control session.

The region of interest may be a shallow region with respect to the interface region. The operational frequency of the ultrasound radiation during the treatment session may be in a range of 4.5 MHz.

The applicator may be configured such that the interface region has a distal side of a substantially flat surface for contacting tissue being treated and an opposite proximate side carrying one or more elements of the transducer arrangement and one or more elements of the cooling assembly.

The interface region of the applicator is preferably made of a heat conducting material and is configured to provide substantial impedance matching with impedance of the transducer arrangement, such that the ultrasound radiation passage through said interface region has energy losses substantially not exceeding 10%.

The ultrasound transducer arrangement is capable of selectively operating in one of the following operational modes: a continuous wave operational mode of a predetermined duty cycle, and a pulsed operational mode.

The applicator preferably also includes first and second temperature sensors configured and operable to measure respective first and second temperatures in vicinity of said arms of the U-shaped interface region and provide corresponding sensing data being indicative of temperature of surface tissue regions.

The control unit may be configured and operable to control the operation of said ultrasound transducer arrangement and said cooling assembly to provide maximum temperature of about 30 degrees Celsius at said interface region. The control unit may be configured and operable to control the operation of said ultrasound transducer arrangement and said cooling assembly to maintain temperature of the region of interest at deep location with respect to the region of interest to be at least 45 degrees Celsius during the treatment session. The control unit may be configured and operable to maintain said temperature of the region of interest to be in a range between 45 degrees Celsius and 55 degrees Celsius by modifying at least one operational parameter of said transducer arrangement, wherein said at least one parameter includes at least one of power-level and duty cycle of the ultrasound radiation.

The applicator may further include a tissue attachment mechanism configured and controllably operable by said acoustic contact control circuitry to provide a desired acoustic contact between said at least part of the interface region and the tissue under treatment. For example, the tissue attachment mechanism comprises a source of negative pressure for urging the tissue towards the interface region of the applicator. The acoustic contact control circuitry may be configured and operable to selectively increase or decrease a strength of the negative pressure upon identifying, respectively, decrease or increase in a prevailing average temperature of surface of the tissue under treatment. The acoustic contact control circuitry may be configured and operable to increase a strength of the negative pressure upon identifying, from said measured data, an increase in a prevailing average time-of-flight of the detected ultrasound radiation.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 3A to 3G illustrate some examples of various features of the ultrasound transducer assembly suitable to be used in the present invention, where FIGS. 3A to 3C illustrate examples of the opposing ultrasound transducer assemblies each including a single transceiver element, while FIGS. 3D to 3G illustrate examples of the opposing transducer assemblies each includes an array of transceiver elements; and where FIG. 3A exemplifies the transducer assembly associated with a single-layer configuration of an impedance matching cooling element at the interface region, FIG. 3B illustrates the transducer assembly associated with a multi-layer (stack) structure of such cooling element, and FIG. 3C exemplifies the transducer assembly associated with the impedance matching cooling element having a two-part configuration;

FIGS. 6A to 6C exemplify, by way of flow diagrams, a specific non limiting example of the procedure of ultrasound-based treatment of biological tissue using the device of the present invention, implementing a 'hybrid method' where the biological tissue is subjected to a first treatment stage for damaging adipocytes (e.g., inducing apoptosis thereof) and a second treatment stage for skin-tightening;

FIG. 7A illustrates the transducer arrangement including two opposing transducer assemblies being multi-element assemblies, FIG. 7B illustrates how such transducer assemblies can be used for treatment of skin portions and subdermal tissue.

FIG. 9A exemplifies distribution of the events of the second stage treatment (skin tightening treatment);

DETAILED DESCRIPTION OF EMBODIMENTS

Figure 1A:
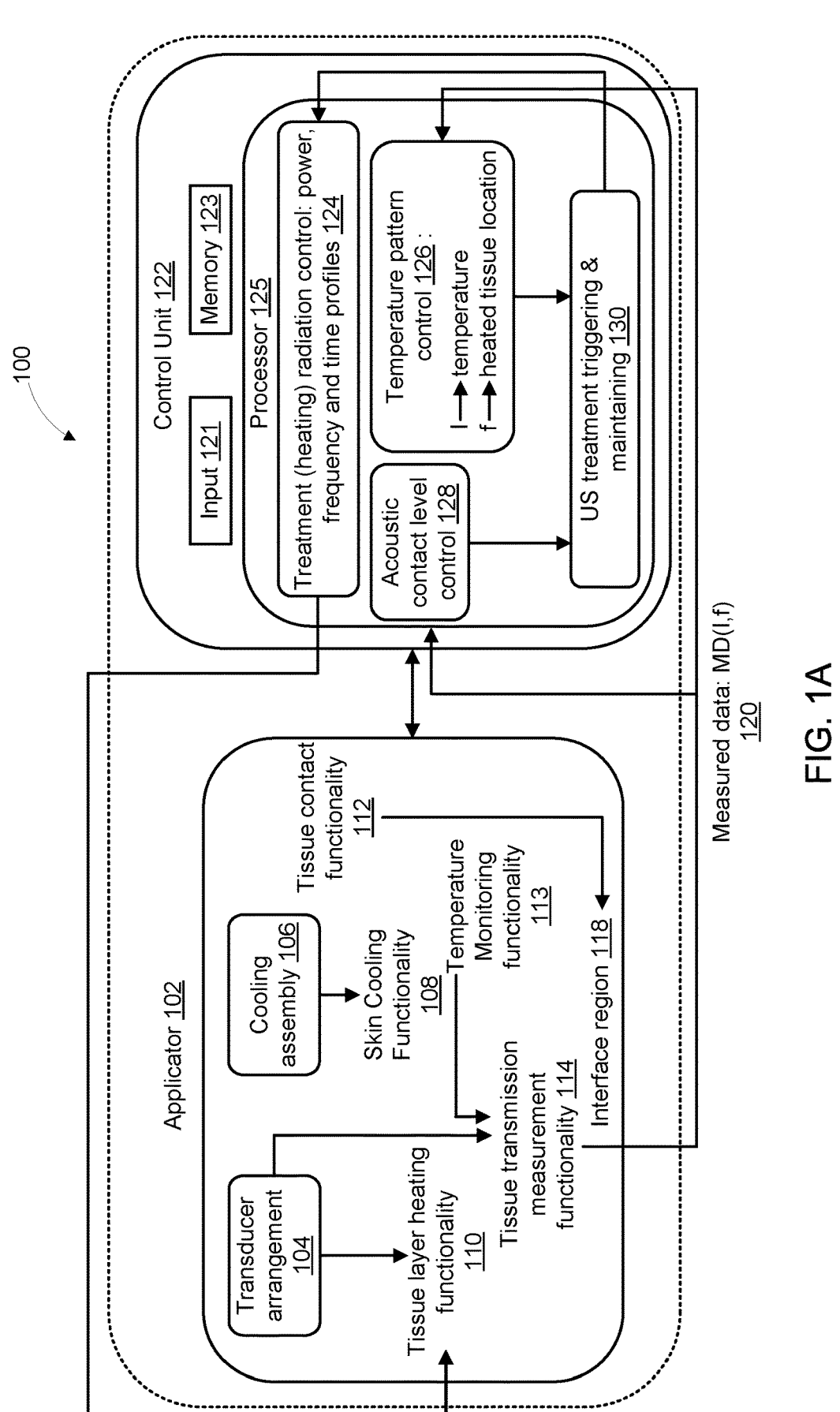
FIG. 1A schematically illustrates the functional utilities of a medical device of the present invention.
Figure 1B:
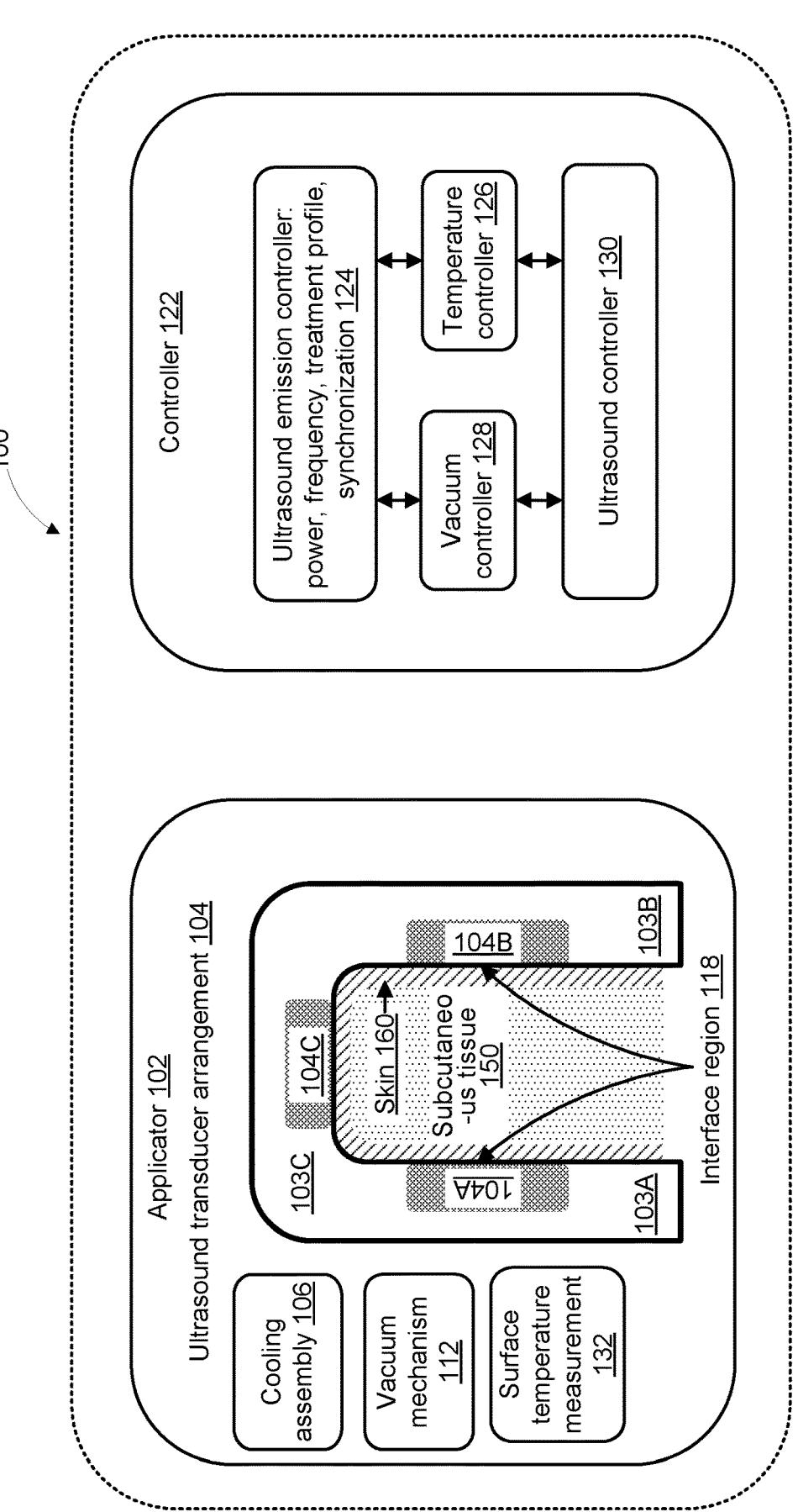
FIG. 1B exemplifies, by way of a block diagram, the medical device of the invention, showing more specifically an exemplary applicator configuration.
Figure 1C:
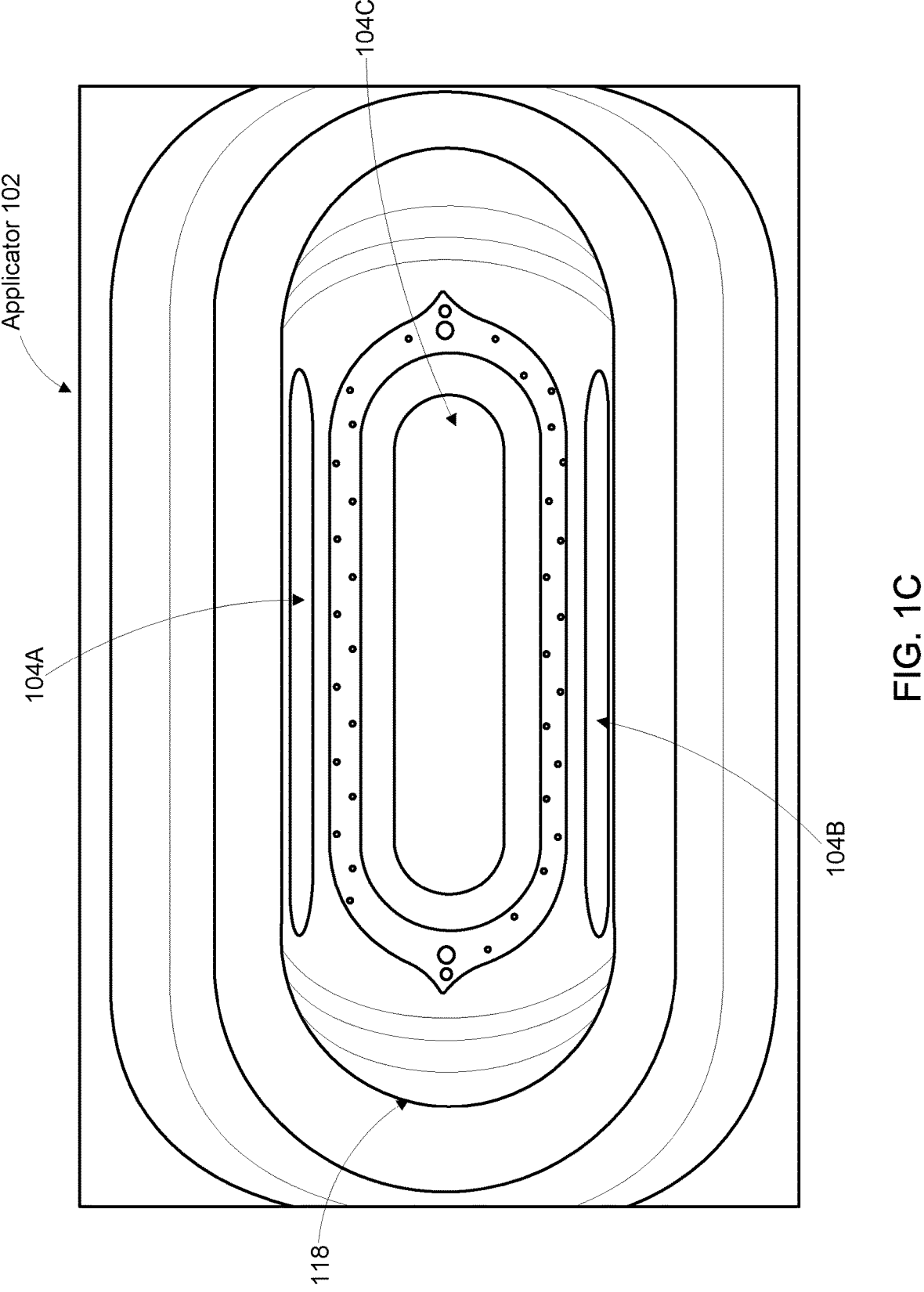
FIG. 1C is a picturized illustration of an exemplary applicator of the present invention.

Reference is made to FIGS. 1A-1C showing schematically a medical device 100 of the present invention illustrating its main elements and their functionality. The device 100 is configured to apply heat-based tissue treatment to an individual's body part. The device 100 includes an applicator 102 carrying a transducer arrangement 104 which is configured and controllably operable to perform a treatment session on at least one region of interest in tissue to achieve a desired treatment effect at each of said at least one region of interest. The applicator 102 is thus configured with tissue layer heating functionality 110 and is also configured with tissue contact functionality 112 and with tissue transmission measurement functionality 114 providing measured data 120 indicative of at least one of temperature of the region of interest and attachment of the tissue to the interface region with proper acoustic contact.

It should be understood that for the purposes of the present invention, desired attachment between the tissue surface and the interface region is defined by the acoustic contact level. Hence, although both of these terms "attachment" and "acoustic contact" are interchangeably used in the description below, they should be properly interpreted as explained.

The applicator is configured to define a U-shaped surface 118 (i.e., the applicator or at least a portion thereof has a parabolic-like cross-sectional geometry), which presents an interface for attachment with the body part such that each of the at least one region of interest within the body is located between opposite substantially flat surfaces of the arms of the U-shaped interface 118. Such U-shaped interface enables proper, substantially uniform, attachment of tissue being treated in a cavity defined by the U-shaped interface surface.

In the description below, such interface surface is at times referred to as "interface" or "interface region".

It should be noted that such configuration of the interface surface defined by the applicator defines a tissue cavity uniformly enclosing the surface of the tissue in the cavity, and provides for proper uniform attachment between the tissue surface and the interface of the applicator. This affects blood flow in blood vessels in the tissue "clamped" between the arms of the U-shaped interface region (causes the blood flow to be slower), which results in that, during treatment (heating), the blood vessels less "absorb" heat (as compared to that of blood vessels with regular blood flow) thus contributing to the effectivity of the tissue treatment. Also, such U-shaped configuration with rounded surface (with no corners) significantly improves the homogeneity/uniformity of the attachment during treatment avoiding "holes" in the attachment, thus avoiding burning of skin locations during deep tissue treatment which would otherwise occur at skin locations aligned with said holes.

The transducer arrangement 104 is configured and controllably operable to perform a treatment session on each region of interest by delivering heating radiation towards each region of interest. Generally, such heating energy can be provided by any known suitable type of transducer(s), e.g. transducer(s) delivering electromagnetic radiation. Preferably, however, the invention utilizes ultrasound energy for both treatment (heating) functionality 110 and control of treatment conditions functionality (collection of the measured data 120), and is therefore described below with respect to this specific configuration.

The applicator 102 further includes a cooling assembly 106 configured with skin cooling functionality 108 to perform cooling of at least a part of the interface region 118. The applicator 102 yet further includes tissue contact functionality 112 to provide a predetermined acoustic contact between the tissue and the interface region 118, and temperature monitoring functionality 113 for continuous monitoring and control of tissue temperature.

The applicator is associated with/includes a control unit 122 (local controller) which is an electronic device including, inter alia, data input utility 121, memory 123, and a processor 125. The processor 125 includes: acoustic contact level control circuitry 128 (vacuum controller); temperature controller 126 which controls the temperature pattern towards and along each region of interest; and ultrasound (US) radiation controller 130 which manages triggering and operation of the ultrasound emission controller 124. The treatment (heating) radiation control circuitry 124 operates for providing predetermined electric power to the transducer arrangement 104 for achieving predetermined profiles/patterns of heating power and time during the treatment, in accordance with a predetermined treatment protocol (which is region of interest specific and patient specific).

The acoustic contact level control circuitry 128 and the temperature pattern control circuitry 126 receive the measured data (MD) 120 from the applicator 102 and determine, respectively, whether the acoustic contact between the tissue and the interface region 118 and the temperature of the region of interest satisfy predetermined conditions. If the acoustic contact satisfies the predetermined condition, circuitry 128 operates the circuitry 130 to trigger the treatment session and maintains the US emission during the treatment session to thereby maintain a predetermined temperature pattern at predetermined tissue locations during the treatment session.

It should be noted that the above circuitries of the control unit include any suitable hardware/software utilities (e.g., digital and/or analog electronics, or software or combinations thereof). In some embodiments, such "circuitry" includes a digital computer. "Analysis circuitry" is typically an electronic circuitry configured to perform a data-analysis function. "Memory" or "storage" (used interchangeably) refers to volatile (e.g. RAM) and/or non-volatile (e.g. flash or magnetic medium) computer storage. "Circuitry" or "memory" may be local to a given device (or locally-coupled devices) or may be non-locally distributed.

In FIG. 1B one non-limiting embodiment of the applicator 102 is shown, exemplifying the main blocks of the applicator 102. According to the invention, the applicator 102 is configured to define a substantially U-shaped interface region 118 to engage folded biological tissue. It should be noted that the applicator may be configured with a U-shaped surface that forms the interface region; or may be configured with a substantially flexible and foldable surface such that it is adapted to define the substantially U-shaped interface region when the applicator is brought to operation.

Thus, when the applicator 102 is brought in operation, the interface region 118 is in contact with skin portion 160, and deep region(s) of interest 150 is/are located between opposite arms 103A and 103B of the U-shaped interface region 118, thereby enabling attachment of tissue being treated between substantially flat surfaces of these arms. According to the invention, the ultrasound transducer arrangement 104 includes opposing first and second ultrasound transducer assemblies 104A and 104B defining, respectively, first and second substantially flat ultrasound-transceiving surfaces located on opposite arms 103A and 103B of the U-shaped interface region 118. The ultrasound-transceiving surfaces of the transducer assemblies 104A and 104B are facing one another and configured to produce at least one pair of first and second ultrasound radiations from the first (104A) and second (104B) ultrasound transducer assemblies propagating along substantially coinciding (laterally aligned) axes towards the region(s) of interest in the tissue being engaged between the opposite arms of the interface region 118.

The above configuration of the transducer arrangement provides that the transducer arrangement is adapted to perform the treatment session on each region of interest, and also perform a control session by detecting the ultrasound radiation passed through the tissue and generate the measured data 120 indicative thereof. It should be noted that with this configuration, the first and second transducer assemblies are preferably configured and controllably operated to generate the first and second ultrasound radiations of respectively first and second at slightly different frequencies to avoid or at least significantly reduce a standing wave effect. For example, the frequencies may differ from one another by 0.5%-15%.

As will be described more specifically below, the first and second transducer assemblies 104A and 104B include, respectively, first and second arrays of independently operable transceiver elements, thereby defining at least two opposing pairs of the ultrasound transceiver elements generating the first and second substantially mutually laterally aligned ultrasound radiations in opposite directions towards the region of interest in the tissue. For example, four such pairs of the opposing transducer elements may be used.

As exemplified in the figure, in some embodiments/ applications, e.g. skin tightening, the transducer arrangement 104 includes an additional transducer assembly 104C located between the transducer assemblies 104A and 104B. The additional transducer assembly 104C may be located at the base part 103C of the U-shaped interface region.

FIG. 1C illustrates an exemplary applicator 102 of the present invention, showing the U-shaped surface 118 which defines a cavity for tissue placement therein and thus presents an interface with the tissue being treated. As also shown in the figure, the transducer arrangement carried by the applicator includes the opposing transducer assemblies 104A and 104B located at the opposite arms of the U-shaped surface, and in this example also includes the intermediate transducer assembly 104C.

As also shown in the FIG. 1B, the applicator includes appropriate vacuum mechanism 112 (generally, negative-pressure mechanism). To this end, the surface of the applicator defining the interface region 118 is typically formed with small perforations (not shown here) enabling tissue attachment by suction. Such mechanism is known per se and need not be specifically described. The vacuum mechanism is associated with the vacuum controller 128 which, according to the invention, control the vacuum level by monitoring the acoustic contact between the tissue and the interface region based on the measured data, as will be described more specifically further below.

Also, the applicator 102 includes the cooling assembly 106, which is configured and operable to controllably cool the interface region 118. The cooling assembly may be of the type providing fluid-based cooling (water, air) or may include solid state Peltier TEC modules, whose configuration in this regard will be described further below.

As also exemplified in the figures, the applicator 102 includes surface temperature measurement assembly 132, e.g., a thermocouple properly attached to/incorporated in the interface region 118.

As described above, the ultrasound emission controller 124 is configured and operable to control operation of the ultrasound transducer arrangement 104, in particular, to control the power and frequency of the ultrasound radiation to achieve a desired treatment effect at the desired region of interest, according to the predetermined treatment protocol. The ultrasound emission controller 124 is synchronized with the temperature controller 126 and the vacuum controller 128 to achieve the predetermined temperature pattern and attachment during the treatment session.

The ultrasound transducer arrangement 104 is configured as described above and thus provides measured data 120 indicative of time-of-flight data of ultrasound pulse between the first and second transducer assemblies and thereby corresponds to time-of-flight of ultrasound radiation through the tissue engaged between the opposite arms of the interface region. This enables to extract from the time-of-flight data in real time an average temperature of the region of interest being a deep region with respect to the interface region.

It should be noted that in the description below the ultrasound radiation used for time-of-flight measurement is at times referred to as "pulsed radiation", and also ultrasound radiation used for skin tightening treatment is referred to as "pulsed mode" or "pulsed ultrasound radiation". However, these are different types of radiation: the pulsed radiation used for the time-of-flight measurements includes one (or more) relatively long pulse(s), where the time-of-flight of each such long pulse is determined, while the pulsed mode used for skin tightening stage of treatment is in the form of a sequence of short intervals of generation/transmission of tone burst ultrasound radiation.

Figure 2:
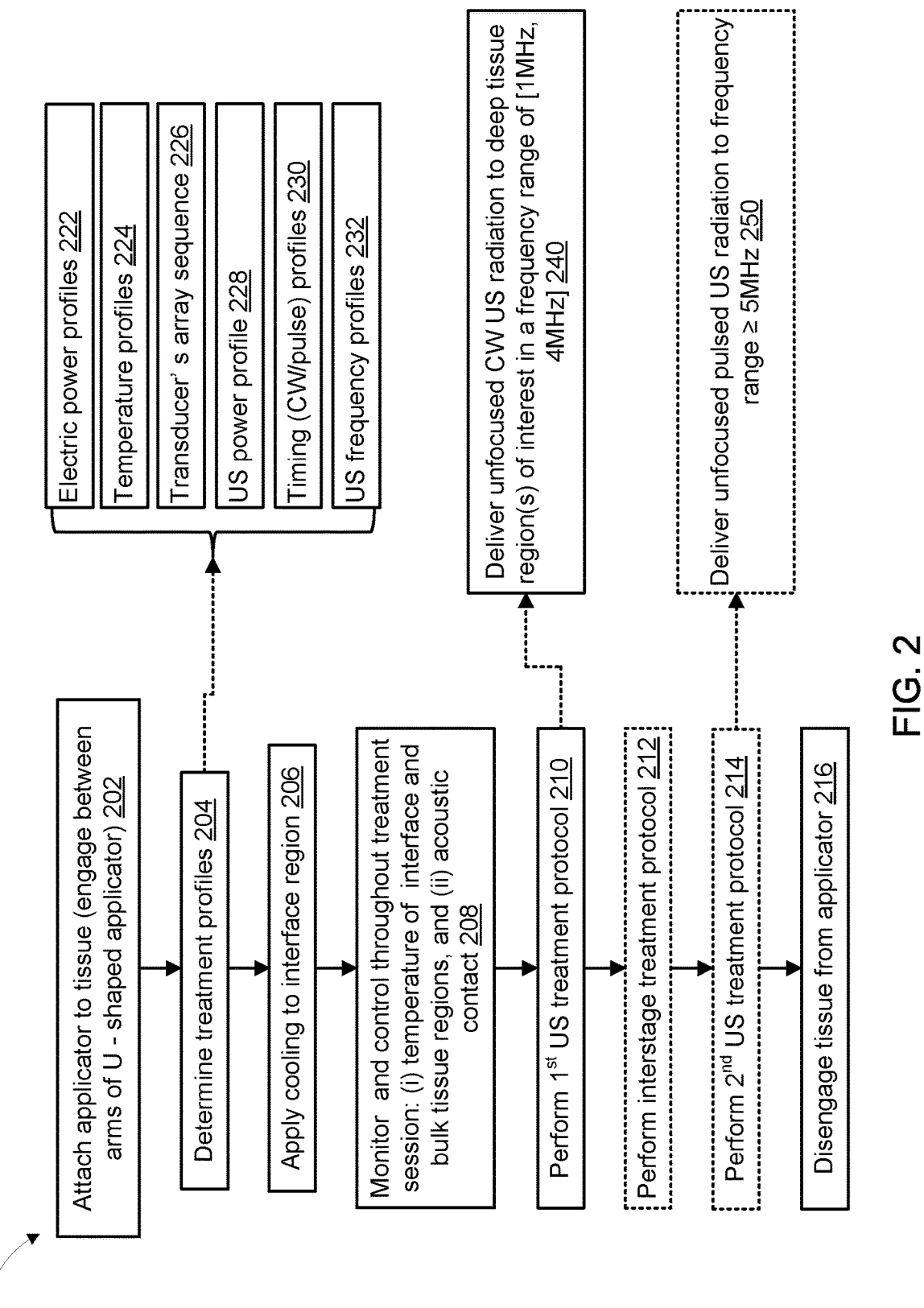
FIG. 2 exemplifies, by way of a flow diagram, operational scheme of the device of the present invention for treatment of a biological tissue.

Reference is made to FIG. 2 showing a flow diagram 200 of a method of treatment of the biological tissue using the device 100 of the present invention. The treatment begins with attachment of the applicator 102 to tissue to be treated by engaging the tissue between the arms of the U-shaped applicator and applying e.g., negative pressure to the interface region(s) 118 (step 202). The treatment protocol, which is previously established in accordance with the region of interest to be treated, is then optimized for a specific patient by determining various treatment profiles (step 204).

Such profiles include for example one or more of the following: electric power profiles (222), temperature profile(s)/condition(s) (224) with respect to location of region(s) of interest of specific tissue in the treated body part; operational sequence (226) of the transducer assemblies; ultrasound power profiles (228); ultrasound frequency profiles (232) where the choice of frequency is different for deep or shallow region of interest and specific frequency requirements from opposing transceiver elements are needed to avoid standing wave effects; and the treatment timing profiles for heating (treatment) and control sessions (230).

The session starts with applying cooling to the interface region (206) to guarantee. at all times during the treatment, a certain maximum temperature at the interface region 118 (e.g. temperature of about 30° C.) being in close thermal contact with the upper layer of the skin. It should be understood that once the epidermis temperature is 30° C., the dermis temperature will be several degrees higher. Throughout the treatment session, the temperature of the interface region 118 (and accordingly that of skin region) and bulk/deep tissue regions, as well as the acoustic contact of the interface region 118 to the tissue, are monitored and controlled (208).

In some embodiments, the first US treatment protocol (e.g., aimed at fat reduction) is then performed (210) while delivering unfocused continuous wave (CW) ultrasound radiation to deep tissue region(s) of interest. This can be implemented utilizing radiation in the frequency range of 1 MHz to 4 MHz (240).

A non-limiting example of treatment may begin by evenly heating the fat tissue to about 48° C., and then maintaining it during the treatment session, thus causing fat cells apoptosis, all this while keeping the dermis at about 30° C. The target temperature (e.g., 48° C.) may for example be reached within 5 minutes, and the first stage treatment may last, in some embodiments, for about 17 mins. At the end of the first treatment protocol, in some embodiments, an interstage treatment protocol is performed (212) in case a second US treatment protocol (214) (e.g., skin tightening) is planned. The interstage treatment protocol may include, for example, a tissue cooling period when all ultrasound transducer assemblies are dormant.

In some embodiments, the second US treatment protocol 214 may involve delivering pulsed ultrasound radiation (tone burst radiation as described above) to shallow tissue region(s) of interest using frequencies of at least 5 MHz (i.e. 5 MHz or higher) (250). Such high-frequency treatment may rapidly heat the upper and lower layers of the dermis by small sections, thus promoting the creation of collagen and elastin.

The treatment session ends with disengagement of tissue from the applicator (216).

It should be noted that at least part of the second stage 214 (whose duration is at least one minute and which concludes no later than 60 minutes after the conclusion of the first stage time period 210), the transducer assembly 300C (at the base of the U-shaped applicator) delivers ultrasound radiation in the pulsed mode (i.e. sequence of spaced-apart tone bursts) and having frequency of at least 4.5 MHz (or at least 5 MHz or at least 5.5 MHz or at least 6 MHz or at least 7 MHz or at least 8 MHz or at least 9 MHz).

Reference is made to FIGS. 3A to 3G, each showing a possible embodiment of ultrasound transducer assembly 300 (104A, 104B in FIG. 2) according to the teachings of the present invention.

Figures 3A, 3B:
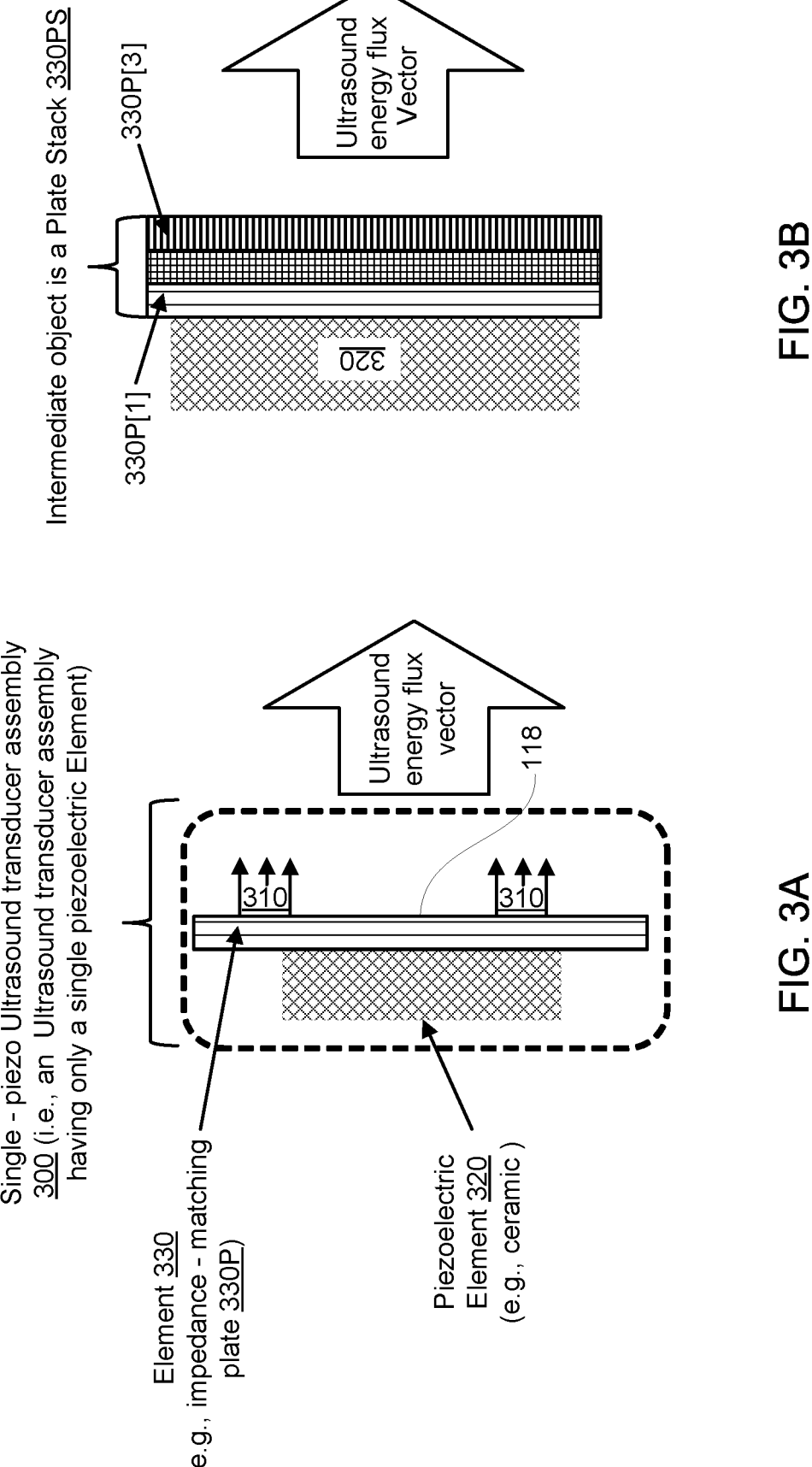

The ultrasound transducer assembly 300 includes: one or more piezoelectric transducer element(s) 320 (e.g., typically ceramic element), and a plate-like element 330 that is by its one side (proximate side) in contact with the piezoelectric transducer element(s) 320 and whose opposite side (distal side 310) defines the interface region or faces the interface 118 defined by a surface of another element (e.g. enclosure). In FIG. 3A, the element 330 is a single-layer plate 330P, whereas in FIG. 3B such element 330 is a multi-layer (stack) structure 330PS where an outer surface of layer 330P[1] is in contact with the piezo element 320 and ultrasound energy is transmitted out of the transducer assembly via an outer surface of the layer 330P[3].

The plate-like element 330P may be constructed from a metal (e.g., aluminum or copper or bronze). In one example, plate 330P may be an aluminum plate. Generally, the material composition and geometrical parameters of the plate-like element are selected to provide desired properties of the interface region (either directly contacting the tissue or via enclosure) of the applicator. These properties include heat conductivity substantial impedance matching with impedance of the transducer arrangement, such that the ultrasound radiation passage through said plate like element (and thus through the interface region) has energy losses substantially not exceeding 30%.

As described above, the ultrasound transducer arrangement is configured such that it includes at least one pair of first and second opposing transducer assemblies generating first and second ultrasound radiations propagating along substantially coinciding (laterally aligned) first and second axes towards one another. Thus, each transducer assembly "directional transmission/reception" and the opposing operation of the pair of such assemblies/elements provides for treatment and control sessions based on transmission and reception of the ultrasound radiation.

As shown in FIG. 3A, the ultrasound transducer assembly includes a transceiving surface 310 through which ultrasound energy is transmitted from the ultrasound transducer assembly to the tissue and through which ultrasound radiation generated by the opposing transducer assembly (not shown here) and passed through the tissue is received. This received radiation is subsequently detected by one or more piezoelectric elements 320 (e.g., ceramic) of the transducer assembly 300. The transceiving surface 310 is defined by the surface of the plate-like element 330.

When a transducer element vibrates at an ultrasound frequency (e.g., between 0.5 MHz and 20 MHz), this causes the plate-like element 330 to vibrate at the ultrasound frequency as well, and ultrasound energy, characterized by an ultrasound energy flux vector, is transmitted via the transceiving surface 310. Thus, the ultrasound transducer assembly 300 is directional and is associated with a direction of an 'ultrasound energy flux vector' which is a direction of propagation of ultrasound energy exiting via the outer surface of the plate-like element 330 (interface region).

Figure 3C:
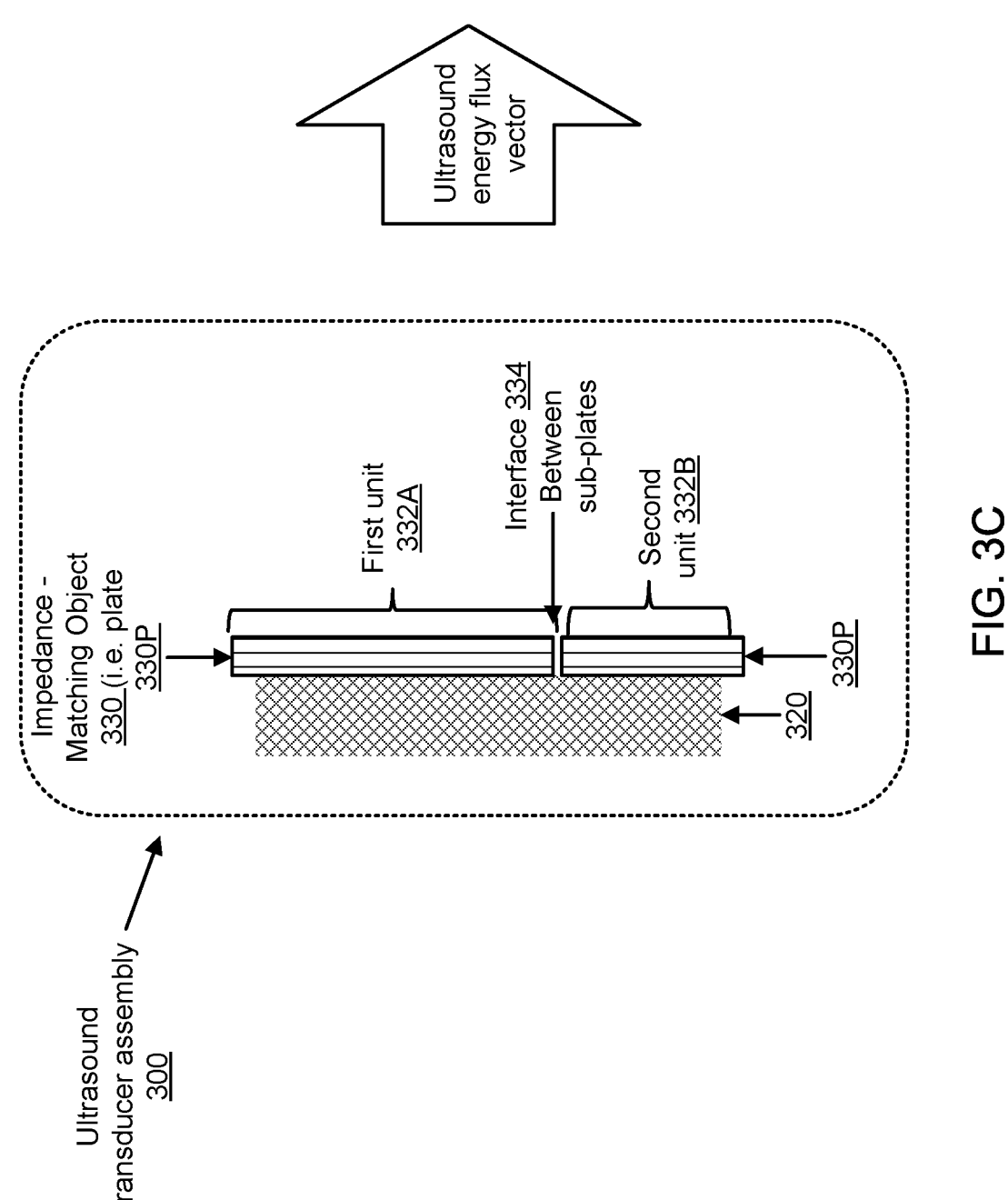

FIGS. 3C-3F show some other non-limiting examples of the configuration of an ultrasound transducer assembly. In FIG. 3C, the impedance matching heat-conducting plate-like element 330P is a two-part unit formed by first unit 332A and second unit 332B defining an interface 334 between them. Using multi-piezo ultrasound transducer with square piezo elements provides homogeneous expansion of an acoustic field (homogeneous heating of tissue).

In the non-limiting examples of FIGS. 3A to 3C each of the opposing ultrasound transducer assemblies (one such assembly 300 being shown in the figures) as having a single piezoelectric transducer 320 and thus defining a single transducer element. In other examples, as shown in FIGS. 3D to 3G, each of the opposing transducer assemblies (one such ultrasound transducer assembly 300 being shown in FIGS. 3D, 3F and 3G) includes an array of any number of piezoelectric elements and thus an array of transceiver elements. Thus, the ultrasound transducer assemblies 300 of FIGS. 3D to 3G are all multi-piezo ultrasound transducer assemblies 300 and as shown specifically in FIG. 3E the ultrasound energy flux vectors of the ultrasound radiations produced by each of the transducer piezo elements 320A-320D of the same transducer assembly are aligned with each other (i.e. directed along spaced-apart substantially parallel axes), to provide a common energy flux vector direction.

Figure 3D:
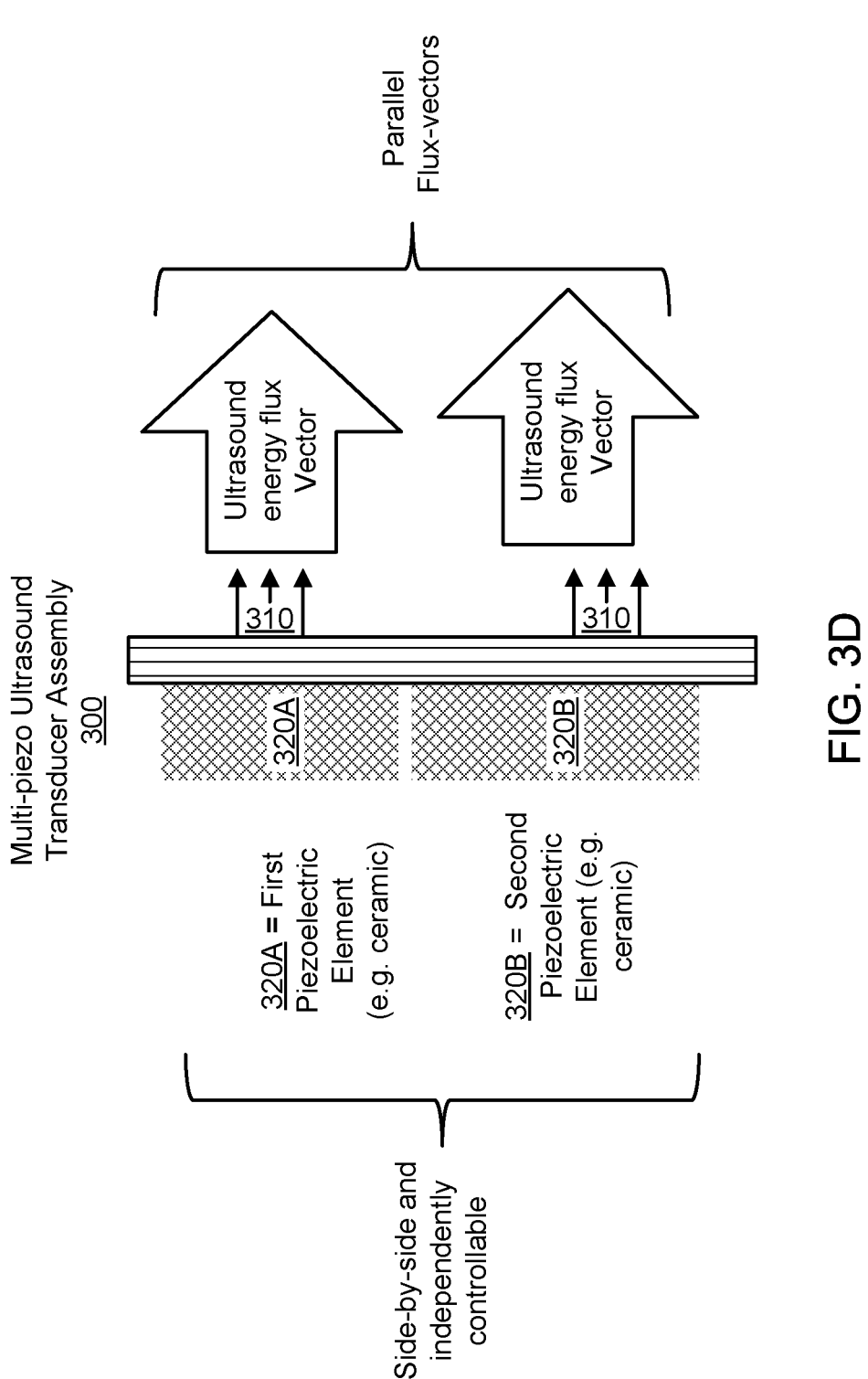

FIG. 3D shows an example of the above, where ultrasound energy flux vector of energy produced by transducer piezo element 320A and transmitted by an outer surface of plate-like element 330 (e.g., plate 330P) is aligned with ultrasound energy flux vector of energy produced by transducer piezo element 320B and transmitted by an outer surface of the same plate-like element 330 (e.g., plate 330P).

Each ultrasound transducer piezo element 320A, 320B of the transducer assembly 300 in FIG. 3D may be independently controllable to transmit the ultrasound energy non-simultaneously (in different intervals of treatment) or simultaneously.

In FIG. 3E two opposed ultrasound transducer assemblies 300 are shown while exemplifying two pairs of opposed transducer piezo elements 320AA-320BA and 320AB-320BB. Each of the piezo elements is configured as a transceiver operable to selectively transmit or receive ultrasound radiation. The paired elements (whose transceiving surface face one another) transmit/receive radiation along substantially coinciding axes. In non-limiting example of FIG. 3E, the transducer piezo elements 320AA and 320BB operate in the transmit mode and transducer piezo elements 320BA and 320AB operate in the receive mode.

Figure 3F:
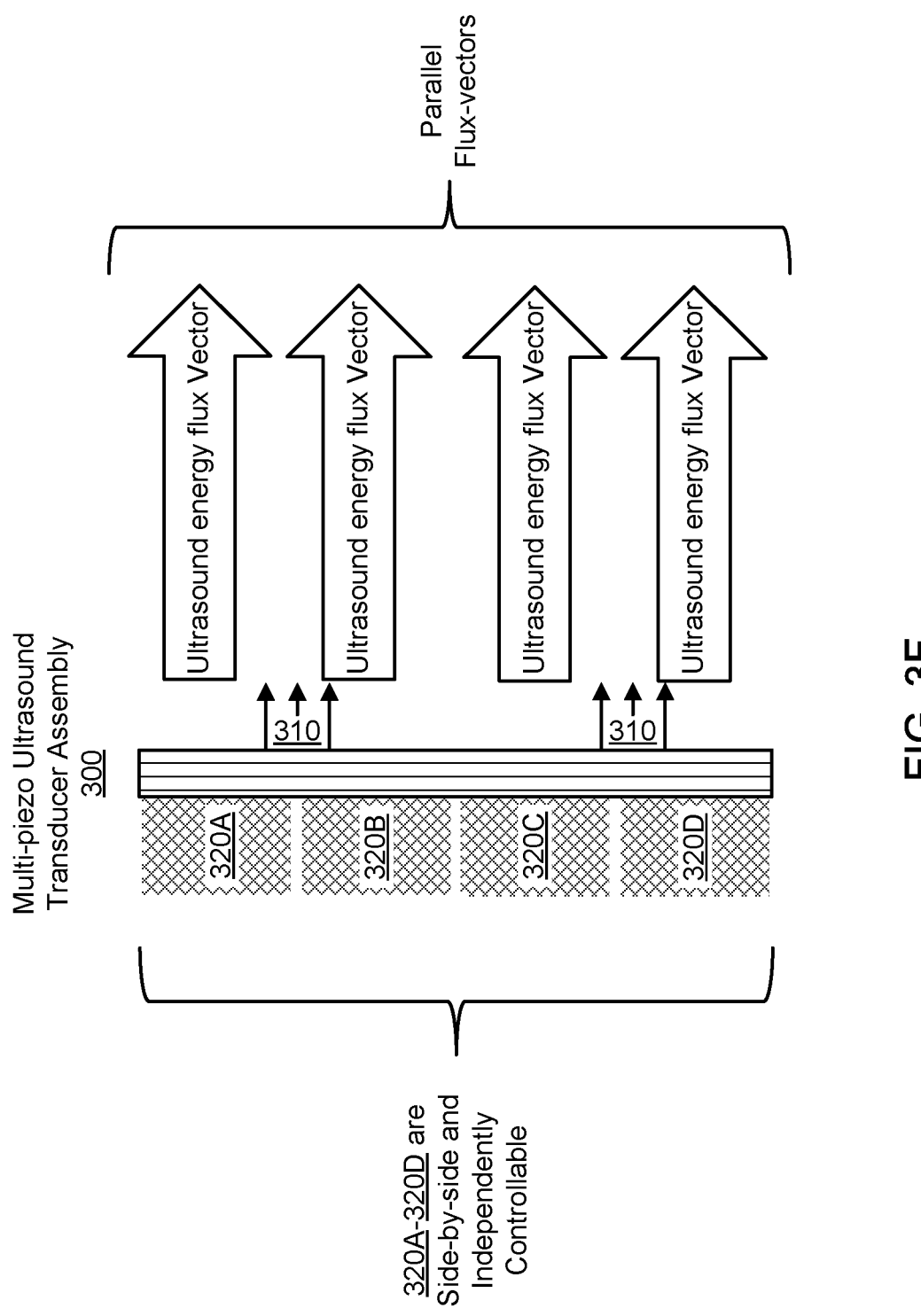

The example of FIG. 3F exemplifies the ultrasound transducer assembly 300 including four piezoelectric ultrasound transducer elements 320A-320D. The ultrasound energy flux vectors from all the four piezo elements are aligned with each other, and collectively define a common ultrasound-transmission direction of the ultrasound transducer assembly 300.

Figure 3G:
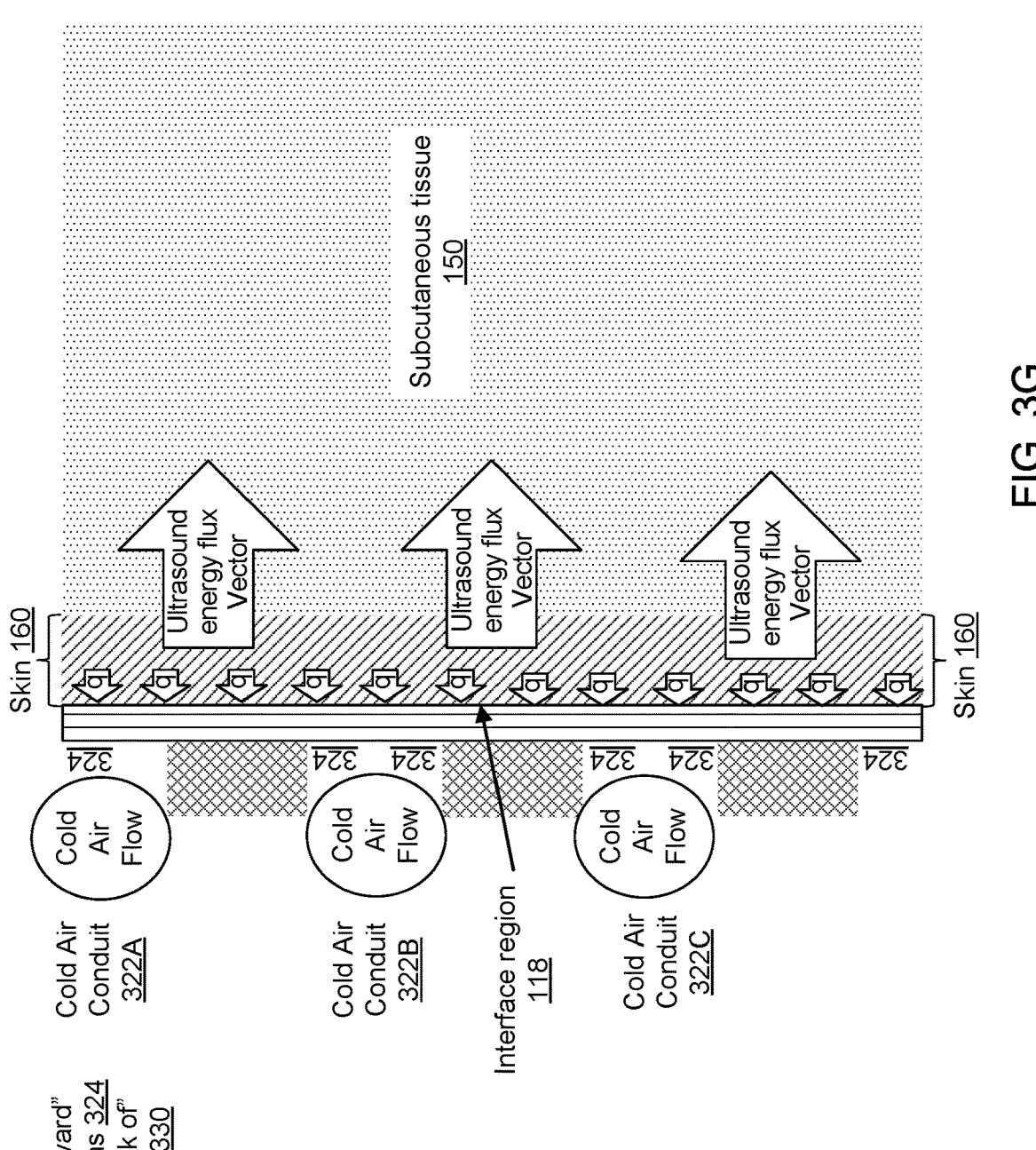

FIG. 3G illustrates an ultrasound transducer assembly 300 exemplifying configuration and operation of the cooling assembly for properly cool the interface region, e.g. by performing a so-called "contact-cooling". For example, a cold fluid (e.g. air or water or any other fluid) is forced to flow in one or more conduits 322A-322C or in any other manner within backward locations 324 relative to plate-like element 330 defining the interface region. In FIG. 3G, q represents heat-flow. Thus, the ultrasound transducer assembly 300 exemplified in the figure operates to cool at least an outermost layer of skin 160 while heating deeper layers of subcutaneous biological tissue 150.

Figure 4A:
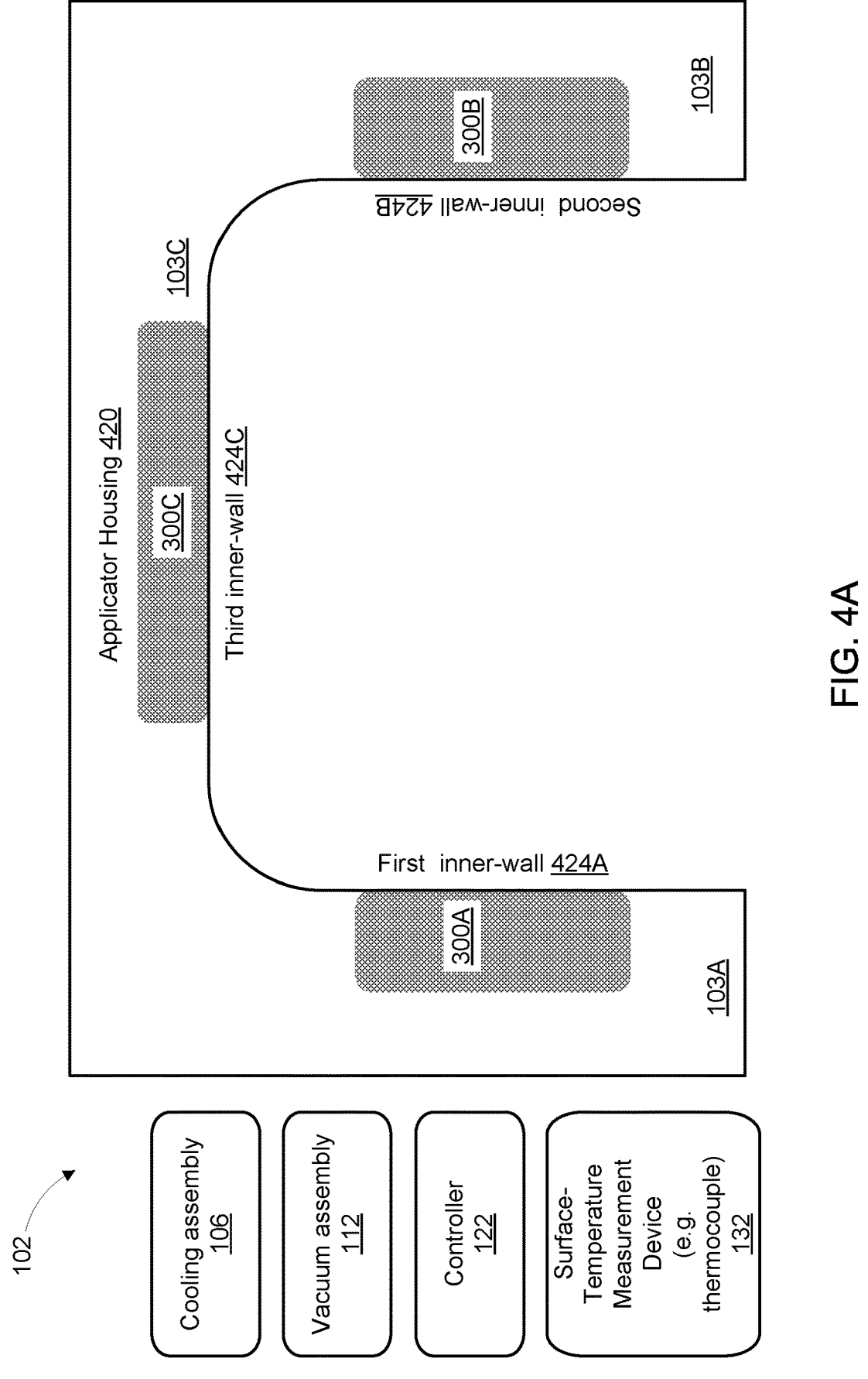
FIGS. 4A and 4B more specifically illustrate the exemplary applicator of the present invention.
Figure 4B:
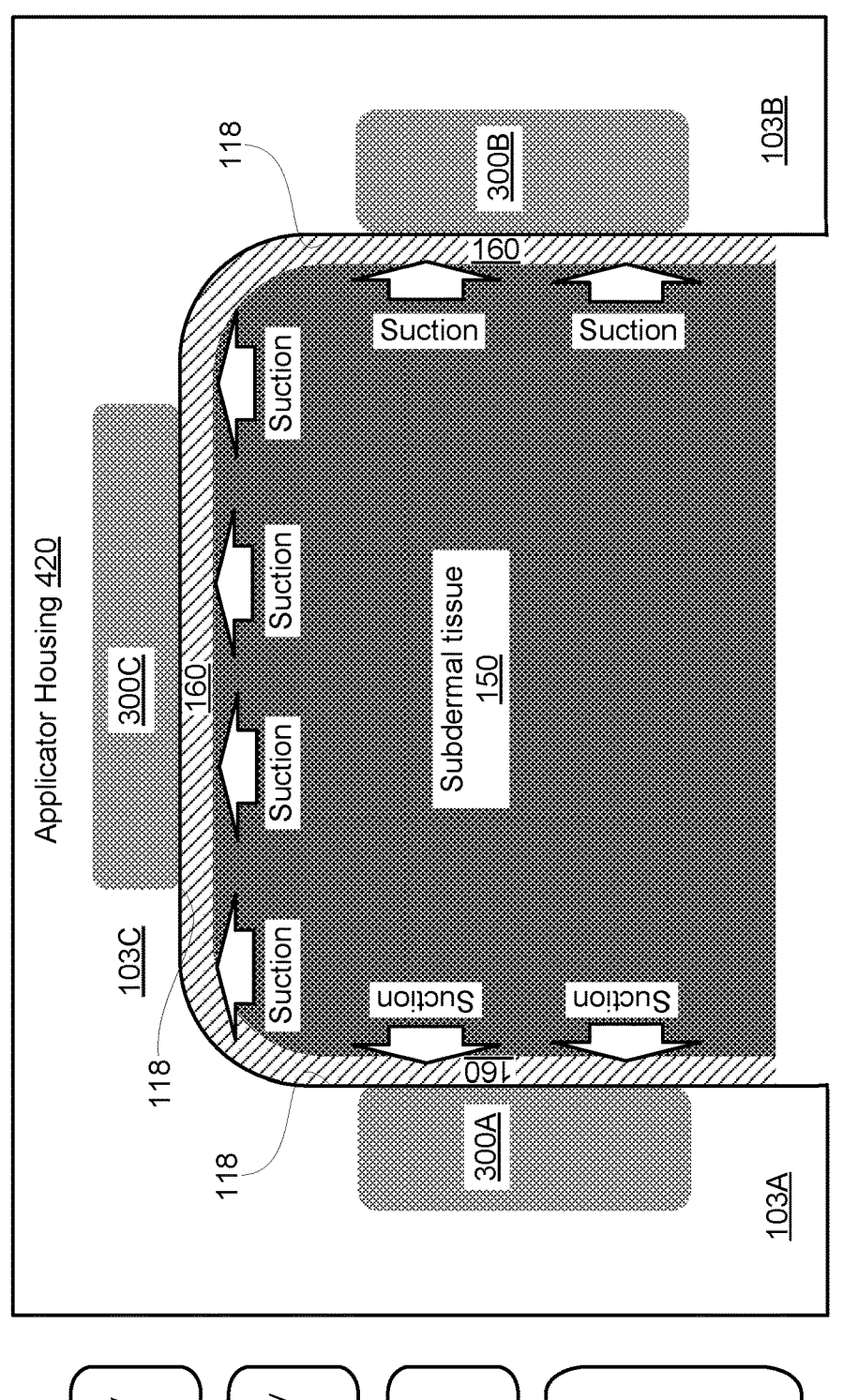
Figure 4C:
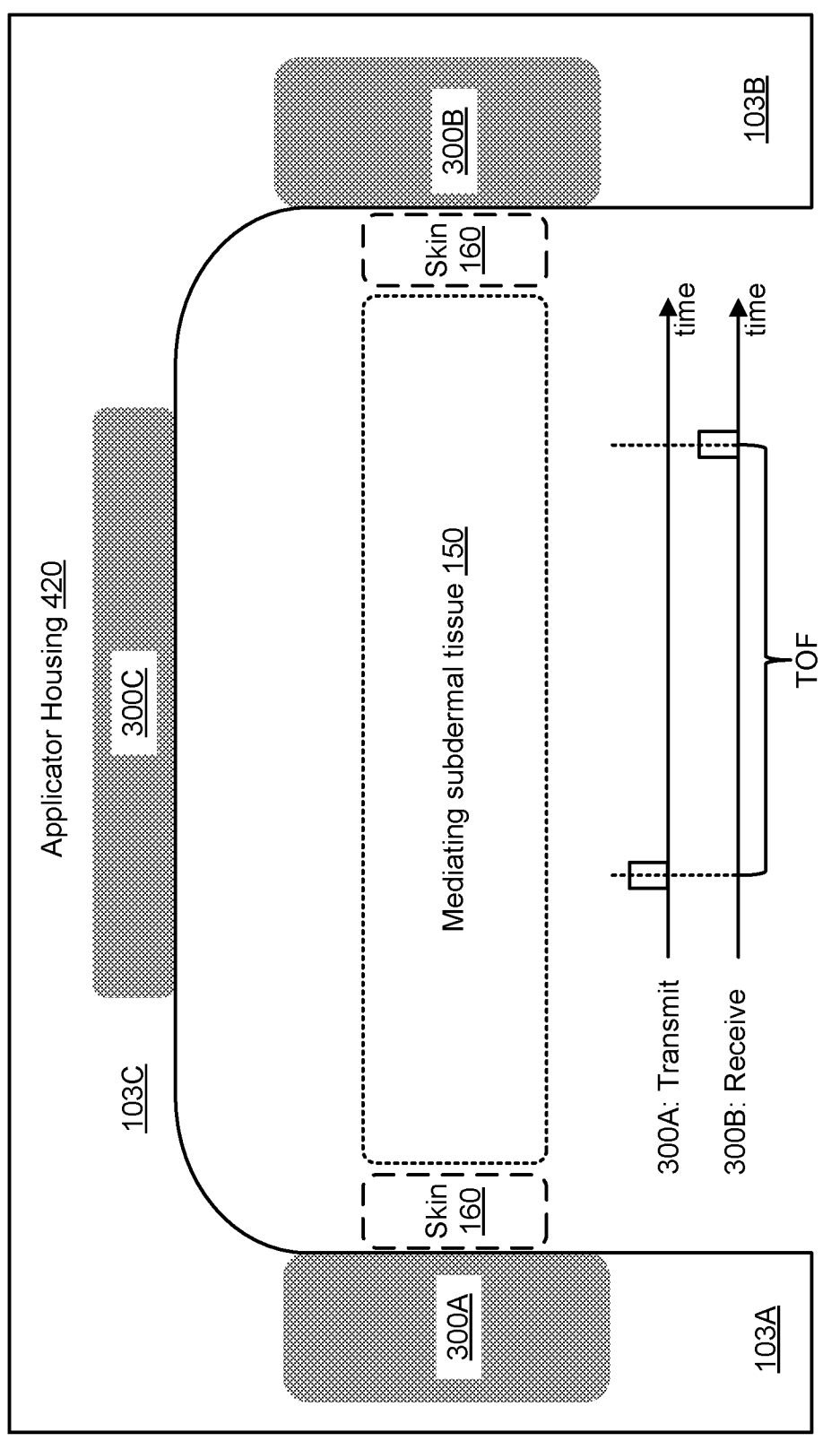
FIG. 4C schematically illustrates operation of the applicator of the present invention to provide temperature control using the opposing ultrasound transducer assemblies.

Reference is made to FIGS. 4A to 4C which exemplify in more detail the structure of the applicator 102 carrying the transducer arrangement 104. The applicator 102 has a U-shaped housing 420 integrating elements of the transducer arrangement 104, i.e. first and second opposing transducer assemblies 300A and 300B and in some embodiments also an intermediate transducer assembly 300C.

Housing 420 has three inner-walls 424A-424C all facing a common central region—in particular, walls 424A and 424B are disposed on opposed arms of applicator 102 and face each other, and the third wall 424C mediates between the first 424A and second 424B walls. The opposing ultrasound transducer assemblies 300A, 300B are, respectively, disposed on and/or embedded in the first inner-wall 424A and second inner-wall 424B of the housing 420 and face each other. As described above with reference to FIG. 3E, the direction of ultrasound delivered by ultrasound transducer assembly 300A into the central region (i.e., a direction of ultrasound energy flux vector of assembly 300A) opposes the direction of ultrasound delivered by ultrasound transducer assembly 300B into the central region (i.e., a direction of ultrasound energy flux vector of assembly 300B).

The transducer assembly 300C is also "directional" and the axis of propagation of ultrasound delivered into the central region by ultrasound transducer assembly 300C (i.e. a direction of ultrasound energy flux vector of assembly 300C) is normal to the axes of propagation of ultrasound radiations delivered into the central region by ultrasound transducer assemblies 300A and 300B.

Turning back to the illustration of FIG. 1B, the applicator 102 is shown there facing up in order to show the central region (base region) of the U-shaped structure of the applicator/housing between the arms thereof. During operation of the device of the present invention, a quantity of biological tissue fills the central region of the applicator being properly attached to the interface region there along, e.g., by suction as shown in FIG. 4B.

In some embodiments, each of ultrasound transducer assemblies 300A, 300B, (and also assembly 300C if used) is disposed on and/or embedded within the respective one of inner walls 424A, 424B (and possibly 424C), such that during treatment the biological tissue is in direct contact with the respective plate-like element 330 of the ultrasound transducer assembly.

In some embodiments, the configuration of the applicator provides that the ultrasound transducers assemblies 300A and 300B collectively form structures (e.g. plates) with parallel flat transceiving surfaces having a constant surface-to-surface (plate-to-plate) separation.

FIG. 4B illustrates the applicator 102 when biological tissue 150 (subdermal tissue) including skin portion 160 is disposed within the central region of the applicator (i.e. cavity defined by the U-shaped applicator). Skin portion 160 is in contact with the interface region 118 and thus in contact with each transceiving surface of each of transducer assemblies 300A, 300B, 300C.

FIG. 4B further illustrates schematically that the 102 is associated with/includes cooling device 106; vacuum mechanism/assembly 112; controller 122, and surface-temperature measurement device 132 (e.g. thermocouple). The surface-temperature measurement device 132 can measure a temperature of any of surfaces 424A, 424B and 424C and/or an upper surface of biological tissue (e.g., skin portion) in contact therewith.

In some embodiments, vacuum assembly 112 retains the biological tissue in the central region of the applicator and/or provides pressurized contact between a surface of a skin portion 160 and interface region defined by inner walls 424A, 424B, 424C of the applicator housing 420 and thus the respective forward-facing transceiving surfaces 310 of the ultrasound transducer assemblies 300A, 300B, 300C. The vacuum assembly may include a perforated vacuum filter.

The strength of the vacuum may be controlled by static or dynamic mode. As described above, thus is preferably implemented via measurement/estimation of the acoustic contact between the tissue and the interface region (and this the transceiving surfaces of the transducers) using the measured data indicative of time-of-flight data for the ultrasound radiation generated and detected by respectively first and second paired (opposing) transducer elements. Additionally, other suitable sensor(s) can be used such as proximity-sensor and/or pressure-sensor. In the event the acoustic contact level control circuitry (128 in FIG. 1A) of the control unit identifies that the acoustic contact is outside of prescribed level/range, e.g. contact is lost and/or an area of skin portion in contact with the interface region decreases and/or a pressure between skin portion and the interface region (transceving surface of the transducer assembly) is "too low," a strength of negative pressure provided by vacuum assembly 112 may be increased. In the example of FIG. 4B, vacuum apparatus provides suction towards respective inner walls 424A, 424B, 424C of the applicator housing 420.

The cooling assembly 106 may be configured to provide contact cooling between an outer surface of the plate-like element 330 (e.g., outer surface 310 of plate 330P in FIG. 3A for transducer assembly 300A and/or transducer 300B and/or transducer 300C) and an upper surface of skin portion 160 in contact with this outer surface. For example, outer surface of plate-like element 330 may be controlled to a set-point temperature or to a maximally permitted temperature. For example, cooling assembly 106 may utilize fluid cooling mechanism (e.g., liquid or gas, e.g., water or an aqueous solution) present in a backwards location 324 in the back of plate 330P (e.g., see FIG. 3G).

In another example (not shown), plate 330 may be configured as a Peltier-Thermoelectric Cooler or a portion thereof, e.g., to cool surface 310.

Thus, in embodiments of the invention, elements of (or an entirety of) the thermoelectric cooler or of the convention-cooler (e.g., see FIG. 3G) may be considered as the components of cooling assembly 106 for cooling interface region at least at portions thereof constituted by transceiving surfaces 310 of the ultrasound transducer elements.

In embodiments of the invention, operation of cooling mechanism (i.e. to cool any of 424A and/or 424B and/or 424C and/or respective surfaces 310 of transducer assemblies 300A, 300B, 300C, for example, controlled to a temperature range having a maximum of at most 35° C. or 30° C. or 25° C. or 20° C.) is controlled with the results of a surface-temperature measurement of the interface region 118 and thus an upper surface of skin portion 160 in direct contact with portions of interface region (424A and/or 424B and/or 424C) and/or respective surfaces 310 of transducer assemblies 300A, 300B, 300C.

As described above, the operation of the cooling assembly can be controlled in accordance with measured data indicative of the time-of-flight of the ultrasound radiation and/or measured data obtained by a separate surface-temperature measurement device 132. Such surface-temperature measurement device 132 may include thermocouple(s).

Regarding an average temperature of biological tissue disposed in the mediating region between the arms of the U-shaped interface region of the applicator, this is preferably obtained based on the time-of-flight data extracted from the detected ultrasound radiation as describe above. Additionally, or in some embodiments alternatively, such average temperature of biological tissue may be evaluated by measuring an amount of current required to cool the interface region (and thus the upper surface of skin portion) to a known (predefined) set-point temperature combined with mathematical model about thermal properties of the biological tissue.

FIG. 4C schematically illustrates that the novel configuration of the applicator of the present invention provides for temperature control using the operation of the opposing transducer assemblies. As shown in the figure, the transducer assemblies are arranged such that they define at least one pair of opposing first and second substantially flat ultrasound-transceiving surfaces located at the opposite arms of the U-shaped interface region (424A and 424B in FIG. 4B) defined by opposing first and second transducer assemblies 300A and 300B.

The first ultrasound transducer assembly (e.g., 300A) is configured to transmit directional ultrasound radiation and the second ultrasound transducer assembly (e.g., 300B) is configured to receive ultrasound radiation. It should, however, be understood that each transducer assembly may be configured for both transmission and receiving ultrasound radiation and is therefore termed here as transceiver (defining transceiving surface), while the device operation protocol may set one of the paired opposing transducer elements to operate as transmitter and the other as a receiver.

The average temperature of the deep region of interest, i.e. subdermal tissue portion 150 engaged between the opposite arms of the interface region, may be measured in real time by measuring a time-of-flight (TOF) of an ultrasound pulse that have passed from transmitting surface 424A (assembly 300A) and receiving surface 424B (assembly 300B) The inventors have found that the absolute value of the TOF can be used as a sensitive indicator of attachment, whereas the change in TOF, $\Delta$TOF, can provide a sensitive and reliable indication of the deep tissue temperature. TOF measurement may involve, for example, transmission of half-period pulses of 2 MHz ultrasound radiation (i.e., 250 ns pulse duration) from first ultrasound transducer 300A and detection of the respective pulses with second opposing ultrasound transducer 300B located directly opposite from the first ultrasound transducer to obtain the time of flight (TOF) of the single ultrasound pulse through the biological tissue.

Figure 5A:
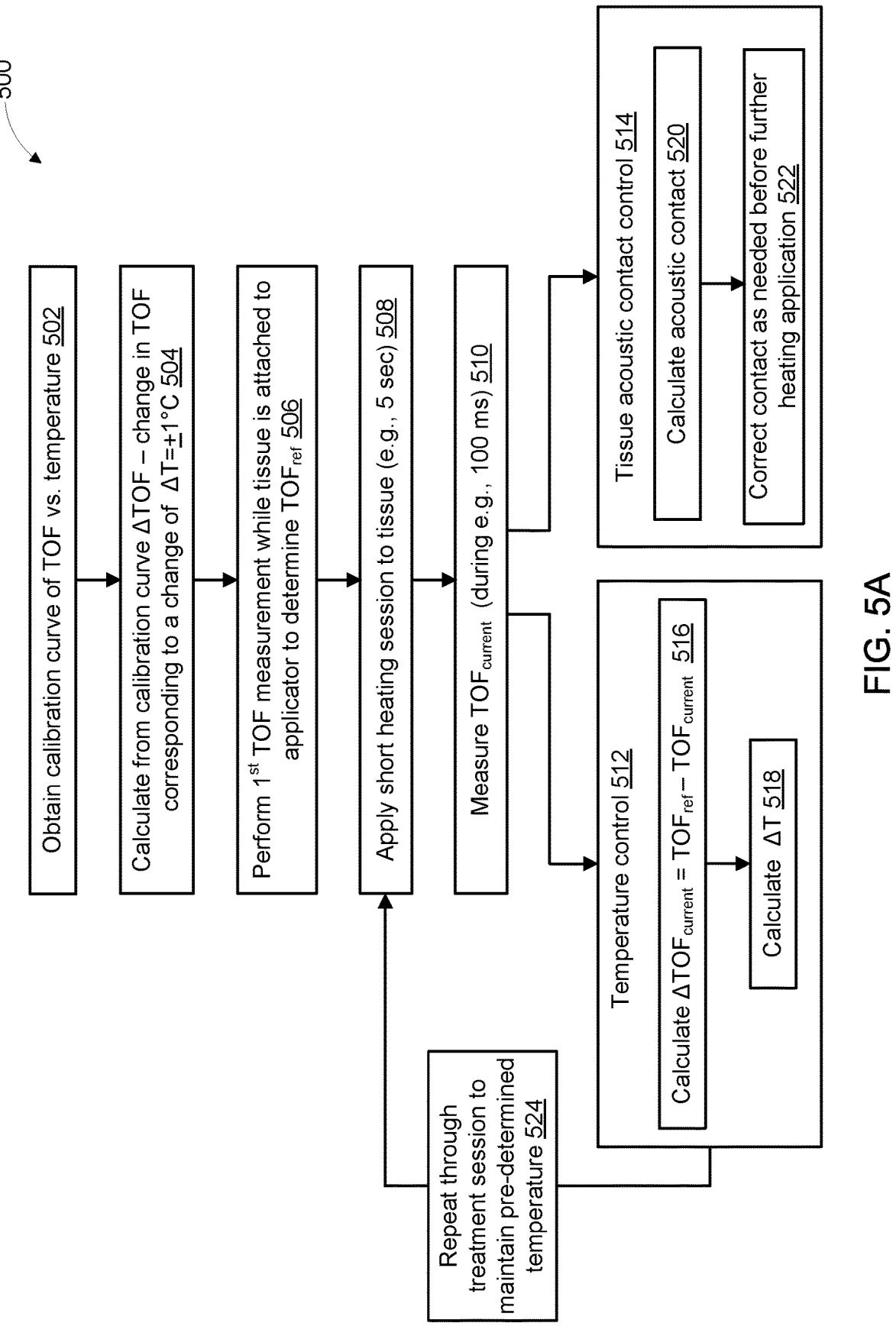
FIG. 5A exemplifies, by way of a flow diagram, the principles of temperature and acoustic contact control technique implemented in the device of the present invention.

Reference is now made to FIG. 5A illustrating, by way of a flow diagram 500, the principles of temperature and acoustic contact level control technique of the present invention. Before the commencement of the treatment session, a calibration stage is performed. This includes provision of a calibration curve (step 502) showing the dependence of TOF of ultrasound radiation at the preferred/operative ultrasound frequency through certain medium on the temperature of said medium.

Figure 5B:
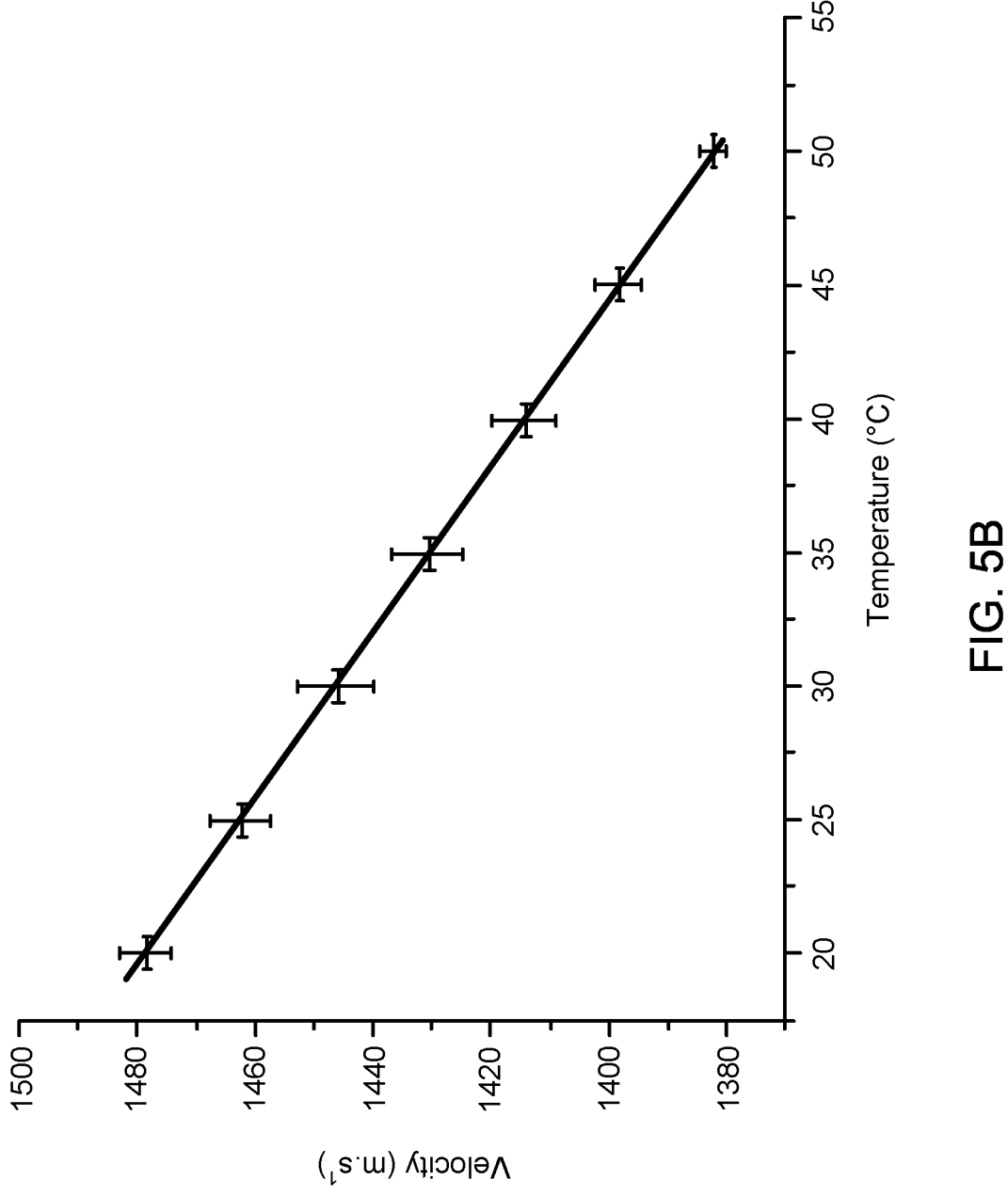
FIG. 5B exemplifies a calibration curve describing tissue temperature change as a function of ultrasound velocity in the tissue, that can be used to determine the temperature from measured time-of-flight of the ultrasound radiation through the tissue.

To determine the tissue temperature, the initial time-of-flight $TOF_0$ and initial temperature. To are to be known. As known in the art, the initial temperature. To is about 35° C. For further calculations, the value of $\Delta v/\Delta T$ m/sec/degree constant for adipose tissue is used. The respective values are also known in the art. Utilizing these known data and measured time-of-flight TOF obtained during the treatment, the tissue temperature as a function of time can be determined. The calibration curve provides $\Delta TOF_{calib}$ defined as the change in TOF corresponding to a change in tissue temperature, $\Delta T$, of ±1° C. (step 504). For example, in some embodiments $\Delta TOF_{calib}$=40 ns was measured. FIG. 5B illustrates a calibration curve, i.e. a graph of tissue temperature change as function of the velocity of ultrasound radiation propagation through tissue. The time-of-flight is 1/velocity.

Yet before applying any heating/treatment to the tissue, the tissue is engaged in the applicator and properly attached to the respective interface regions 118 by, e.g., applying vacuum through vacuum elements as described above. A first TOF measurement is then performed (step 506) serving (i) to ensure good (of a desired degree) contact between biological tissue and the interface region at least within its portion relating to the locations of the ultrasound assemblies and (ii) to provide a reference value of TOF, $TOF_{ref}$ to be used for the temperature measurements. This step can be performed, e.g., by setting ultrasound transceiver 300A of FIG. 4C in the transmit mode and ultrasound transceiver 300B of FIG. 4C in the receive mode.

The TOF measurements happen between each pair of opposite piezo elements, e.g. 320AA↔320BA, 320AB↔320BB (as per FIG. 3E).

It should be noted that the value of $TOF_{ref}$ is to be registered only after ensuring the good contact between the tissue and applicator. Once $TOF_{ref}$ is determined, treatment session (heating by ultrasound radiation) can be started. The treatment session is implemented with a predefined time pattern of alternating tissue treatment intervals of the treatment session (transmission of ultrasound radiation heating the region of interest) and intervals of the control session aimed at temperature control and including detection of the transmitted ultrasound radiation passed through the tissue region and generation of the measured data indicative thereof. The treatment session may be performed in short intervals (e.g., 5 sec) of ultrasound radiation (step 508).

This step can be performed, e.g., by re-setting operational parameters of the ultrasound transceiver 300A or 300B to periodical operation in the transmit mode. In between these intervals, the current TOF, $TOF_{current}$, is measured (based on ultrasound radiation received by the opposing transducer assembly 300B or 300A) during even shorter (e.g., 100 ms) control intervals (step 510). The measured $TOF_{current}$ is utilized for (i) tissue acoustic contact control (step 514) by calculating the acoustic contact (step 520) from the absolute value of $TOF_{current}$ and possibly selectively correcting the contact/attachment as needed before further heating application (step 522) and (ii) temperature control (step 512) where $TOF_{current}$ is used to calculate the change in TOF (step 516), from which (based on the calibration curve) the change in tissue temperature is extracted (step 518). The steps 508 to 514 are repeated through all the duration of each treatment to maintain, in real time, a pre-determined temperature of the biological tissue (step 524).

If the average temperature of biological tissue (i.e. as measured for example by ultrasound time-of-flight) is below a desired value (e.g. a set-point minimum of at least 45° C. or of at least 46° C. or at least 47° C. or at least 48° C.), controller 122 (its control circuitry 126) may, for example, respond by causing ultrasound transducer assembly 300A and/or 300B to increase a power level and/or duty cycle. Conversely, if the average temperature is measured to be above a desired value, the respective control circuitry may for example respond by causing ultrasound transducer assembly 300A and/or 300B to decrease a power level and/or duty cycle.

It should be emphasized that such real time effective and practically continuous temperature control during the tissue treatment is provided by the applicator configuration including at least one opposing pair of directional ultrasound transceivers.

Figures 5C, 5D:
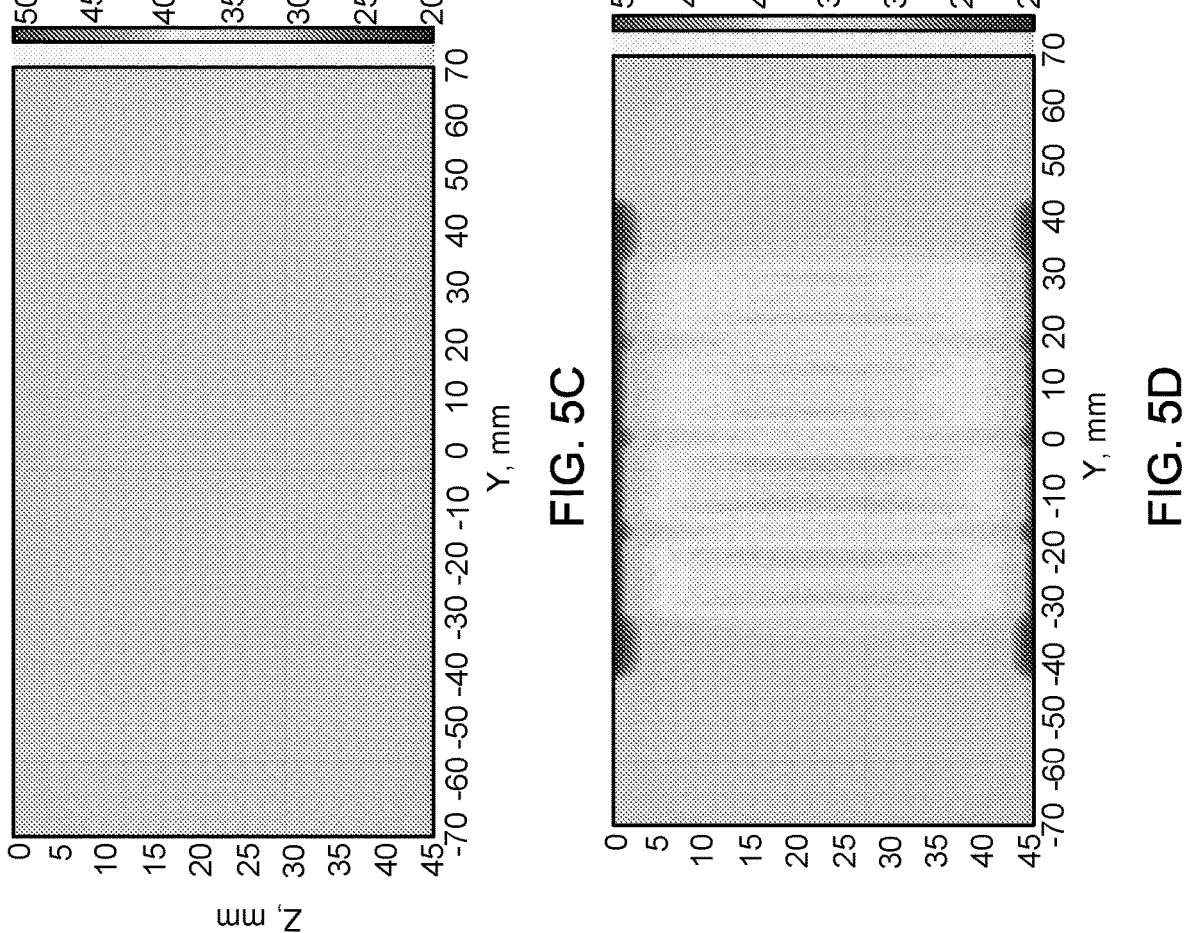
FIGS. 5C-5I present results of simulations conducted by the inventors showing the tissue heating profile at several time points throughout the simulated procedure, and heating temp. profile at different depths of fatty layer.
Figures 5E, 5F:
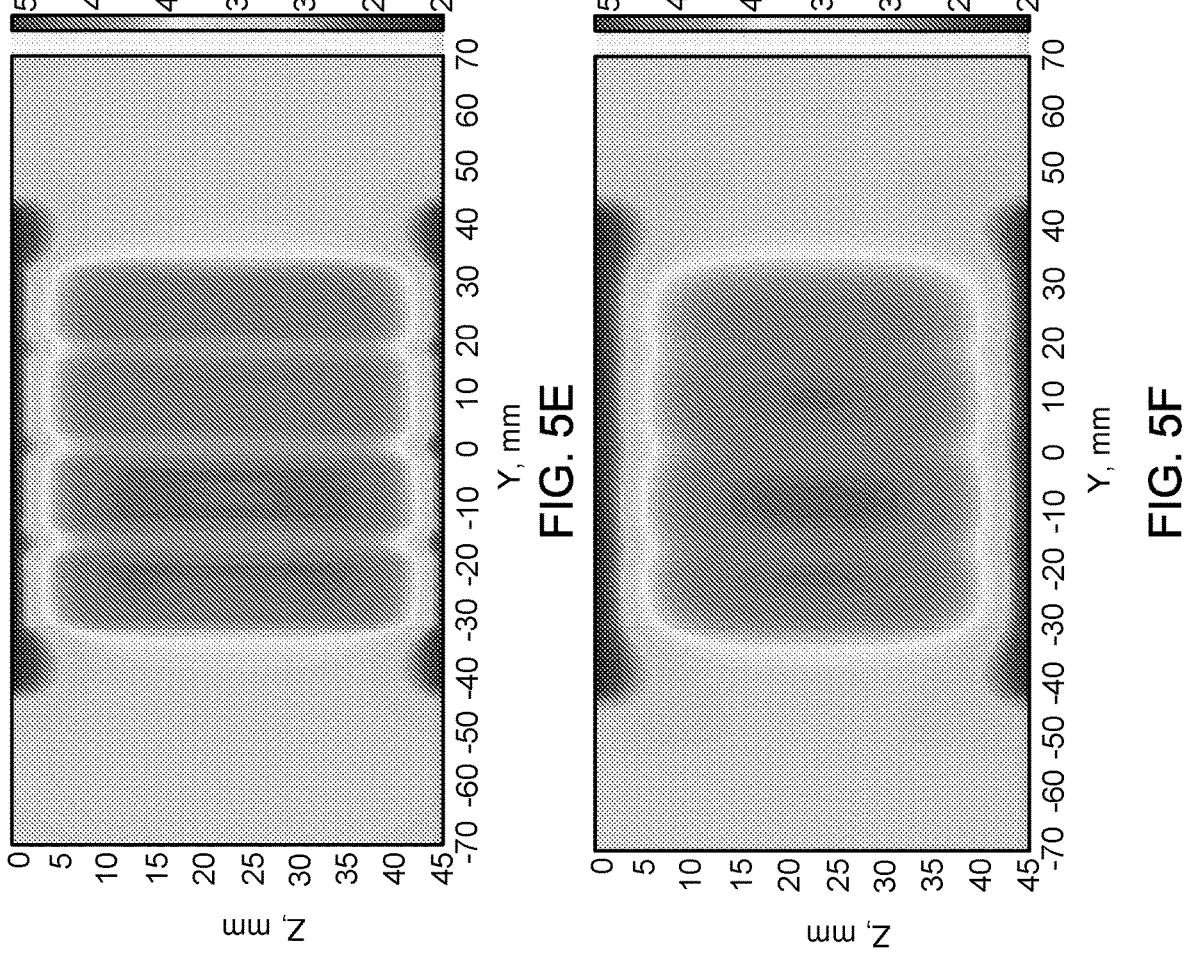
Figures 5G, 5H:
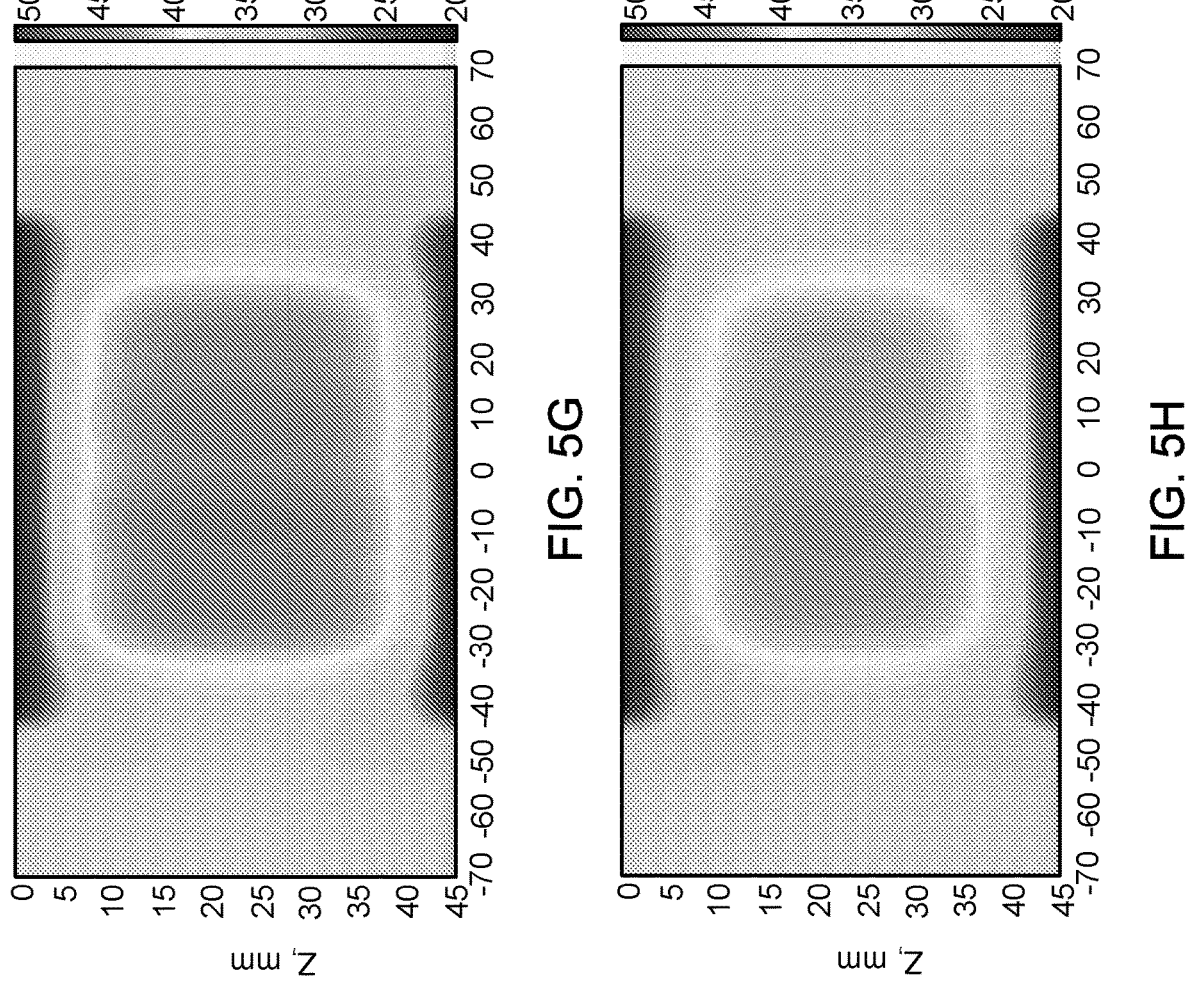
Figure 5I:
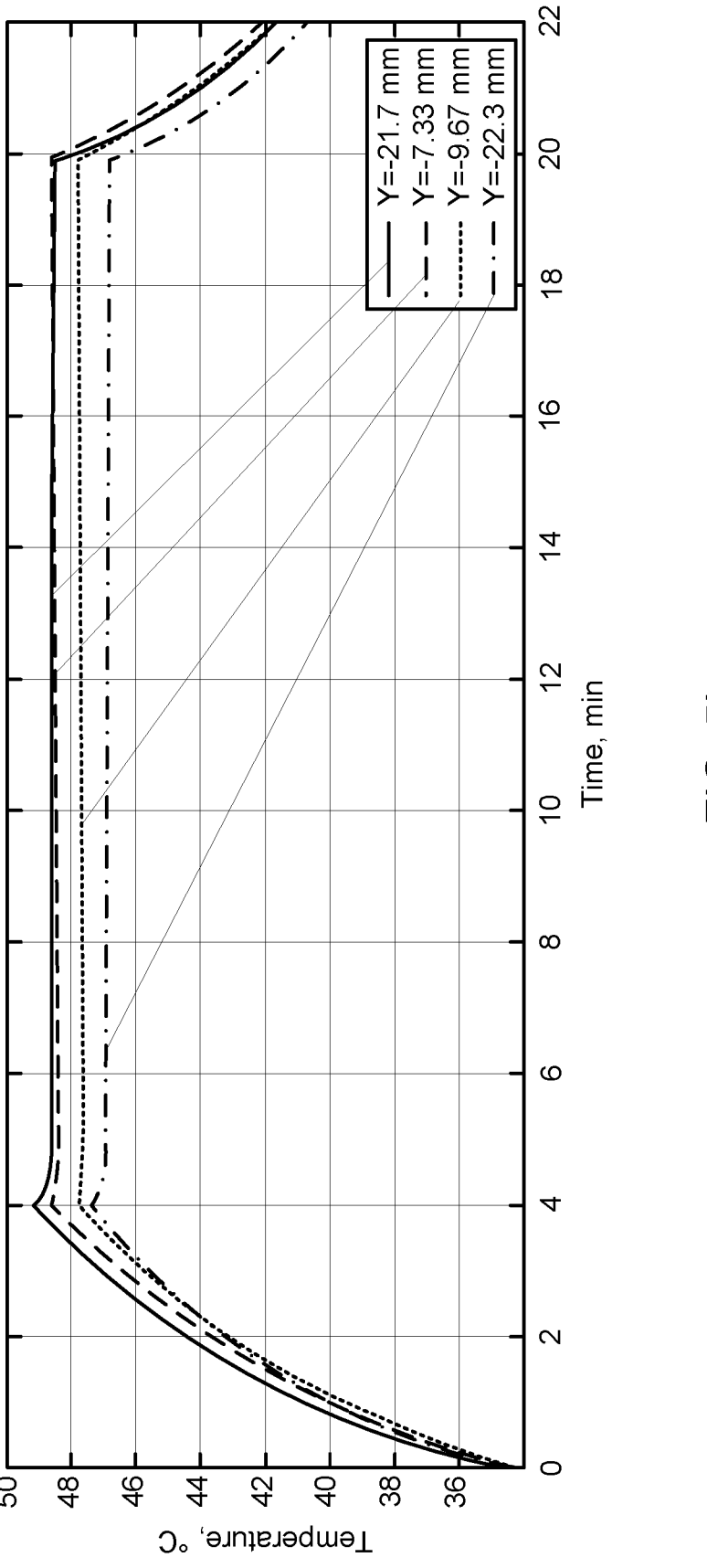

FIGS. 5C-5I present results of simulations conducted by the inventors showing the tissue heating profile at several time points throughout the simulated procedure. Each of these figure shows the temperature patterns of a piezoelectric dermal layer and fatty layer at each point in time. More specifically, FIG. 5C shows the temperature pattern before the heating start; FIG. 5D shows the temperature pattern after 1 minute of heating (temperature of dermal layer is 25-35° C., temperature of fatty layer is 37-43° C.); FIG. 5E-after 4 min of heating (temperatures of dermal layer and fatty layer are respectively 25-35° C. and 45-48° C.; FIG. 5F—after 10 min of heating (temperatures of dermal layer and fatty layer are respectively, 25-35° C. and 45-48° C.; FIG. 5G—after 20 min of heating (temperatures of dermal layer and fatty layer are respectively, 25-30° C. and 44-47° C.; and FIG. 5H—after 1 min of stop heating (temperatures of dermal layer and fatty layer are respectively 25-27° C. and 42-44° C. FIG. 5I illustrates the heating temperature profile at different depths of fatty layer. Thus, as shown, after 20 minutes of transmission of ultrasound radiation, the fatty layer reaches a temperature of approximately 47-49° C. and the skin temperature is kept up to 35° C.

In the following, more specific and detailed treatment protocols utilizing the applicator of the present invention will be described.

Figure 6B:
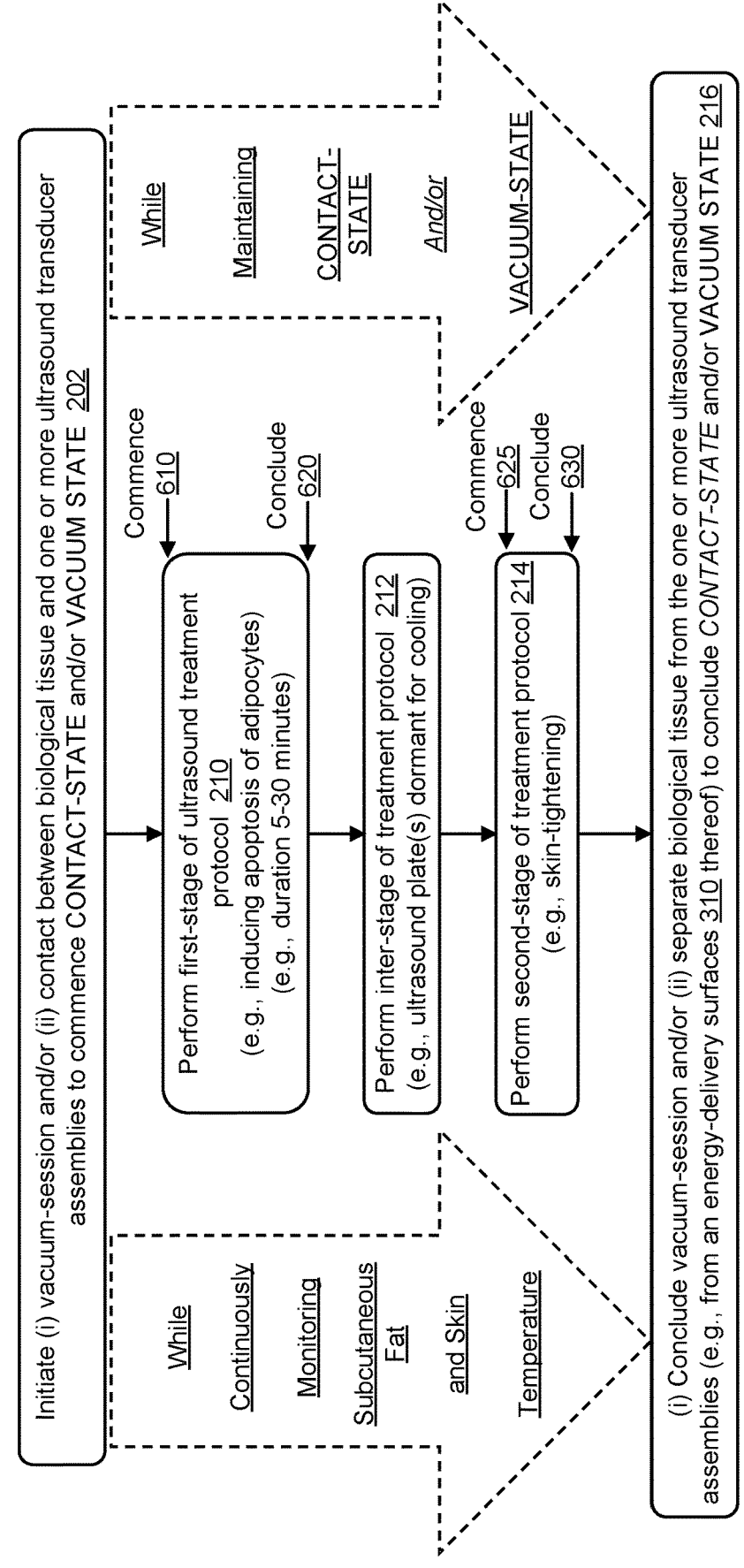
Figure 6C:
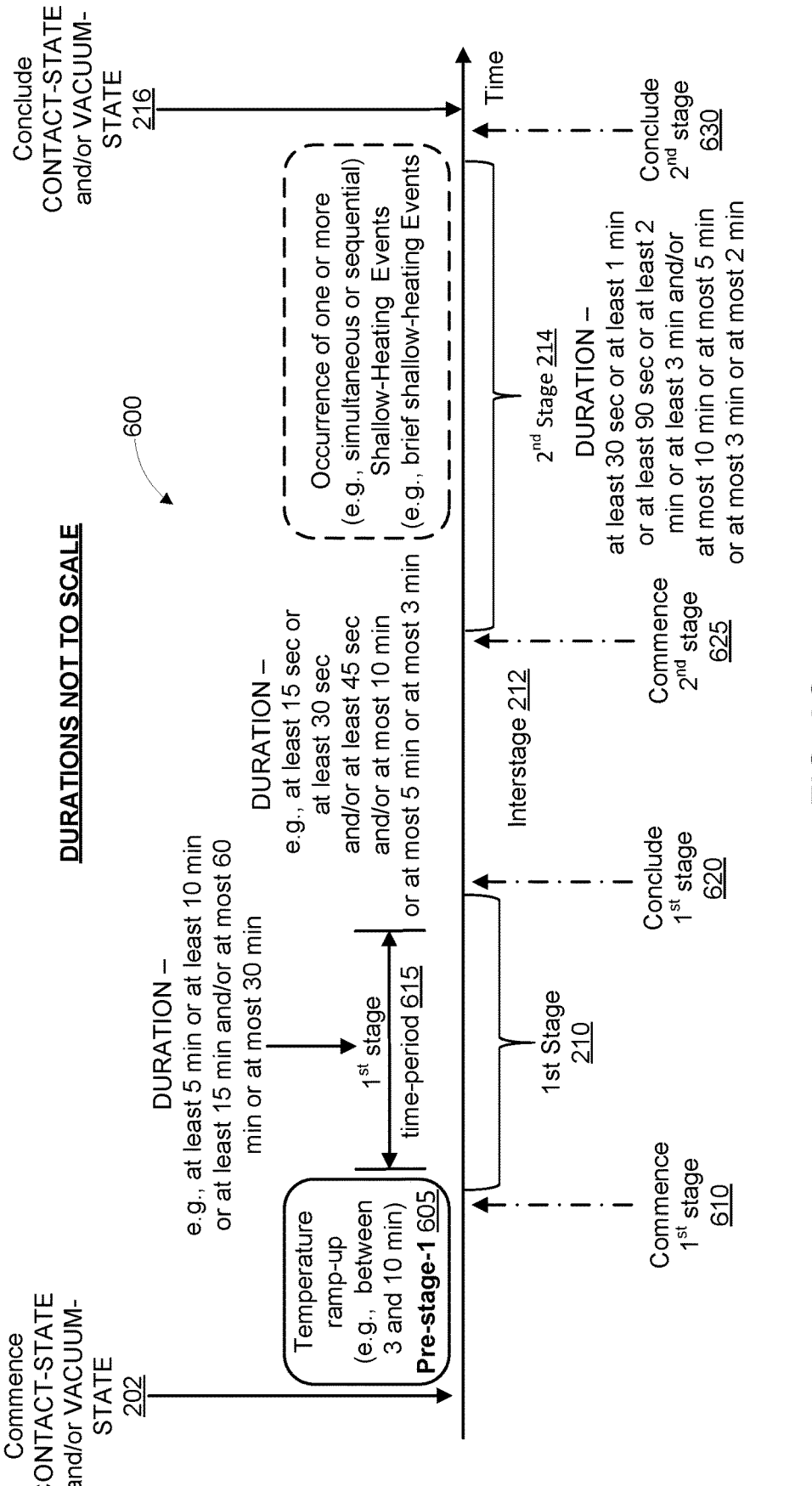

FIGS. 6A to 6C exemplify flow diagrams 600 of exemplary embodiments of ultrasound treatment of biological tissue using the device of the present invention based on the already described above general technique (flow diagram 200 of FIG. 2). In particular, in this non limiting example, method 600 is a 'hybrid method' where the biological tissue is subjected to both: (i) a first treatment stage 210 for damaging adipocytes (e.g., inducing apoptosis thereof) and (ii) a second treatment stage 214 for skin-tightening.

Subsequent to the first treatment stage 210 and before commencement of the second treatment stage 214, the biological tissue may be subjected to an inter-stage 212 of the multi-stage treatment protocol. In embodiments of the invention, the treatment protocol exemplified in FIGS. 6A to 6C is carried out by applicator 102 that remains stationary during an entire time period, ETP, which (a) begins concurrently with or before the commencing step 610 of the first stage 210; and (a) ends concurrently with or subsequent to conclusion step 630 of the second-stage 214. Alternatively or additionally, one or more other features of ETP may be provided.

Alternatively or additionally, in embodiments of the invention, the treatment protocol of FIG. 6A is carried out so that a specific part of skin portion 160 remains in contact with an energy-delivery (transceiving) surface of any ultrasound transducer assembly (e.g. a surface of a plate-like element 330P of any ultrasound transducer assembly) during the aforementioned ETP.

Alternatively or additionally, in embodiments of the invention, the treatment protocol of FIG. 6A is carried out during a 'single continuous vacuum session' which is continuous during the entire ETP so that at least a portion of the biological tissue is continuously subjected to vacuum and/or suction and/or negative pressure (e.g., to urge the at least a single portion of biological tissue towards a surface of at least one of the ultrasound transducer assemblies during the entire ETP).

As stated above, the first stage 210 may be aimed at damaging adipocytes and/or inducing apoptosis thereof. In FIGS. 6A to 6C, the commencement of first stage 210 is labelled as 610, and the conclusion of first stage 210 is labelled as 620.

It should be noted that the example of FIG. 6B includes the steps of example of FIG. 6A and additional steps 202 and 216. In step 202, a contact and/or vacuum state is initiated, and this contact-state and/or vacuum state is maintained throughout the method until step 216 which occurs after conclusion step 630) when biological tissue is disengaged from applicator 102.

The CONTACT-STATE which is maintained (i.e. throughout the time period beginning at commence step 610 and ending at conclusion step 630) may include any combination of the following: (i) contact between interface region or its part at the energy-delivery surface (transceiving surface) 310 of transducer assembly 300A and an upper surface of skin portion 160 of biological tissue; and/or (ii) contact between interface region or its part at the energy-delivery surface 310 of transducer assembly 300B and an upper surface of skin portion 160 of biological tissue; and/or (iii) contact between interface region or its part at the energy-delivery surface 310 of transducer assembly 300C and an upper surface of skin portion 160 of biological tissue. In embodiments of the invention, the CONTACT-STATE includes pressure (e.g., 'outward pressure' for example driven by suction or negative pressure, for example maintained throughout an entirety of the time-period of the CONTACT-STATE) applied by the biological tissue upon (i) a part of the interface region at surface 310 of transducer assembly 300A and/or (ii) a part of the interface region at surface 310 of transducer assembly 300B; (iii) a part of the interface region at surface 310 of transducer assembly 300C.

The VACUUM-STATE which is maintained (i.e., throughout the time period beginning at commence step 610 and ending at conclusion step 630) may include negative pressure supplied upon an upper surface of skin portion 160 via respective part of the interface region, for example, at a location corresponding to a surface of transducer assembly 300A and/or transducer assembly 300B and/or transducer assembly 300C.

In embodiments of the invention, an elapsed time between commence step 610 and conclusion step 630 is at least 7 minutes or at least 10 minutes or at least 15 minutes or at least 20 minutes. This might be the duration of the CONTACT-STATE or the VACUUM-STATE.

Because CONTACT-STATE (and/or VACUUM-STATE) is continuously maintained throughout a time-period commencing no later than step 610 and concluding no earlier than step 630, this is an example of "tissue-engaged time-period" when a volume (i.e., at least a portion thereof) of biological tissue is to be kept engaged to the transceiving surfaces of transducer assembly 300A and transducer assembly 300B and possibly also transducer assembly 300C.

As was already noted above, the example of FIGS. 6A-6C may relate to a 'hybrid' technique for both damaging adipocytes (i.e., stage 210) and skin-tightening (i.e., stage 214). In other embodiments, the stage 210 might not be required, and the inventive method may relate to providing skin-tightening from multiple-directions (i.e. at least two or at least three directions) during a "tissue-engaged time-period" (e.g. continuously maintaining CONTACT-STATE and/or VACUUM-STATE throughout) which commences no later than commence step 625 of stage 214 and concludes no early than conclude step 630 of stage 214 (e.g. having a duration of at least 1 minute or at least 2 minutes or at least 3 minutes).

For any embodiment, a "tissue-engaged time period" (i.e., including at least an entirety of stage 210 and/or including at least an entirety of stage 214 and/or including both of stages 210 and 214) may have a duration of at least 3 minutes or at least 5 minutes of at least 7 minutes of at least 10 minutes or at least 15 minutes.

In some embodiments, a duration of the first stage 210 is at least 5 minutes or at least 7 minutes or at least 8 minutes or at least 10 minutes or at least 12 minutes or at least 13 minutes or at least 15 minutes. In some embodiments, a duration of the first stage 210 is at most 30 minutes or at most 25 or at most 30 minutes.

A first stage-time period 615 (FIG. 6C) may occur during the first stage treatment protocol 210. The duration of the first stage time period may be, for example, between 20% and 100% of the duration of the first stage 210. In some embodiments, a duration of the first stage time-period 615 is at least 5 minutes or at least 7 minutes or at least 8 minutes or at least 10 minutes or at least 12 minutes or at least 13 minutes or at least 15 minutes. In some embodiments, a duration of the first stage time-period 615 is at most 30 minutes or at most 25 or at most 30 minutes. As also shown in FIG. 6C, a pre-stage-1 605 may be performed, aimed at gradually increasing the tissue temperature during 3-10 minutes.

It should be noted (see arrow on the left of FIG. 6B) that during the whole duration of the treatment session process 600 the temperature of the subcutaneous fat and skin portions of the tissue are monitored in real time using the methods described above (e.g., with reference to FIG. 5) to guarantee a predetermined temperature distribution/profile/ pattern. A more detailed protocol of temperature monitoring will be detailed further below.

As described above, the second stage 214 may be for skin tightening. As shown in FIGS. 6A-6C, the commencement of second stage 214 is labelled as 625, and the conclusion of second stage 214 is labelled as 630.

In some embodiments, a duration of the second stage 214 is at least 1 minute or at least 2 minutes or at least 3 minutes or at least 5 minutes or at least 7 minutes or at least 10 minutes or at least 15 minutes. In some embodiments, a duration of the first stage 210 is at most 15 minutes or at most 10 or at most 7 minutes or at most 5 minutes or at most 3 minutes or at most 2 minutes.

During the second stage 214, one or more brief shallow-heating events may be provided by one or more of trans-ducer assemblies 300A, 300B and 300C. Nevertheless, outside the time periods of these brief shallow-heating events, the second stage may be characterized by a lack of ultrasound heating and/or contact cooling.

The period of time after the conclusion step 620 of the first stage 210 and before the commencement step 625 of the second stage 214 is referred to as the interstage 212, and a duration thereof may be at least 30 seconds or at least 1 minute or at least 3 minutes or at least 5 minutes or at least 7 minutes. A duration of the interstage 212 may be at most 10 minutes or at most 7 minutes or at most 5 minutes or at most 3 minutes.

For example, during the interstage, contact cooling may be provided without ultrasound heating to allow the biologi-cal tissue in the central region to be cooled and/or to 'rest' after conclusion of the first stage 210 (for damaging adipocytes by ultrasound heating) and before commencement of the second stage 214 (for skin tightening by ultrasound heating).

It should be noted that variations of FIG. 6A-6C, where one or more of the steps are not performed, or where one or more of the steps are modified, or wherein a modified applicator 102 (e.g., not including transducer assembly 300C and/or inner wall 424C), are also in the scope of the present disclosure.

Figure 7A:
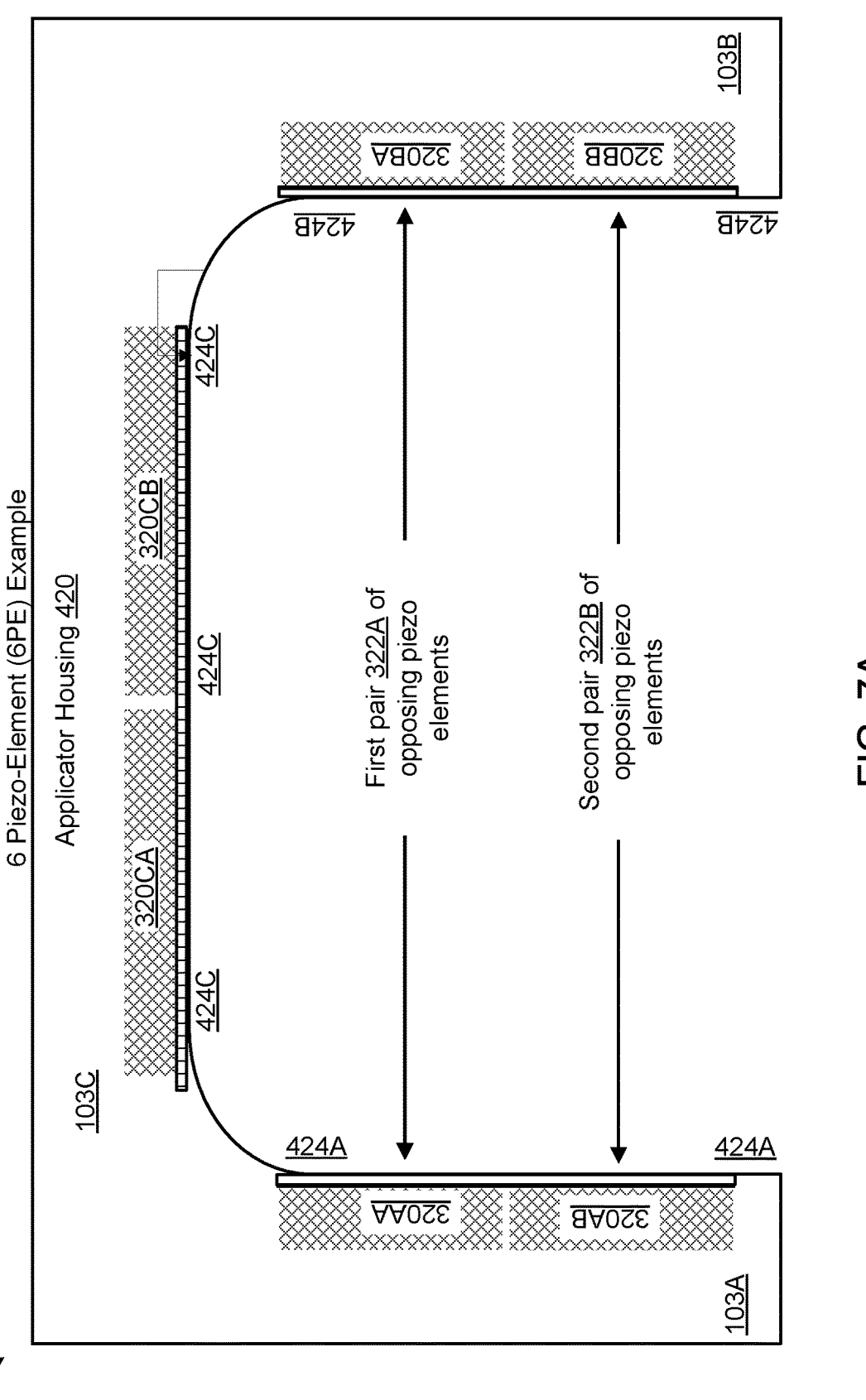
FIGS. 7A to 7B illustrate the configuration and operation of exemplary transducer arrangements, where
Figure 7B:
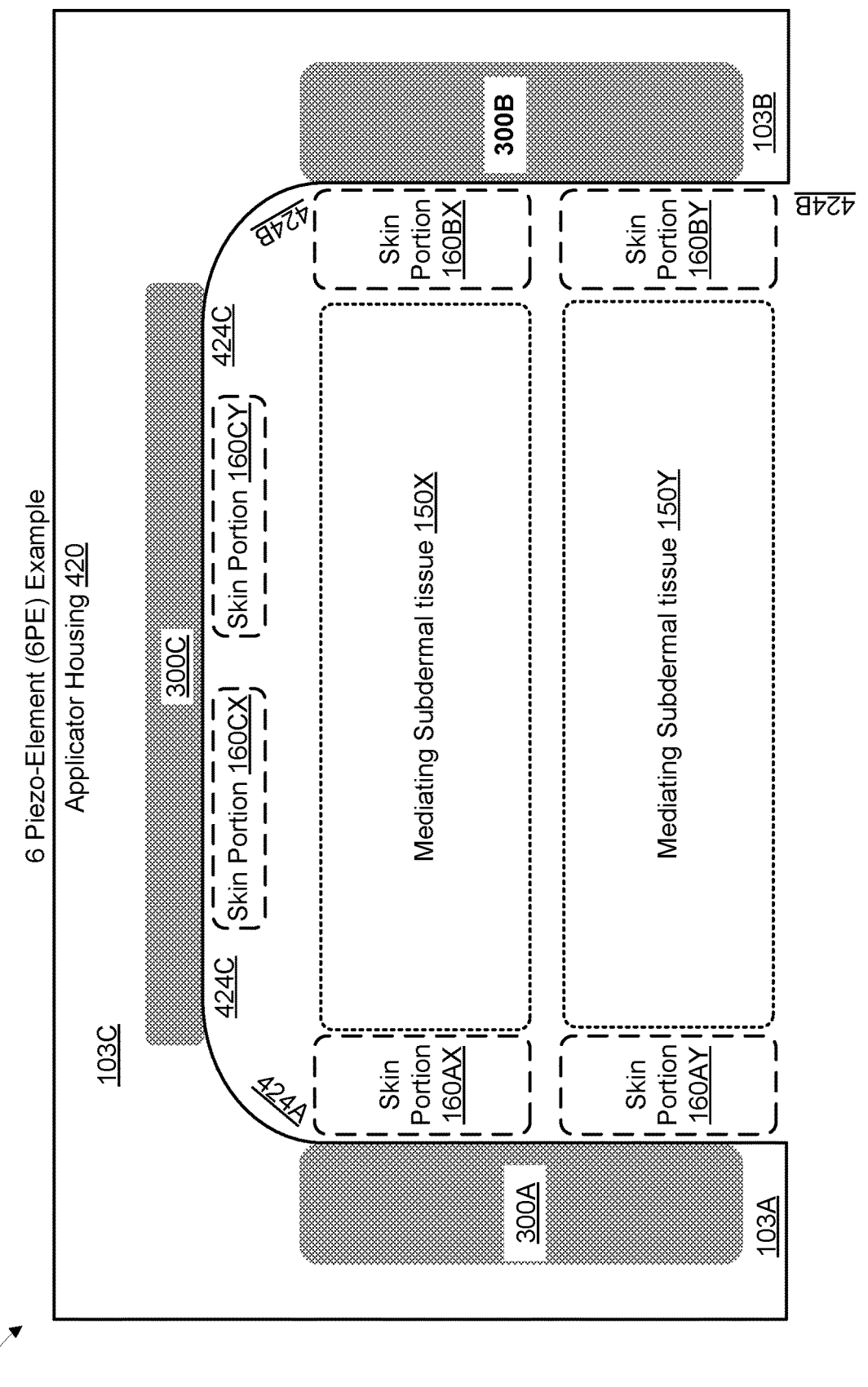

Reference is now made to FIGS. 7A-7B. FIG. 7A shows a non-limiting example of the embodiment where the trans-ducer assemblies (at least the opposing directional trans-ducer assemblies) of the transducer arrangement are multi-element assemblies, i.e. each transceiving surface of the assembly defines an array of spaced-apart transceiving seg-ments. Typically, this is implemented by configuring the transducer assembly from multiple (generally at least two) transducer elements. By this, the transducer arrangement defines at least two pairs of opposing directional transducer elements.

In the specific example of FIG. 7A, the transducer arrangement 104 has 6 piezo-element (6E) transducer con-figuration. This transducer arrangement presents one pos-sible non-limiting example suitable to implement the above-described technique of the invention (e.g. methods of FIGS. 6A to 6C).

The ultrasound transducer arrangement includes two opposing transducer assemblies 300A and 300B, and pref-erably also intermediate transducer assembly 300C each including two piezoelectric transducer elements: ultrasound transducer assembly 300A includes piezoelectric transducer elements 320AA and 320AB; ultrasound transducer assem-bly 300B includes piezoelectric transducer elements 320BA and 320BB; and ultrasound transducer assembly 300C includes piezoelectric transducer elements 320CA and 320CB.

As shown in FIG. 7A, the exemplary applicator provides two pairs of opposing piezo transducer elements: a first pair 322A of "opposing" piezoelectric transducer elements 320AA and 320BA, and a second pair 322B of "opposing" piezoelectric transducer elements 320AB and 320BB. As illustrated in FIG. 7B, such transducer assemblies 300A and 300B provide that skin portions 160AX, 160BX as well as subdermal tissue 150X are disposed in the region between piezoelectric transducer elements 320AA and 320BA of the first opposing pair 322A of piezo transducer elements; and skin portions 160AY and 160BY as well as subdermal tissue 150Y are disposed in the region between piezoelectric transducer elements 320AB and 320BB of the second opposing pair 322Y of piezo transducer elements.

The first treatment stage 210 is explained below for the specific example applicator of FIGS. 7A and 7B.

In some embodiments, during first stage time-period 615 (e.g., during a majority of every 30 sec sub-window thereof), opposing ultrasound transducer assemblies 300A and 300B (FIG. 7B) simultaneously irradiate the biological tissue (e.g., at least most of, or all of the mediating subdermal tissue 150) that is disposed between the substantially parallel plates (plate like elements 310) defined by the ultrasound assem-blies 300A and 300B with unfocused CW ultrasound of e.g. [1 MHz, 4 MHz].

For example, each of the "opposing" piezoelectric trans-ducer elements of the pair of such elements (e.g., 320AA-320BA of the pair 322A in FIG. 7A) may be controllably operated to simultaneously irradiate mediating biological tissue (e.g., at least mediating subdermal tissue 150X) with unfocused directional ultrasound radiation, e.g. CW ultrasound of [1 MHz, 4 MHz]. More specifically, piezoelectric transducer element 320AA may transmit unfocused CW ultrasound (i.e., via the associated plate-like element 330P of transducer assembly 300A) at a frequency freq_320AA in a first direction (i.e., from left to right in FIGS. 7A-7B), thereby heating mediating biological tissue (e.g., at least mediating subdermal tissue 150X) disposed between piezoelectric transducer elements 320AA and 320BA. Simultaneous therewith, piezoelectric transducer element 320BA may transmit unfocused CW ultrasound (i.e., via the associated plate-like element 330P of transducer assembly 300B) at a frequency freq_320BA in a second direction (i.e., from right to left in FIGS. 7A-7B) along substantially coinciding axis with that of the directional transmission of transducer element 320AA that thereby opposes the first direction, and heating mediating biological tissue (e.g., at least mediating subdermal tissue 150X) disposed between piezoelectric transducer elements 320AA and 320BA.

The frequencies may be equal, e.g., freq_320AA=freq_320BA. For example, freq_320AA=freq_320BA=1.5 MHz. For example, freq_320AA=freq_320BA=2.0 MHz. For example, freq_320AA=freq_320BA=2.5 MHz. For example, freq_320AA=freq_320BA=3.0 MHz. For example, freq_320AA=freq_320BA=3.5 MHz. For example, freq_320AA=freq_320BA=4.0 MHz.

Preferably, however, the frequencies are slightly different, i.e. are so-called "nearly equal frequencies, freq_320AA≈freq_320BA. This is aimed at avoiding or at least significantly reduce standing wave effect.

For example, freq_320AA≈1.5 MHz and freq_320AA≈1.5 MHz, or freq_320AA≈2 MHz and freq_320BA≈2 Mhz, or freq_320AA≈2.5 MHz and freq_320BA≈2.5 MHz, or freq_320AA≈3 MHz and freq_320BA≈3 MHz. or freq_320AA≈3.5 MHz and freq_320BA≈3.5 MHz, or freq_320AA≈4 MHz and freq_320BA≈4 MHz.

The term 'nearly equal frequencies' may be discussed in terms of max (freq_320AA, freq_320BA)) which is a greater of freq_320AA and freq_320BA. Alternatively, this term may be discussed as an absolute value of a difference between the frequencies freq_320AA and freq_320BA. Generally, the frequencies may differ from one another by 0.5%-20%. For example, they may differ by at least 1% or at least 2% or at least 3% or at least 4% or at least 5% or at least 6% at least 7% or at least 8% or at least 9% or at least 10% of a greater of max(freq_320AA, freq_320BA)); and/or they may differ by at most 20% or at most 15% or at most 10% or at most 8% or at most 6% of max(freq_320AA, freq_320BA)).

It should be noted that the use of 'nearly equal frequencies' during the first treatment stage 210 provides for homogenous heating of the mediating subdermal tissue by avoiding creation of standing waves inside the tissue. Standing waves may be formed in the tissue when equal frequencies are emitted by the two opposing piezoelectric transducer elements, e.g., 320AA and 320BA in FIG. 7A, creating thus a particular nodal pattern associated with the particular frequency used. The nodal pattern creates layers of non-uniform temperatures across the mediating subdermal tissue, e.g., subdermal tissue 150X. Such inhomogeneous temperature distribution may harm the achievement of a desired treatment result and should be avoided by using 'nearly equal frequencies'. The operation of the device wherein the first and second transducer assemblies (e.g., 320AA and 320BA in FIG. 7A) are configured and controllably operated to generate the first and second ultrasound radiations of respectively first and second frequencies with a difference between them in a range of 0.5%-20% provides for substantially homogenous temperature along the region of interest during the treatment session.

As was already described above and more specifically exemplified in relation to FIG. 5A, the applicator of the present invention, in particular utilizing multiple pairs of opposing transducer elements, e.g., applicator exemplified in FIGS. 7A to 7B, may be used to perform time-of-flight measurements to measure the amount of time it takes for a pulse of ultrasound radiation to traverse the tissue engaged between the portions of the interface region at the arms of U-shaped applicator (or applicator housing), e.g. walls 424A and 424B.

In one non-limiting example, piezo element 320AA (i.e., of ultrasound transducer assembly 300A) of a first pair 322A of opposing piezo elements of FIG. 7A is configured to transmit an ultrasound pulse which is detected by the other opposing piezo element 320BA (i.e., of ultrasound transducer assembly 300B) of the first pair 322A of opposing piezo elements—or vice versa).

In general, the ultrasonic transmission properties of tissues are known to change with the temperature of the tissue. The speed of sound in non-fatty tissues increases with temperature and exhibits a maximum at around 50° C., while for fatty tissues a negative dependence is observed [Bamber J. C. and Hill C. R., "Ultrasonic attenuation and propagation speed in mammalian tissue as a function of temperature," Ultrasound Med. Biol. 5, 149-157 (1979). 10.1016/0301-5629(79)90083-8]. Therefore, the speed of sound of fatty tissues will actually be decreased with increasing temperature up to about 50° C.

In the present invention, a TOF measurement of ultrasound (e.g., travelling in a longitudinal direction) is used to determine an average temperature of biological tissue disposed between respective forward-facing transceiving surfaces of opposing ultrasound transducer assemblies 300A and 300B as was already described in detail above. In general, a longer TOF (more time is required for a pulse of ultrasound to longitudinally traverse mediating region between the respective paired surfaces of the transducers) indicates that ultrasound travels slower in the tissue (e.g., subdermal adipose tissue 150X), and is thus indicative of hotter biological tissue disposed in mediating region between respective forward-facing opposing surfaces of ultrasound transducer assemblies 300A and 300B, and a shorter TOF indicates that ultrasound travels faster in the biological tissue, and is thus indicative of colder biological tissue disposed in the mediating region between the respective forward-facing opposing surfaces of ultrasound transducer assemblies 300A and 300B. As was already mentioned above, in order to provide an accurate average temperature measurement, the change in the measured TOF (ΔTOF) with respect to the reference value obtained soon after stage 202, and not the absolute value, is used to extract the tissue temperature profile (increase/decrease), as exemplified and described above with reference to FIG. 5A.

Figure 7C:
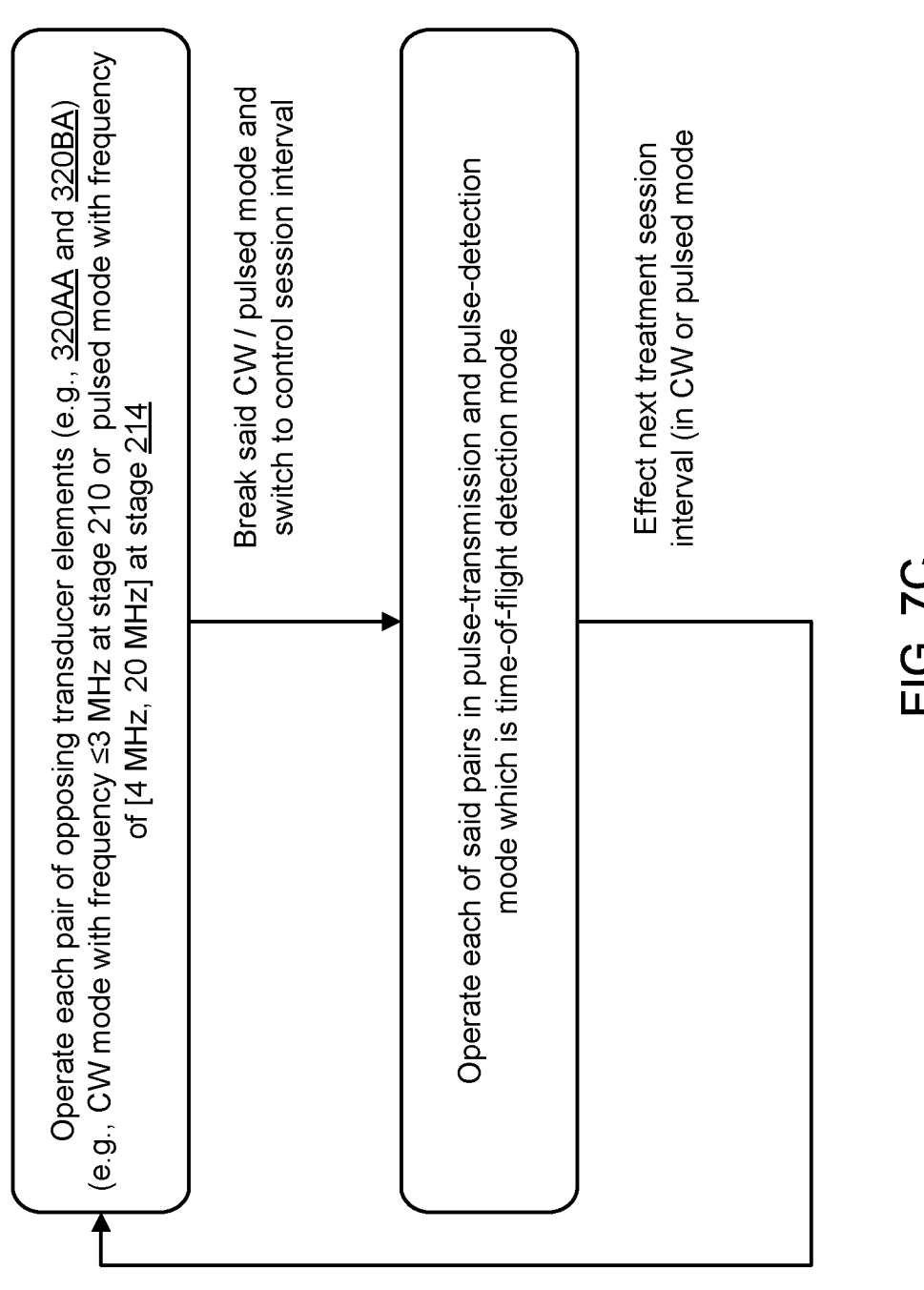
FIG. 7C illustrates the exemplary flow diagram of the operation of such device using opposing pairs of directional transducer elements in the applicator.

FIG. 7C illustrates in a self-explanatory manner the exemplary flow diagram of the device operation described above using opposing pairs of directional transducer elements in the applicator. As shown, each of the opposing pairs of transducer elements operate to implement the interval of treatment session using appropriate CW or pulsed mode and frequencies for deep tissue and shallow tissue treatments, and then switch to the interval of control session in which one of the paired transducer operates in pulsed transmission mode and the other detects the ultrasound radiation enabling determination of the time-of-flight, or change of time-of-flight to determine the temperature and tissue acoustic contact conditions.

The device of the present invention provides for a novel technique to automatically adjust parameters/conditions of the treatment radiation for each and every individual during the treatment session, thus resulting in controlled, safe, and uniform tissue heating by said radiation along the region of interest.

Turning back to FIG. 6C, the first stage time-period 615 of first treatment stage 210 is aimed at treatment of deep region(s) of interest. During this time-period the transducer arrangement is controllably operated with a time pattern of alternating tissue treatment intervals of the treatment session and intervals of the control session.

It should be understood that the entire treatment procedure not necessarily include the second stage, and the time period 615 may correspond to the complete treatment procedure. So, the term "first stage treatment 210" used in the description relating to the alternating intervals of the treatment and control sessions during deep tissue treatment should not be limited to the requirement to be followed by the second stage 214 (tissue tightening).

Thus, the time-period 615 is dividable into a number N (being positive integer) of non-overlapping (successive) intervals {Interval1, interval2 . . . intervalN}. Each interval has a duration of at least 10 seconds (generally, being at most 60 seconds or at most 50 seconds or at most 40 seconds or at most 30 seconds or at most 20 seconds or at most 10 seconds).

For at least a temporal majority (e.g., for at least 60% or at least 70% or at least 80% or at least 90% of) of every i-th interval, $\text{interval}_i$ (1≤i≤N), the first and the second opposing directional ultrasound transducer assemblies 300A and 300B deliver [1 MHz, 4 MHZ] unfocused CW ultrasound towards the respective mediating subdermal regions 150X and/or 150Y (FIG. 7B). During each time slot between two successive intervals, $\text{interval}_i$ and $\text{interval}_{i+1}$, a break of energy delivery in a CW mode of both transducer assemblies 300A and 300B is affected for a certain time interval being the time interval of the control session. Such control session interval may have a duration of about 100 msec. During this short break (interval of the control session), both transducer assemblies operate in a pulsed transmission/detection mode to measure TOF. Such continuous intermittent measurement of TOF provides for continuous monitoring and control of both tissue temperature and tissue acoustic contact.

Figure 7D:
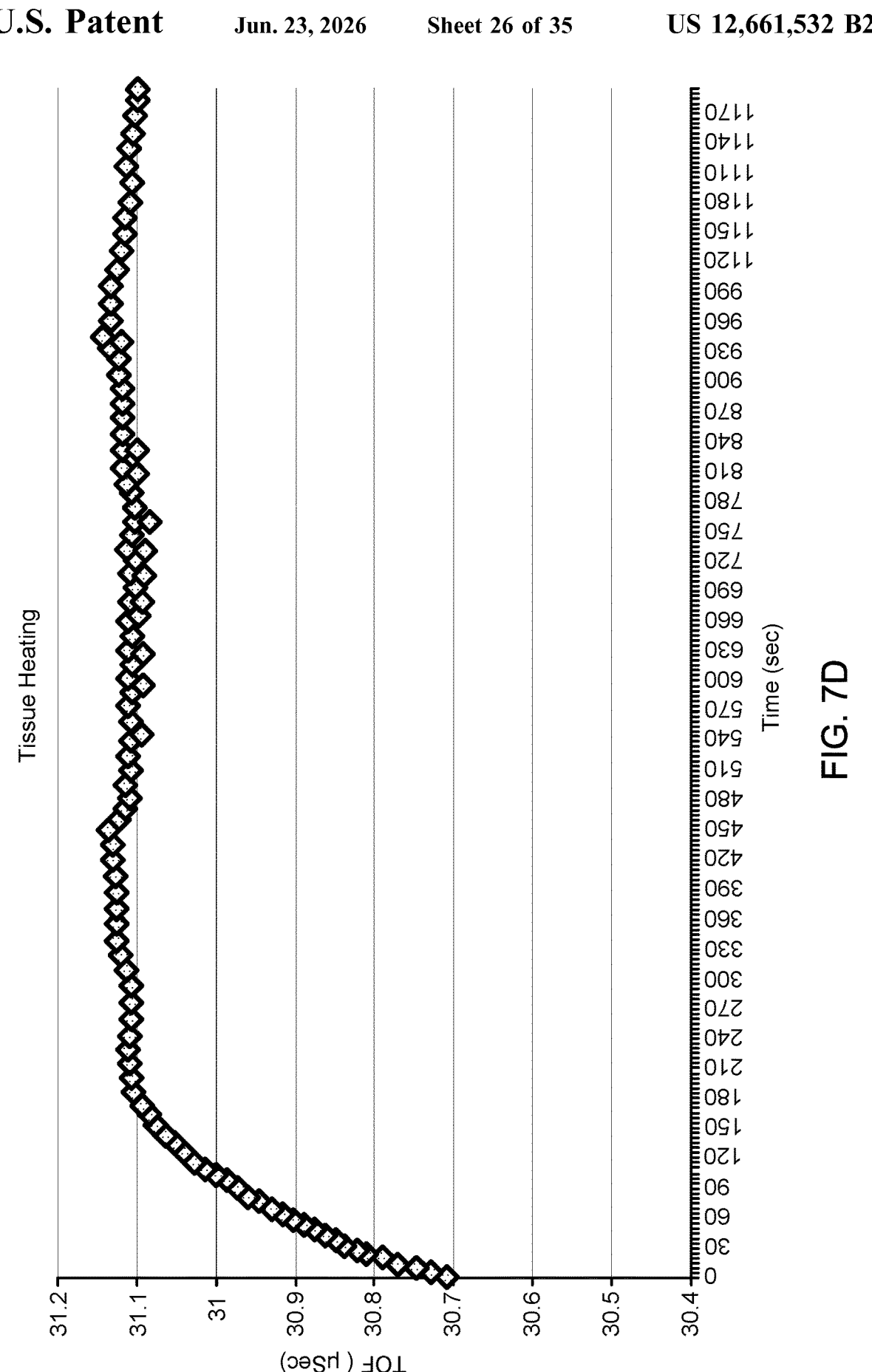
FIGS. 7D and 7E show an example of temperature measurement during heating (treatment session) of a deep adipose tissue using the technique of the present invention.
Figure 7E:
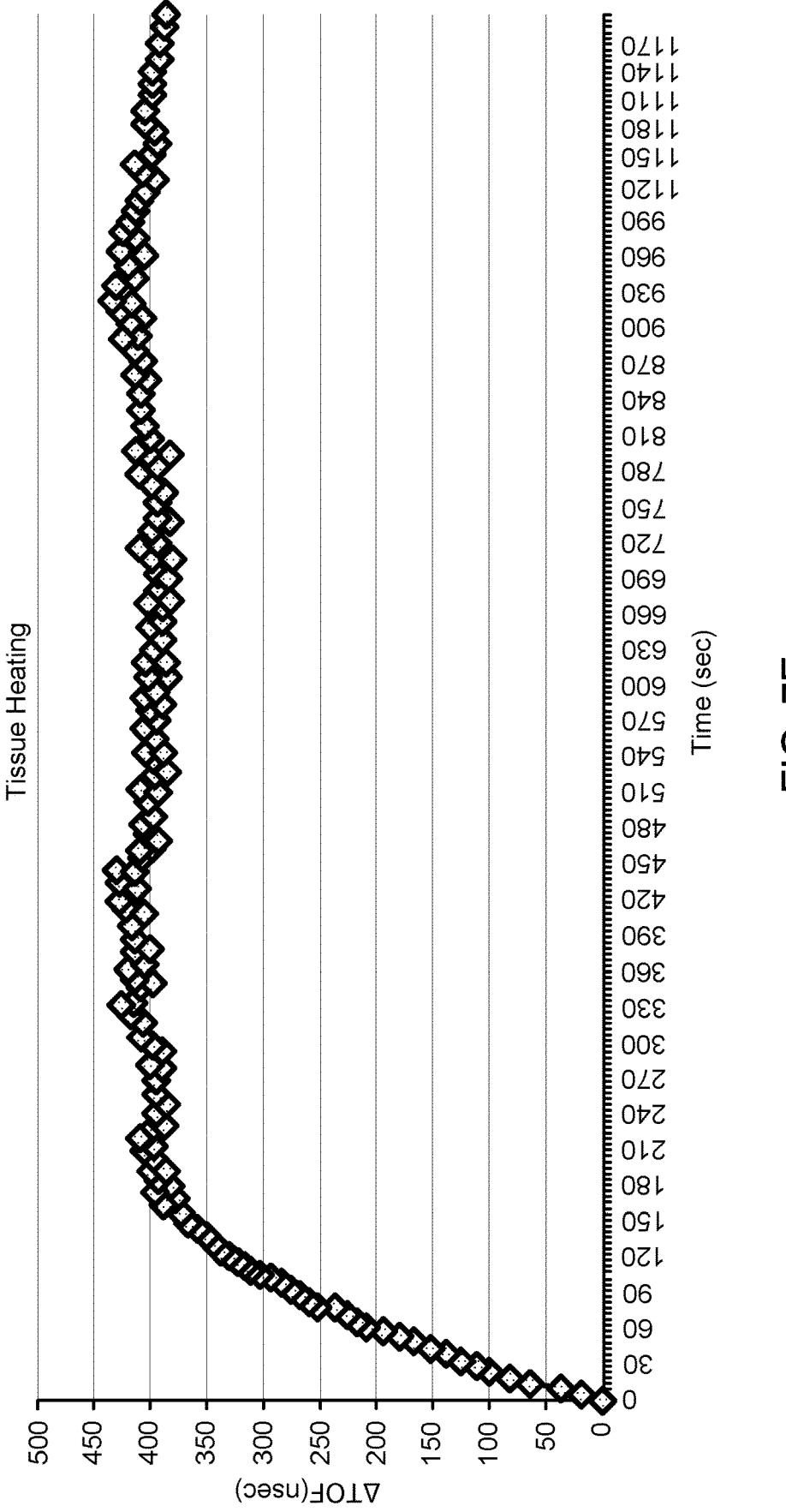

FIGS. 7D and 7E show an example of temperature measurement during heating (treatment session) of a deep adipose tissue using the technique of the present invention. At time zero, a reference TOF parameter, $\text{TOF}_{ref}$, was measured and stored. Therefrom, tissue heating of the first treatment stage 210 started. After each interval of the heating/treatment session (e.g. each and every 5 secs) a break in the CW heating mode was affected and TOF was measured during the relatively short control session interval.

FIG. 7D shows a ramp of increasing TOF over about the first 3 min of heating indicating a ramp of tissue heating. The reference TOF, $\text{TOF}_{ref}$, was used to calculate ΔTOF resulting from each i-th preceding $\text{interval}_i$ of the heating session and to calculate corresponding tissue temperature using the calibration curve. The values of ΔTOF are shown in FIG. 7E. It can be seen that the technique of the invention provides for a constant temperature inside the mediating subdermal tissue all through the length of the treatment (about 20 min).

During the deep tissue treatment session (e.g. first-stage time period 615), transducer piezoelectric elements may operate at or near (i.e., substantially at) a common frequency freq_stage1 whose value is at least 1 MHz and at most 4 MHz (see examples above, explained for the non-limiting case of 320AA and 320BA).

Thus, during the time-period of the deep tissue treatment session (e.g. at least the time-period 615 of the first stage 210), all four piezoelectric (e.g. ceramic) elements (i.e. 320AA, 320BA, 320AB, 320BB) of opposing pairs 322A and 322B of such elements operate simultaneously throughout said time period (or at least for the majority of this time period, e.g. every 30 sec time window), e.g., according to frequency parameters discussed above. For example, each of the piezoelectric elements may transmit ultrasound energy at a density of at least 1 or at least 2 watts/cm$^2$. In contrast, the two piezoelectric (e.g., ceramic) elements (i.e., 320CA and 320CB) of transducer assembly 300C may be dormant throughout the same first stage time-period.

Concurrent with the delivery of ultrasound energy, contact cooling of both ultrasound transducer assemblies 300A and 300B is provided throughout the first time period 615 (or at least for a majority of every 10 second time window within the first time period 615), e.g. for both assemblies the respective skin-contacting surfaces 310 of the transducers are both maintained at a 'low' temperature of at most 30° C., or at most 25° C., or at most 24° C., or at most 23° C., or at most 22° C., at most 21° C., or at most 20° C.

The operation parameters of transducer assemblies 300A, 300B, 300C (i.e., both ultrasound energy transmission and contact cooling) may induce specific temperature profiles of biological tissue in the central region of applicator (i.e. deep tissue region), which may be maintained throughout the respective treatment session (first stage time-period 615).

Figure 8A:
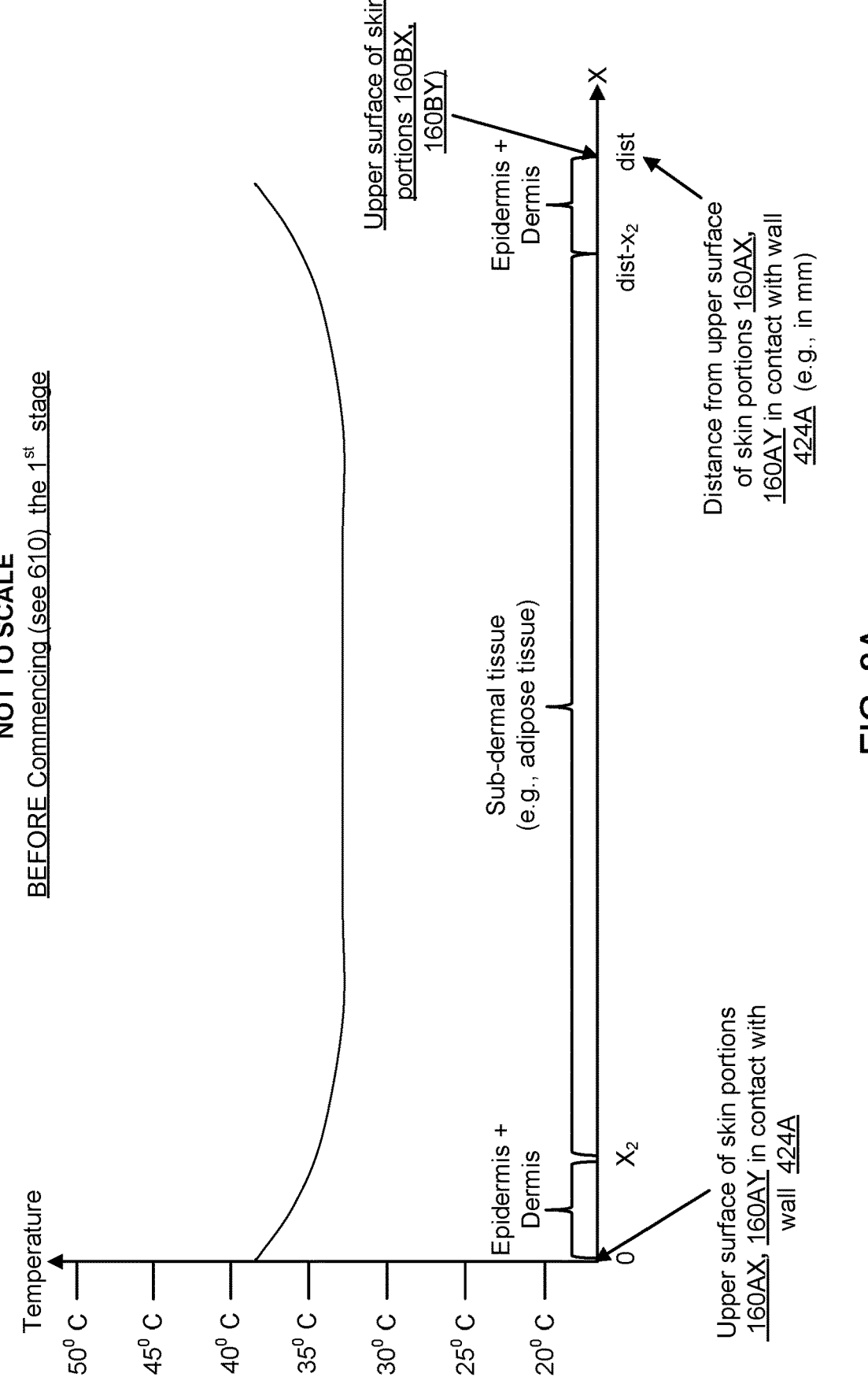
FIGS. 8A-8C illustrate temperature patterns during treatment procedure including the two stages of the method exemplified in FIGS. 6A-6C.
Figure 8B:
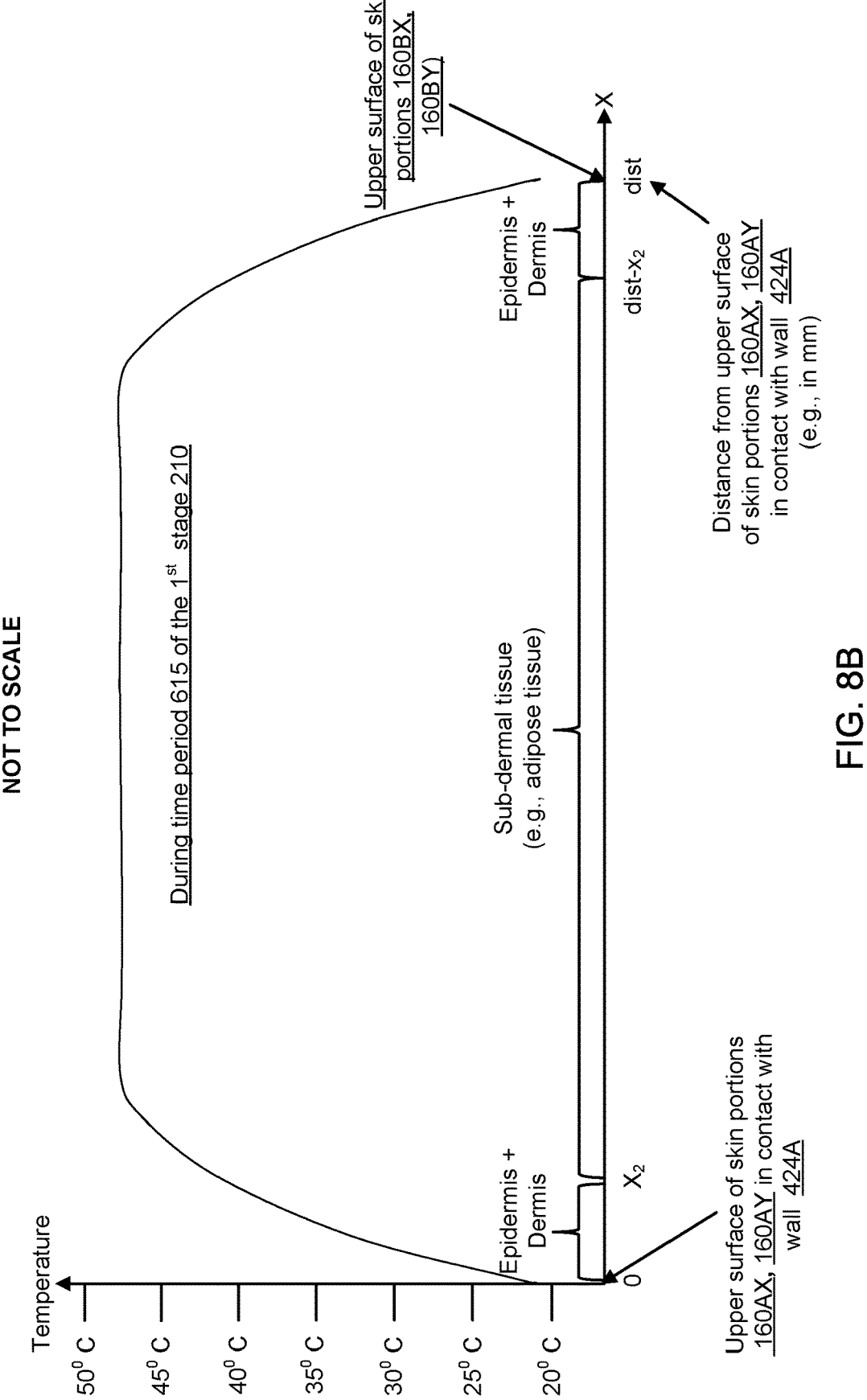
Figure 8C:
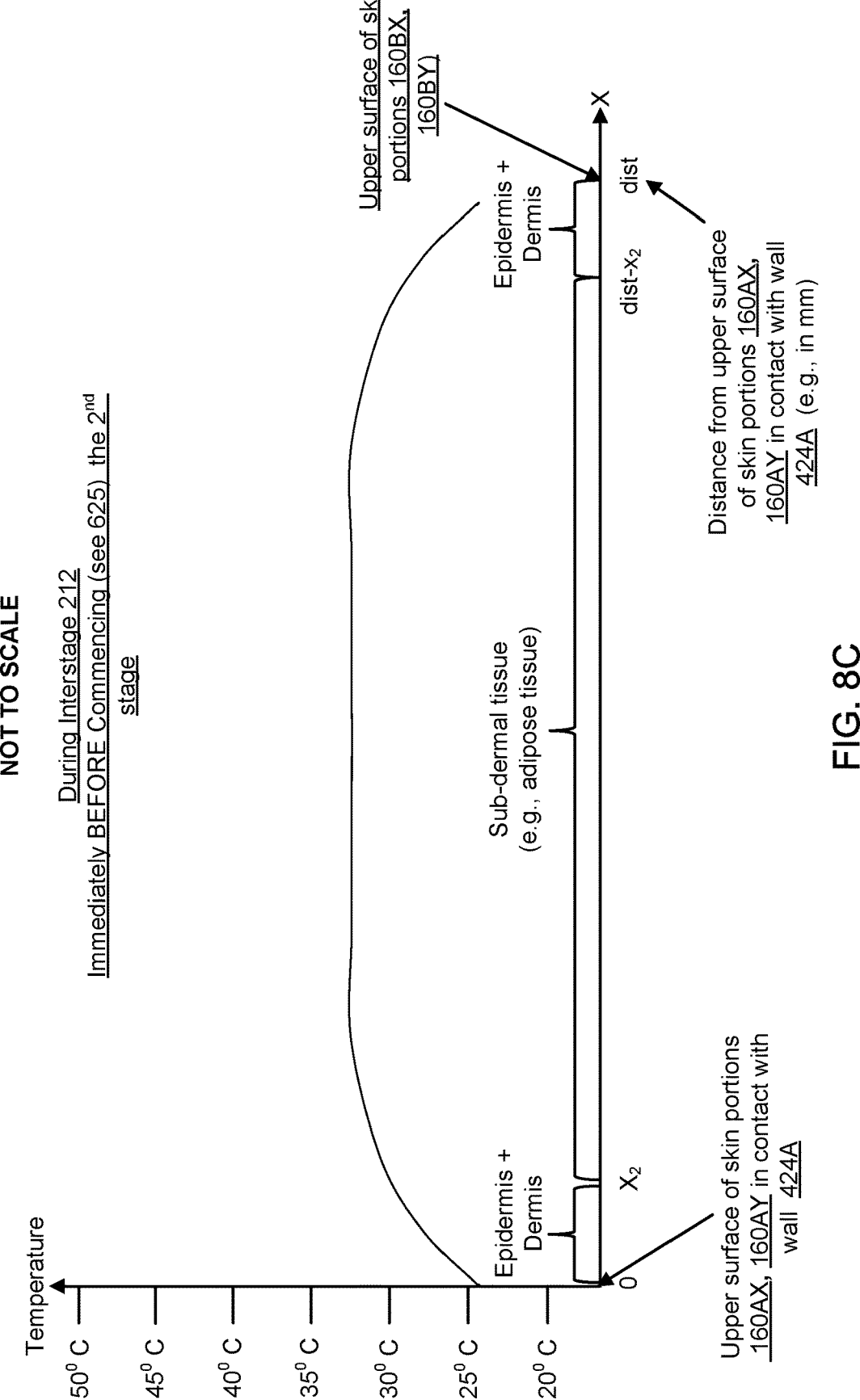

Reference is made to FIGS. 8A-8C. Before step 610, i.e., before the temperature ramp up pre-stage. The temperature profile of FIG. 8A may describe the temperature in both of the following locations/regions: region between respective skin-portions 160AX and 160BX and in mediating subdermal tissue 150X therebetween (skin portion 160AX faces to and contacts a skin-contacting surface 310 of assembly 300A while skin portion 160BX faces to and contacts a skin-contacting surface 310 of assembly 300B, skin portions 160AX and 160BX face away from each other); and regions between respective skin-portions 160AY and 160BY and in mediating subdermal tissue 150Y therebetween (skin portion 160AY faces to and contacts a skin-contacting surface 310 of assembly 300A while skin portion 160BY faces to and contacts a skin-contacting surface 310 of assembly 300B, skin portions 160AY and 160BY face away from each other).

During the time period 615 of the 1$^{st}$ stage 210 the temperature profile of FIG. 8B describes the temperature in both of the following locations/regions: regions between respective skin-portions 160AX and 160BX and in mediating subdermal tissue 150X therebetween; and regions between respective skin-portions 160AY and 160BY and in mediating subdermal tissue 150Y therebetween.

In this example, during the interstage 212 between the deep tissue treatment session 210 and skin tightening treatment session 214, all six transducer elements are dormant and the temperature profile of FIG. 8C describes the temperature in both of the following locations/regions: regions between respective skin-portions 160AX and 160BX and in mediating subdermal tissue 150X therebetween; and regions between respective skin-portions 160AY and 160BY and in mediating subdermal tissue 150Y therebetween.

Thus, as shown in FIG. 8B, significant portions of the mediating sub-dermal tissue 150 is heated to at least 45 degrees Celsius. For example, at least 80%, by volume, of mediating subdermal tissue 150 (e.g. centrally-located or otherwise) may be heated to at least 45 degrees Celsius and maintained at or above 45° C. (i.e., in the 45+° C. temperature range) for throughout the deep tissue treatment session (first-stage time-period 615) and/or for a period of time whose length is at least any defined duration defined for first-stage time-period 615 (e.g. at least 5 minutes or at least 10 minutes or at least 15 minutes).

After a conclusion step 620 of stage 210, this mediating tissue 150 (i.e., at least some of it or all of it) may be cooled (e.g., due to reduced or zero ultrasound-energy delivered from 300A and/or 300B) so there is a cooling or temperature ramp-down of the mediating tissue 150. The temperature profile of all the skin portions 160 and and/or mediating tissue 150 may be illustrated by FIG. 8C.

Distribution of the events of the second stage treatment (skin tightening treatment) are exemplified in FIG. 9A. During the second skin treatment stage 214 (i.e., for skin tightening), all six transducers' elements are dormant most of the time.

Furthermore, each piezoelectric transducer element (e.g., ceramic) may perform one or more brief shallow-heating events using a frequency that satisfies both of the following conditions: (i) is at least 4 MHz (e.g., at least 5 MHz or at least 6 MHz or at least 8 MHz or at least 10 MHz) and (ii) is significantly higher than$freq\_stage1$.

Figure 9B:
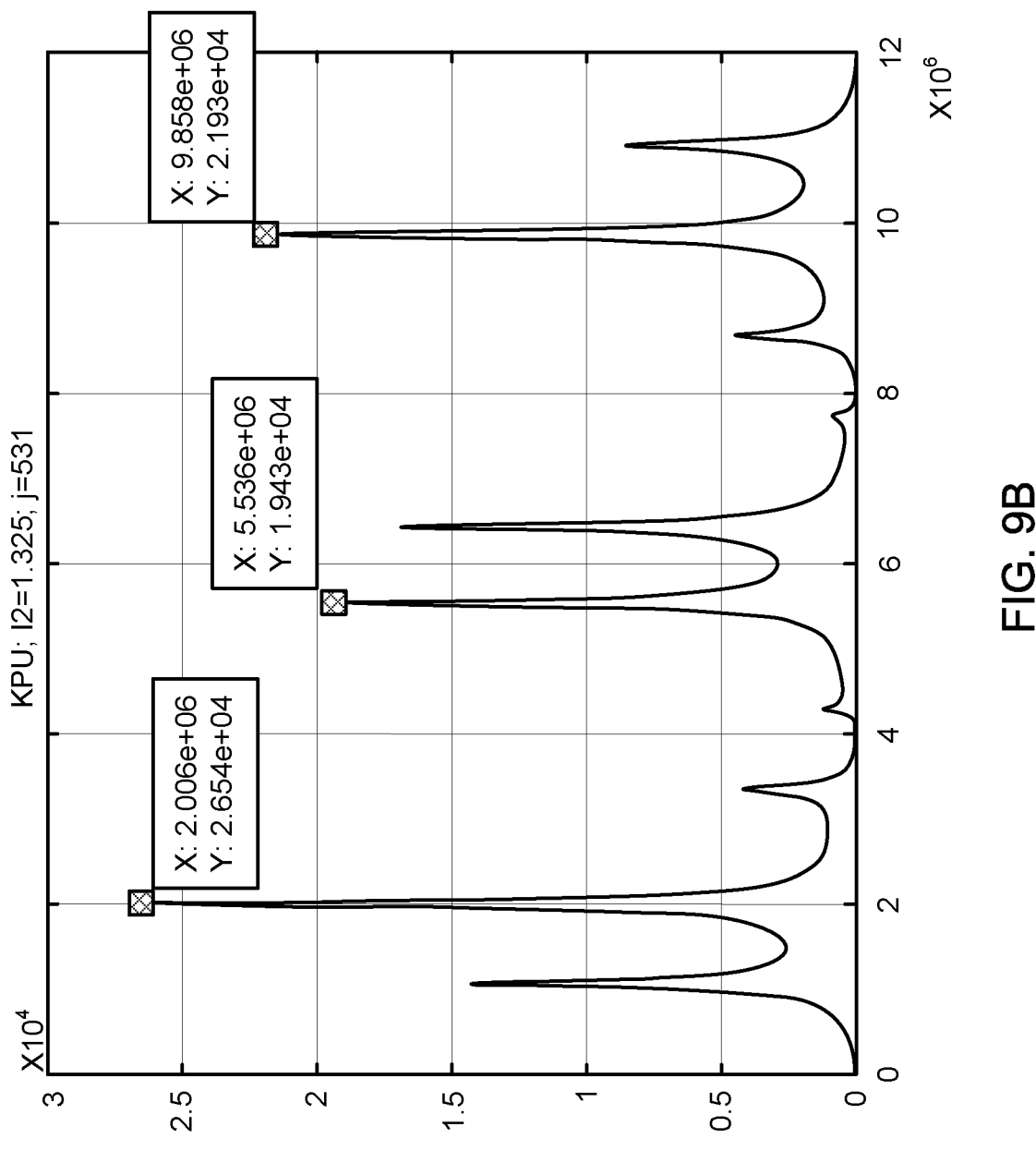
FIG. 9B exemplifies the ultrasound transducer operation with three resonate frequencies: first harmonic (main frequency) ~2 Mhz, third harmonic ~5.53 Mhz, and fifth harmonic ~9.85 Mhz.

FIG. 9B shows an exemplary graph of the transfer function of electrical power to ultrasound pressure. As can be seen, there are for example three resonate frequencies of the same transducer: first harmonic (main frequency) ~2 Mhz, third harmonic ~5.53 Mhz, and fifth harmonic ~9.85 Mhz. Typically, in order to operate with the same transducer with all three harmonics, the impedance matching layer of the applicator (between the piezo element and skin) is configured with selected material and thickness to optimize the efficiency in the transition between electrical and acoustic energy at all three frequencies.

A 'shallow brief heating event' may be effective to raise a temperature of at least a part of skin portion 160 (e.g., at skin portion 160AX or 160AY or 160BX or 160BY) to at least 45° C. for a period of time that is at least 5 seconds and at most 60 seconds (e.g., between 5 and 45 seconds, or between 5 and 30 seconds) even when an upper surface of the skin at those locations (e.g., portion locations in contact with applicator walls 424A) remains at relatively 'low' temperature (i.e. 30° C., or at most 25° C., or at most 24° C., or at most 23° C., or at most 22° C., at most 21° C., or at most 20° C.) due to contact-cooling.

This may be associated with that one or more piezoelectric transducer elements (e.g., ceramics) emits ultrasound at a relatively 'high' frequency so that most of the energy, for example, is concentrated within the skin rather than penetrating to deeper layers of tissues.

A first type of brief shallow-heating event may utilize an ultrasound frequency which is between 150% and 250% of the frequency of the first stage, $freq\_stage1$ and is described by broken line in FIG. 9A, and a second type of brief shallow-heating event may comprise an ultrasound frequency which is between 300% and 600% of the frequency of the first stage, $freq\_stage1$, and is described in FIG. 9A by solid line. It is, therefore, expected that the higher frequency of the second type provides 'more shallow' heating.

Thus, as shown in FIG. 9A, the transducer arrangement formed by multiple transducer elements (6 piezoelectric transducer elements 300AA, 300AB, 300BA, 300BB, 300CA, 300CB) produce 12 brief shallow-heating events denoted by 'Event A' to 'Event L'.

Figure 9C:
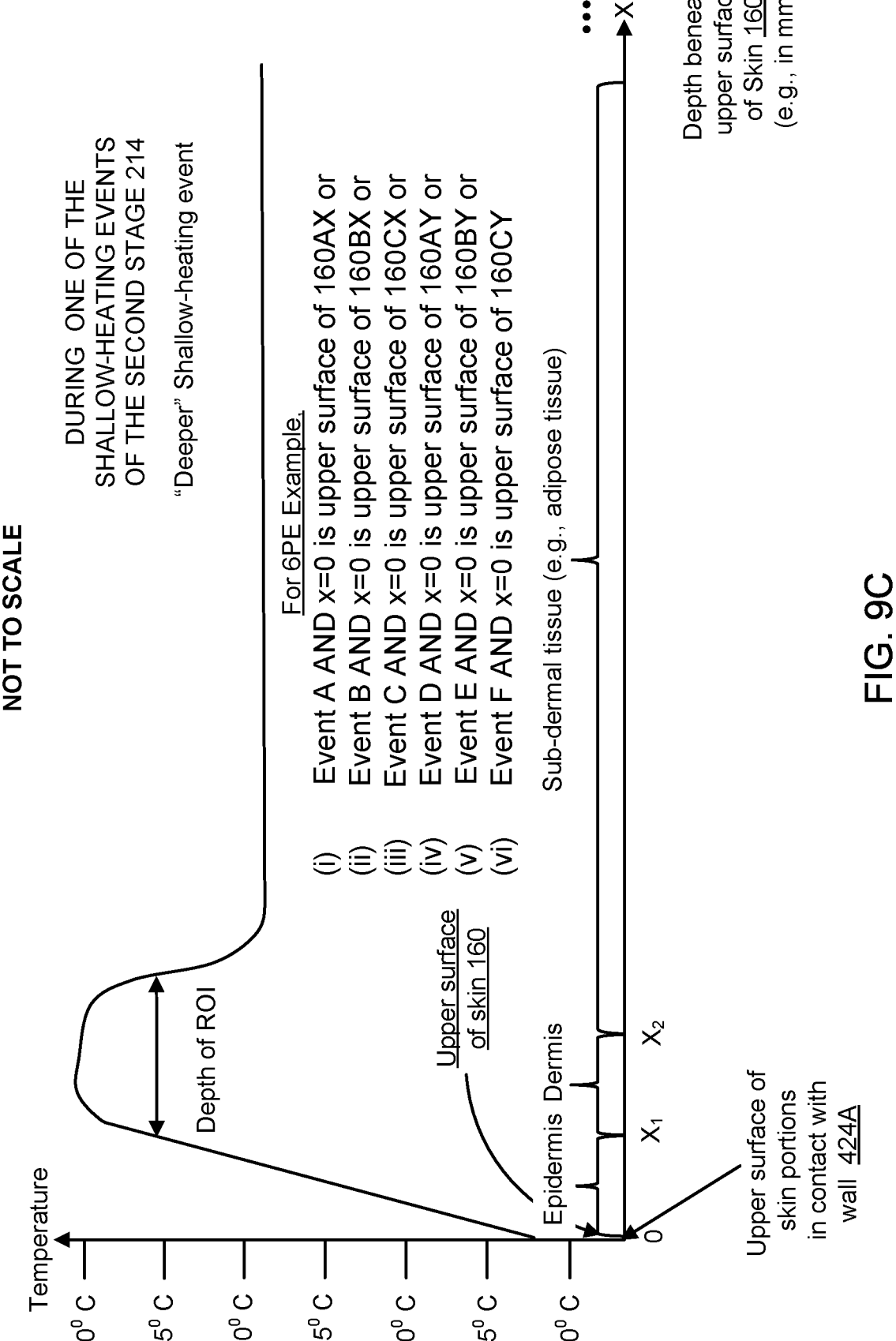
FIGS. 9C and 9D illustrate temperature profiles resulting from, respectively, the sequence of events A to F, and the sequence of events G to L, in the example of FIG. 9A.

Events denoted by the 'broken line' frequency (i.e., events A through F, i.e., between 150% and 250% of $freq\_stage1$) may produce shallow heating of most of the dermis region of skin portion 160, near to the skin surface (i.e., of the skin in contact with the transducer assembly at a location of the relevant piezoelectric transducer elements). FIG. 9C illustrates a corresponding temperature profile resulting from the sequence of these events A to F. Here, the skin portion 160 is constituted by epidermal and dermis layers of respectively about 200 μm and 2-3 mm. In the figure, the width of the temperature peak corresponds to the depth of region of interest ROI being heated.

Figure 9D:
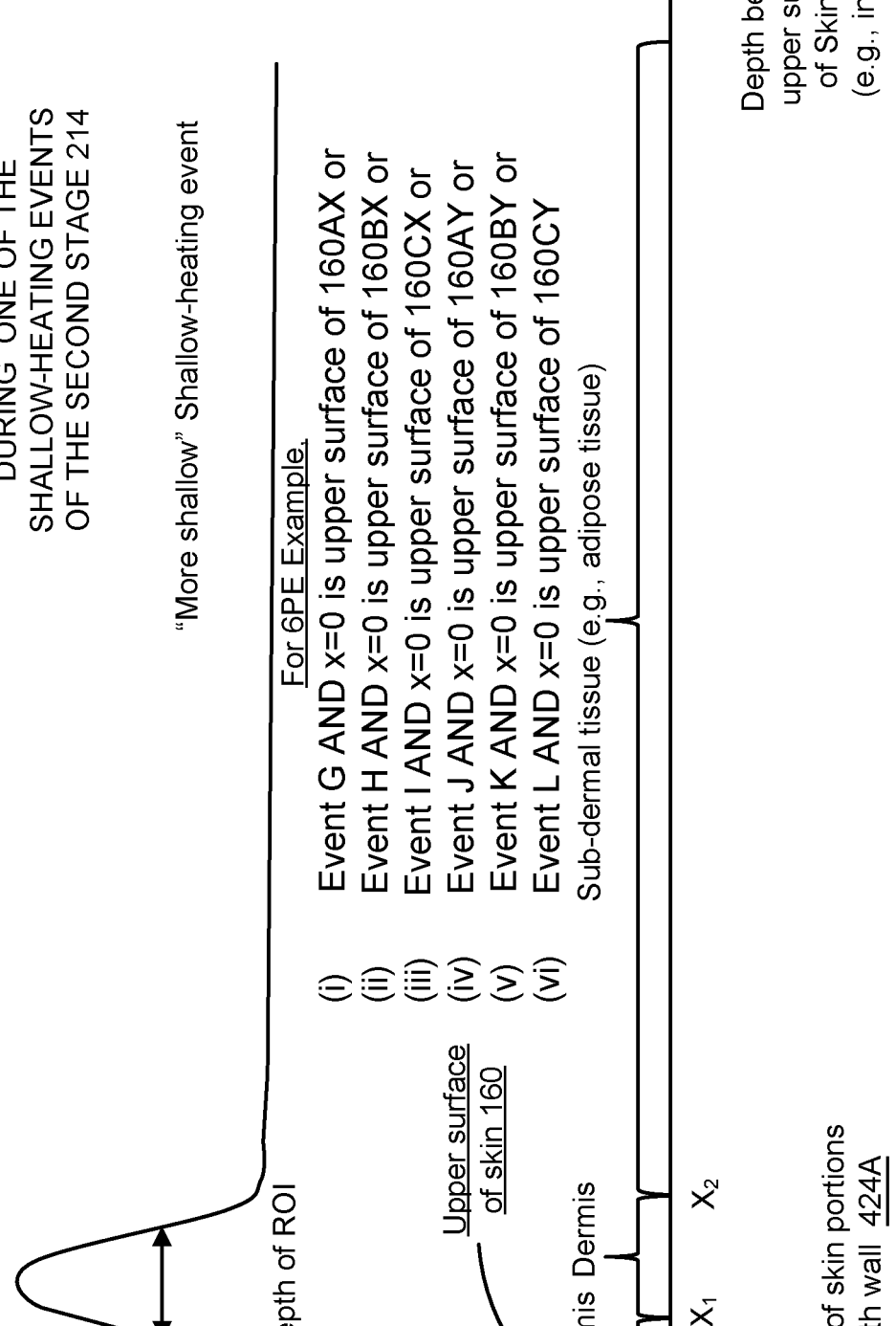

In FIG. 9A, events denoted by the 'solid line' frequency (i.e., events G through L i.e., between 300% and 600% of $freq\_stage1$) may produce even shallower heating, closer to the epidermis of the skin, very near the skin surface (i.e., of the skin in contact with the transducer assembly at a location of the relevant piezoelectric transducer elements). FIG. 9D illustrates a corresponding temperature profile resulting from the sequence of these events G to L. As can be seen in FIGS. 9C and 9D, the use of lower frequencies of ultrasound radiation during the heating session (e.g. 150%-250% of that/those used for deep tissue treatment) illustrated in FIG. 9B provides for heating shallow regions, while using somewhat higher frequencies (e.g. 300%-600% of that/those used for deep tissue treatment) heating is applied to more shallow regions.

In some examples, for a given piezoelectric transducer element (e.g., 300AA or 300AB or 300BA or 300BB or 300CA or 300CB), an amount of time elapsed between the end of one event and the beginning of a subsequent event (denoted as 'Inter-event time-period' in FIG. 9A) is at least 20 seconds or at least 30 seconds—thus, in FIG. 9A, the duration of 'Inter-event time period (Event A, Event G)' is ≥20 seconds or ≥30 seconds and/or the duration of 'Inter-event time period (Event B, Event H)' is ≥20 seconds or ≥30 seconds) and so on.

In FIG. 9A, the intensity of CW ultrasound delivered by a transducer element or by the ultrasound assembly in general (e.g., 300A and/or 300B and/or 300C) has a "square form". However, this should not be interpreted as a limitation. One salient feature of a square form is that the intensity of ultrasound energy increases by a factor of at least 5 or at least 10 or at least 100 within a "short" period of time (i.e. at most 5 seconds or at most 3 seconds or at most 1 second), and then stays relatively constant, and then decreases (i.e. within another short period of time—i.e. at most 5 seconds or at most 3 seconds or at most 1 second) to an intensity that is at most 50% or at most 30% or at most 10% or at most 5% of its previous intensity value. Here, "intensity" refers to power density (e.g., Watts/cm$^2$) delivered through respective forward-facing surfaces 310 of the transducer assemblies.

In some embodiments, some of the ultrasound heating events may produce a temperature profile similar to that of FIG. 9C while others may produce a temperature profile similar to that of FIG. 9D.

During the second stage 214 and through the majority of the time of the second stage 214 (e.g. throughout an entirety of the second stage 214), at least 60% or at least 70% or at least 80% or at least 90% or at least 95% by volume of mediating subdermal tissue 150X and/or 150Y is maintained at a temperature that is at most 42° C. or at most 40° C. or at most 38° C. or at most 36° C. (e.g. 'physiological"), as shown in the temperature profiles of FIGS. 9A and 9C.

In some embodiments, at least one of the 'shallow brief heating events' of the second stage 214 described with reference to FIG. 9A, e.g., performed by the ultrasound assembly 300A (any of Events A, B, C, G, H, I) and at least one of the 'shallow brief heating events' of the second stage 214 described with reference to FIG. 9A, e.g., performed by the ultrasound assembly 300B (any of Events D, E, F, J, K, L) in the respective skin portions 160AX or 160AY or 160BX or 160BY are performed simultaneously.

Thus, during the second stage 214, the following may be provided: a majority of the time of the second stage 214 (e.g. throughout an entirety of the second stage 214), at least 60% or at least 70% or at least 80% or at least 90% or a least 95% by volume of the deep tissue region is maintained at a temperature that is at most 42° C. or at most 40° C. or at most 38° C. or at most 36° C. (e.g. 'physiological"). Generally, for skin tightening treatment, third/fifth harmonics can be used for dermis heating only (not fat tissue heating). Fifth harmonic (highest freq.) can be used for "more shallow" heating, and third harmonic—for "deeper" heating.

Turning back to FIGS. 6A-6C, the following should be noted. The method of FIG. 6A is exemplified for a "tissue-engaged time-period" when a volume of a subject's biological tissue remains continuously engaged (e.g., to provide a continuous CONTACT-STATE or VACUUM-STATE) to the transceiving surfaces of both transducer assemblies 300A and 300B of the applicator, e.g., during a time-period which begins no later than step 610 and ends no early than step 630.

The engagement (i.e., which may correspond to any time-period of any CONTACT-STATE, or any VACUUM-STATE discussed herein of the "tissue-engaged time-period") may be such that: (i) a first (e.g., flat) skin-portion 160 (see FIG. 4B) of the biological tissue is continuously maintained in contact with the first transceiving surface (with an energy-delivery and/or cooled surface 310) of the transducer assembly 300A; and (ii) a second (e.g., flat) skin-portion 160 (see FIG. 4B) of the biological tissue is continuously maintained in contact with the second transceiving surface (with an energy-delivery and/or cooled surface 310) of the transducer assembly 300B.

It should be noted that, when the present document specifies the occurrence of a ultrasound heating event at a given location (or a given region) of biological tissue (e.g. at least partly in the skin), this does not mean that the event occurs only at the given location (or a given region) of biological tissue but rather that the event occurs at least at the given location (or given region), i.e. the event may optionally also occur in additional locations (for example, immediate neighboring locations) or additional region(s) (for example, immediate neighboring regions) of biological tissue (e.g. either additional location(s) or region(s) of skin portion 160 or other biological tissue, for example, subdermal tissue 150). The ultrasound heating event may occur in a portion of skin 160 (e.g., at or near to the interface region defined by transceiving surfaces of transducer assemblies 300A and/or 300B and/or 300C)—for example, in an epidermis or dermis thereof.

Figure 10:
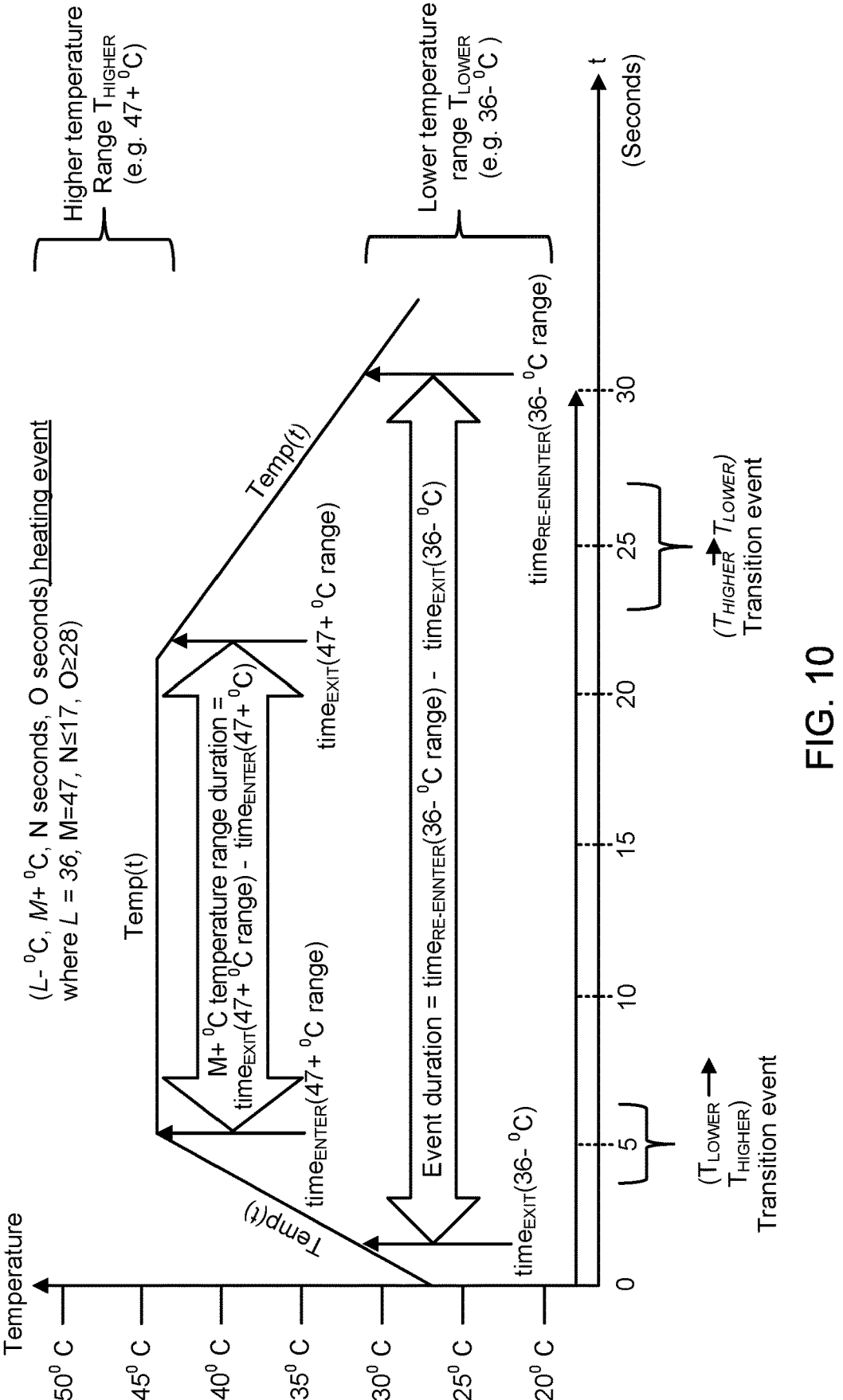
FIG. 10 exemplifies more specifically the heating event (interval of treatment session), e.g. lasting for about 30 sec implemented using the technique of the present invention.

Reference is now made to FIG. 10 which exemplifies more specifically the heating event (interval of treatment session), e.g. lasting for about 30 sec. Here, the following reference indices are used: L–° C., M+° C., N seconds, O seconds) are 'ultrasound heating events' where all of L, M, N and O are positive numbers, M>L and O>N. The term 'ultrasound' heating event means the heating is caused by delivery of ultrasound energy. The term 'heating event' requires heating; however, aspects of the subsequent cooling of the location (or region) of biological tissue are also described by the parameters L, M, N and O.

In the expression (L–° C., M+° C., N seconds, O seconds), L–° C. refers to a L–° C. temperature range (see the definition above for X–° C. temperature range) and M+° C. refers to a M+° C. temperature range. By definition, a duration of the (L–° C., M+° C., N seconds, O seconds) ultrasound heating event is at most O seconds where O is a positive number. When a (L–° C., M+° C., N seconds, O seconds) ultrasound heating event occurs at the location (or region) of biological tissues, the following occurs:

(i) the location (or region) of biological tissue is ultrasound-heated from the L–° C. temperature range (i.e. which is a lower temperature range) into the M+° C. temperature range (i.e. which is a higher temperature range, since M>L). The latest time when a temperature of the location is in the L–° C. temperature range before subsequently first entering the M+° C. temperature range is $\text{time}_{EXIT}$(L–° C. range);

(ii) the location (or region) of biological tissue subsequently and continuously remains in the M+° C. temperature range (i.e. due to ultrasound heating) for at least N seconds;

(iii) subsequently, the location (or region) of biological tissue cools from the higher M+° C. temperature range back down into the lower L–° C. temperature range (i.e. due to cooling applied—for example—to the upper surface 124 of skin—e.g. contact-cooling with a surface (e.g. 310) of the any ultrasound assembly) so as to first "re-enter" the L–° C. temperature range at a time $\text{time}_{RE\text{-}ENTER}$(L–° C. range) after spending at least N seconds in the M+° C. temperature range;

(iv) as described above, the duration of the (L–° C., M+° C., N seconds, O seconds) ultrasound heating event is at most O seconds. The "duration" of an (L–° C., M+° C., N seconds, O seconds) ultrasound heating event is defined as $\text{time}_{RE\text{-}ENTER}$(L–° C. range)–$\text{time}_{EXIT}$(L–° C. range) and most not exceed O seconds.

FIG. 10 exemplifies temperature Temp (t) as a function of time for a location (or region) in biological tissue (e.g. in skin portion thereof). In this simplified example, Temp (t) is characterized by 3 straight lines though this is clearly not a limitation, where the increase(s) of temperature (i.e. characterized by Temp (t)) at the location (or region) is due to ultrasound heating of the biological tissue.

In the example of FIG. 10: there is a lower temperature range which is 36–° C., and a higher temperature range which is 47+° C.; the amount of time that Temp (t) stays in the higher temperature range (i.e. 47+° C.) is [$\text{time}_{EXIT}$(47+° C. range)–$\text{time}_{ENTER}$(47+° C. range)] which is 17 seconds; the elapsed amount of time between: (A) a time $\text{time}_{EXIT}$ (36–° C. range) (which is the latest time when a temperature of the location is in the 36–° C. temperature range before subsequently first entering the 47+° C. temperature range) and (B) a time $\text{time}_{RE\text{-}ENTER}$(36–° C. range) when the location (or region) first "re-enters" the 36–° C. temperature range after spending at least O seconds in the 47+° C. temperature range, is 28 seconds.

FIG. 10 thus clearly shows (i.e. for the location or region whose temperature profile is described by Temp (t))) a (36–° C., 47+° C., 8 seconds, 60 seconds) ultrasound heating event, i.e. a (L–° C., M+° C., N seconds, O seconds) ultrasound heating event where L=36, M=47, N=8, and O=60. Indeed, this is because the time pattern of the temperature profile provides that 17 seconds≥8 seconds (required duration of heating), and 28 seconds≤60 seconds. Also, FIG. 10 clearly shows (i.e. for the location or region whose temperature is described by Temp (t))) a (36–° C., 47+° C., 12 seconds, 45 seconds) ultrasound heating event, i.e. a (L–° C., M+° C., N seconds, O seconds) ultrasound heating event where L=36, M=47, N=12, and O=45 (because (because 17 seconds≥12 seconds, and because 28 seconds≤45 seconds).

Thus, the present invention provides a novel effective and safety technique for real time treatment of biological tissue at the individual's body part, which is particularly useful for fat reduction and skin tightening. The applicator of the present invention is configured for applying heat-based tissue treatment (preferably ultrasound-based treatment) while providing desired acoustic contact between the tissue surface and the U-shaped interface region defined by the applicator. The applicator also utilizes ultrasound-based control (continuous or almost continuous) of the temperature and tissue attachment conditions during the treatment session. Various embodiments and example of the applicator configuration and operation are described above.

In some embodiments, as described above, the medical device of the present invention includes the applicator 102 carrying first and second 300B ultrasound transducer-assemblies, each having respective forward-facing transceiving surface 310 by which it faces the other opposing transceiving surface via a mediating region between the arms of the U-shaped interface region of the applicator 102. During a tissue-engaged time-period, when a volume of the biological tissue remains continuously attached to the interface region or continuously disposed in the mediating region between the arms of the U-shaped interface region of the applicator, at least one treatment-operation is performed.

During an entirety of the tissued-engaged time-period, the volume of the biological tissue remains continuously engaged to the applicator 102 such that a first skin-portion of the biological tissue (e.g., 160AX and 160AY in FIG. 7B) is continuously maintained to face towards the forward-facing surface 310 of the first transducer assembly 300A and in continuous contact therewith; and a second skin-portion of the biological tissue (e.g., 160BX and 160BY in FIG. 7B), which has the same lateral dimensions as the first skin-portion, is continuously maintained. With this configuration, the second skin-portion of the biological tissue faces away from the first skin-portion, is in lateral alignment with the first skin-portion to define mediating subdermal tissue 150 (FIG. 7B) which is disposed between the first and second skin-portions and longitudinally spans therebetween (a lateral cross-section of the mediating subdermal tissue 150 has lateral dimensions that are the same as the lateral dimensions of both of the first and second skin-portions); and continuously faces towards the forward-facing surface 310 of the respective second 300B ultrasound transducer being in continuous contact therewith.

As described above, in particular with reference to FIGS. 6A to 6C, at least one treatment operation performed during the tissue-engaged time-period may include a first treatment-stage 210 which may be as follows: During the first stage 210, which includes a first-stage time-period 615 whose duration is at least 5 minutes, each of the first and second transducer assemblies 300A and 300B delivers ultrasound to the mediating region 150 (FIG. 4C) via respective forward-facing surfaces 310 thereof and contact cooling is applied by the applicator 102 to the biological tissue such that for an entirety of the first-stage time-period 615, a first set of tissue-temperature conditions is continuously maintained. The first set may be defined as follows: a first-stage fraction Stage1_Frac_MedTiss of the mediating subdermal tissue 150 which comprises at least 60% by volume of the mediating subdermal tissue 150 is maintained at or above a first-stage mediating-tissue minimum-threshold Stage1_SkinPortion_MIN whose value is at least 45° C.; and each of an upper surface of the first skin-portion and an upper surface of the second skin-portion is maintained at or below a first-stage skin-portion maximum-threshold Stage1_SkinPortion_MAX which is at most 30° C. Throughout the second stage 214 (whose duration is e.g. at least one minute and which concludes no later than 60 minutes after the conclusion of the first stage time period), a second-stage fraction Stage2_Frac_MedTiss of the mediating subdermal tissue 150 which comprises at least 60% by volume of the mediating subdermal tissue 150 is maintained at or below a second-stage mediating-tissue maximum-threshold Stage2_MedTiss_MAX whose value is at most 36° C.; the first 300A transducer assembly together with contact-cooling from the applicator produces one or more (36–° C., 45+° C., 8 seconds, 60 seconds) ultrasound-heating events in the first skin-portion (e.g., 160AX and/or 160AY in FIG. 7B); and the second 300B transducer assembly together with contact-cooling from the applicator produces one or more (36–° C., 45+° C., 8 seconds, 60 seconds) ultrasound-heating events in the second skin-portion (e.g., 160BX and/or 160BY in FIG. 7B).

In the above examples, at least one of the (36–° C., 45+° C., 8 seconds, 60 seconds) ultrasound-heating events in the first skin-portion; and at least one of the (36–° C., 45+° C., 8 seconds, 60 seconds) ultrasound-heating events in the second skin-portion may be performed simultaneously.

In any of the previously described embodiments, the at least one operation performed when the volume of tissue remains continuously engaged to the applicator and/or continuously disposed in the mediation region, may include performing a first stage (e.g. as part of a multi-stage treatment protocol comprising the first stage and second subsequent stages as described with reference to FIGS. 6A to 6C) of treatment as follows: The first stage includes a first-stage time-period whose duration is at least 5 minutes (i.e. for the multi-stage treatment protocol example, stage concludes no later than 60 minutes after the conclusion of the first stage time period). For a temporal majority (e.g. at least 60% of or at least 70% of or at least 80% or at least 90%) of the first-stage time period, at least one of the following is true: Each of the first and second ultrasound transducer assemblies delivers [1 MHz, 4 MHZ] CW ultrasound (e.g. non-focused and/or [1.5 MHz, 3 MHz ultrasound]) into the mediation region; each of the first and second ultrasound transducer assemblies simultaneously delivers [1 MHz, 4 MHZ] CW ultrasound (e.g. non-focused and/or [1.5 MHz, 3 MHz ultrasound]) into the mediation region; and each of the first and second ultrasound transducer assemblies simultaneously deliver [1 MHz, 4 MHZ] CW ultrasound (e.g. non-focused and/or [1.5 MHz, 3 MHz ultrasound]) into the mediation region at respective instant CW ultrasound frequencies which differ from each other by least 0.5% and by at most 20%.

Also, during at least some of the second stage whose duration is at least one minute and which concludes no later than 60 minutes after the conclusion of the first stage time period, each of the first and second ultrasound transducers (optionally simultaneously), delivers to the mediating region (i.e. the biological tissue disposed therein), 4.5 Hz+ CW ultrasound energy whose frequency is at least 4.5 MHz or at least 5 MHz or at least 5.5 MHz or at least 6 MHz or at least 7 MHz or at least 8 MHz or at least 9 MHz.

In any of the previously described embodiments, the first-stage time-period has a duration of FS-TP seconds (i.e.

if a duration of time-period is at least 5 minutes then FS-TP must be at least 300). The first-stage time period is dividable into N non-overlapping intervals {Interval$_1$, interval$_2$ . . . interval$_N$} where N is a positive integer, each interval having a common-duration COM-DUR seconds (i.e. COM-DUR=FT-SP/N), the common-duration being at most 60 seconds or at most 50 seconds or at most 40 seconds or at most 30 seconds or at most 20 seconds or at most 10 seconds. For at least a temporal majority (e.g. for at least 60% or at least 70% or at least 80% or at least 90% of) of every i-th interval, interval$_i$ (1≤i≤N), the first ultrasound transducer assembly delivers [1 MHz, 4 MHZ] CW ultrasound (e.g. non-focused) into the mediation region. For at least 60% or at least 70% or at least 80% or at least 90% of every i-th interval, interval$_i$ (1≤i≤N), the second ultrasound transducer assembly delivers [1 MHz, 4 MHZ] CW ultrasound (e.g. non-focused) into the mediation region (e.g. at respective instant CW ultrasound frequencies which differ from each other by least 0.5% and by at most 15%).

During at least some of the second stage whose duration is at least one minute and which concludes no later than 60 minutes after the conclusion of the first stage time period, each of the first and second ultrasound transducers (optionally simultaneously), deliver to the mediating region (i.e. the biological tissue disposed therein), 4.5 Hz+ CW ultrasound energy whose frequency is at least 4.5 MHz or at least 5 MHz or at least 5.5 MHz or at least 6 MHz or at least 7 MHz or at least 8 MHz or at least 9 MHz.

In any of the previously described embodiments, at least 70% or at least 80% or at least 90% or at least 90% of ultrasound energy delivered to the mediating region during the first-stage time-period is [1 MHz, 4 MHz] CW ultrasound.

In any of the previously described embodiments, at least 70% or at least 80% or at least 90% or at least 90% of ultrasound energy delivered to the mediating region during the first-stage time-period is [1 MHz, 4 MHz] CW ultrasound and is transmitted by the first and/or second ultrasound transducer assemblies.

In any of the previously described embodiments, during at least some of the second stage whose duration is at least one minute and which concludes no later than 60 minutes after the conclusion of the first stage time period, a third ultrasound transducer assembly (e.g. having a forward-facing surface 310 which corresponds to at least a portion of wall 424C) delivers 4.5 Hz+ CW ultrasound energy whose frequency is at least 4.5 MHz or at least 5 MHz or at least 5.5 MHz or at least 6 MHz or at least 7 MHz or at least 8 MHz or at least 9 MHz.

In any of the previously described embodiments, the second stage may include an interval whose duration is at least 5 seconds (e.g. at least 10 seconds) when the first and/or second ultrasound transducer assemblies deliver 4.5 Hz+ CW ultrasound energy, to the mediating region, whose frequency is at least 4.5 MHz or at least 5 MHz or at least 5.5 MHz or at least 6 MHz or at least 7 MHz or at least 8 MHz or at least 9 MHz, and wherein during other intervals of the second stage, at least 70% or at least 80% or at least 90% or at least 90% of ultrasound energy delivered to the mediating region is CW ultrasound energy having a frequency of at least at least 4.5 MHz or at least 5 MHz or at least 5.5 MHz or at least 6 MHz or at least 7 MHz or at least 8 MHz or at least 9 MHz.

In any of the previously described embodiments, the contact-cooling that is applied during first and/or second stage includes contact-cooling applied by the forward-facing surface 310 of the first transducer-assembly 300A and/or applied by the respective forward-facing surface 310 of the second transducer-assembly 300B.

In any of the previously described embodiments, the first-stage fraction Stage1_Frac_MedTiss of the mediating subdermal tissue 150 may include at least 65% or at least 70% or at least 80% or at least 90% by volume of the mediating subdermal tissue 150. In any of the previously described embodiments, the first-stage fraction Stage1_Frac_MedTiss of the mediating subdermal tissue 150 may include at least 65% or at least 70% or at least 80% or at least 90% by volume of the most central mediating subdermal tissue 150 between the first and the second respective forward-facing surfaces 310 of the first 300A and second 300B ultrasound transducer assemblies.

In any of the previously described embodiments, the first-stage mediating-tissue minimum-threshold Stage1_SkinPortion_MIN may be of a value of at least 46° C. or at least 47° C. and/or the first-stage skin-portion maximum-threshold Stage1_SkinPortion_MAX may be at most 25° C. or at most 20° C. The duration of the first-stage time-period 615 may be at least 5 minutes or at least 7 minutes or at least 10 minutes or at least 12 minutes or at least 15 minutes.

In any of the previously described embodiments, the second-stage fraction Stage2_Frac_MedTiss of the mediating subdermal tissue may include at least 65% or at least 70% or at least 80% or at least 90% by volume of the mediating subdermal tissue. The second-stage fraction Stage2_Frac_MedTiss of the mediating subdermal tissue 150 may include at least 65% or at least 70% or at least 80% or at least 90% by volume of the most central mediating subdermal tissue 150 between the respective first and second forward-facing surfaces 310 of the first and second ultrasound transducer assemblies.

In any of the previously described embodiments, both of the first (e.g., 160AX and/or 160AY in FIG. 7B) and second (e.g., 160BX and/or 160BY in FIG. 7B) skin-portions are maintained flat during the entirety of the tissue-engaged time-period. A longitudinal separation between respective upper surfaces of the first and second skin-portions may be maintained constant throughout the tissue-engaged time-period to a separation value that is between 2 cm and 7 cm (e.g. between 2 cm and 3 cm or between 3 cm and 4 cm or between 4 cm and 5 cm or between 5 cm and 6 cm or between 6 cm and 7 cm). The area of each of the first and second skin-portions may be at least 4 cm$^2$. For example, at least 5 cm^2 or at least 6 cm$^2$ or at least 10 cm$^2$ or at least 12 cm$^2$ or at least 15 cm$^2$). An aspect-ratio of each of the first and second skin-portions may be between 0.3 and 3.

In any of the previously described embodiments, during the first-stage time-period (e.g. during a temporal majority thereof), ultrasound transmitted longitudinally by the first ultrasound transducer-assembly 300A via the first forward-facing surface 310 passes longitudinally through at least 50% by area or at least 75% by area or at least 90% by area of the first skin-portion; and/or ultrasound transmitted longitudinally by the second ultrasound transducer-assembly 300B via the second forward-facing surface 310 passes longitudinally through at least 50% by area or at least 75% by area or at least 90% by area of the second skin-portion. During the second 214 stage of a multi-stage treatment protocol, ultrasound transmitted longitudinally by the first ultrasound transducer-assembly 300A via the first forward-facing surface 310 passes longitudinally through at least 50% by area or at least 75% by area or at least 90% by area of the first skin-portion; and/or ultrasound transmitted longitudinally by the second ultrasound transducer-assembly 300B via the second forward-facing surface 310 passes longitudinally through at least 50% by area or at least 75% by area or at least 90% by area of the second skin-portion.

In any of the previously described embodiments, the applicator includes specific locations, which are LOCi, first LOC1, second LOC2, third LOC3 and fourth LOC4, where the first LOC1 and second locations LOC2 are both disposed on the forward-facing surface 310 of the first ultrasound transducer assembly 300A, the third LOC3 and fourth locations LOC4 are both disposed on the forward-facing surface 310 of the second ultrasound transducer assembly 300B; a line segment LOC1-LOC2 connecting the first LOC1 and second LOC2 locations is parallel to and equal in length with a line segment LOC3-LOC4 connecting the third LOC3 and fourth LOC4 locations; and a line segment LOC1-LOC3 connecting the first LOC1 and third LOC3 locations is parallel to and equal in length with a line segment LOC2-LOC4 connecting the second LOC2 and fourth LOC4 locations. For example, a ratio between a length of LOC1-LOC2 and a length of LOC1-LOC3 is at least 0.5 or at least 0.6 or at least 0.7 or at least 0.8 or at least 0.9 or at least 1 or at least 1.1 or at least 1.2 or at least 1.3; and/or the length of both of LOC1-LOC2 and LOC3-LOC4 is at least 5 cm; and the length of both of LOC1-LOC3 and LOC2-LOC4 is at most 7 cm or at most 6 cm or at most 5 cm.

In some embodiments, during at least some of (e.g. during a temporal majority thereof) the first-stage time-period 615, both of the following simultaneously occurs: (i) the first transducer assembly 300A simultaneously and longitudinally transmits ultrasound, via both of the first LOC1 and second LOC2 locations of the forward-facing surface 310, into the first skin-portion (e.g., 160AX and/or 160AY in FIG. 7B); (ii) the second transducer assembly 300B simultaneously and longitudinally transmits ultrasound, via both of the first LOC3 and second LOC4 locations of the forward-facing surface 310, into the second-skin portion (e.g., 160BX and/or 160BY in FIG. 7B).

In any of the previously described embodiments, the first and second forward-facing surfaces 310 may be surfaces of parallel plates.

In any of the previously described embodiments, wherein a majority (e.g. at least 75% of or at least 90% or at least 99%) of energy delivered to the biological tissue during the first time period 615 is ultrasound energy (e.g. non-focused ultrasound and/or ultrasound having a frequency of at most 4 MHz and/or having a frequency of at least 1 MHz (or at least 1.5 MHz)). The operation can be such that the ultrasound energy is longitudinally transmitted by the first ultrasound transducer assembly 300A to the tissue via forward-facing surface 310 to enter the biological tissue via the first skin-portion (e.g., 160AX and/or 160AY in FIG. 7B); or the ultrasound energy is longitudinally transmitted by the second ultrasound transducer assembly 300B to the tissue via forward-facing surface 310 to enter the tissue via the second skin-portion (e.g., 160BX and/or 160BY in FIG. 7B).

In any of the previously described embodiments, one or both a first energy-delivery condition and a second energy-delivery conditions are controlled. These first and second conditions are defined as follows: According to the first energy-delivery condition, at least a majority of the ultrasound energy that is delivered to the biological tissue via forward-facing surface 310 during the first stage 210 is longitudinally (e.g. directly) delivered via the first skin-portion (e.g., 160AX and/or 160AY in FIG. 7B). According to the second energy-delivery condition, at least a majority of the ultrasound energy that is delivered to the biological tissue via forward-facing surface 310 during the first stage 210 is longitudinally (e.g. directly) delivered via the second skin-portion (e.g., 160BX and/or 160BY in FIG. 7B).

In any of the previously described embodiments, at least p % (where p≥70) of the energy required to maintain, during an entirety of the first-stage time-period 615, the at least 80%, by volume, of the mediating subdermal tissue 150 at or above 45° C., is ultrasound energy which is delivered via the first and second forward-facing transceiving surfaces 310. For example, p is at least 80 or at least 90 or at least 95.

In any of the previously described embodiments, for at least one given time-period being the first stage time-period 615 and/or a time-period of the second stage 214, the majority (e.g. at least 75% of at least 90%), by energy, of ultrasound delivered by the first ultrasound transducer assembly 300A via the first forward-facing transceiving surface 310 (and/or by the second ultrasound transducer assembly 300B via the second surface 310) so as to enter the biological tissue via the first and/or second skin-portion(s) towards the region(s) of interest (biological tissue) is unfocused ultrasound (CW ultrasound) and/or ultrasound (CW ultrasound) whose frequency is between 1 MHz and 4 MHz (e.g. about 1.5 MHz). Throughout the temporal majority of every 30 second time-period, respective instant CW ultrasound frequencies of ultrasound from the first and second transducer assemblies differ from each other by least 0.5% and by at most 20%.

In any of the previously described embodiments: The first forward-facing transceiving surface 310 may be of smallest rectangle subsurface SRS(FIRST), having length L1 and width W1, via which at least 30% of the energy required to maintain, during the entirety of the first-stage time-period 615, the at least 80%, by volume, of the mediating subdermal tissue 150 at or above 45° C., is supplied. Also, the second forward-facing surface 310 has smallest rectangle subsurface SRS(SECOND), having length L2 and width W2, via which at least 30% of the energy required to maintain, during the entirety of the first-stage time-period 615, the at least 80%, by volume, of the mediating subdermal tissue 150 at or above 45° C., is supplied. Further, a longitudinal separation distance between SRS(FIRST) and SRS(SECOND) is dist, and the following conditions are satisfied: max(L1, W1)/dist=0.8; and max(L2, W2)/dist=0.8.

In any of the previously described embodiments, there may be no externally-supplied inward pressure onto the tissue in the longitudinal direction.

In any of the previously described embodiments, mediating skin may be defined as disposed between the first (e.g., 160AX and/or 160AY in FIG. 7B) and second skin-portions (e.g., 160BX and/or 160BY in FIG. 7B), and the applicator 102 may be configured and the tissue is engaged thereto such that throughout an entirety of the tissue-engaged time-period a fraction of the mediating skin comprising at least 50% (e.g. at least 60% or at least 70% or at least 80% or at least 90% or at least 95% or exactly 100%) by area of the mediating skin may be maintained in contact (in cooled contact) with a surface (e.g. surface 424A and/or 424B and/or 424C) of the interface region 118 of applicator 102. For example, throughout at least the first stage time-period 615 (and optionally throughout all of the first stage and/or all of the second stage, and/or all of times after the conclusion of the first stage and before the commencement of the second stage) an upper-skin-surface temperature of the entire fraction of the mediating skin is always maintained at most 30° C. or at most 25° C. or at most 20° C. Also, perpendicular-and-mediating skin may be defined as mediating skin whose orientation is perpendicular to orientations of both of the first and second skin portions. The applicator 102 may be configured and the biological tissue is engaged thereto such that throughout an entirety of the tissue-engaged time-period a fraction of the perpendicular-and-mediating skin comprising at least 50% (e.g., at least 60% or at least 70% or at least 80% or at least 90% or at least 95% or exactly 100%) by area of the perpendicular-and-mediating skin is maintained in contact (in cooled contact) with a surface (e.g., surface 424A and/or 424B and/or 424C) of the applicator 102. Similarly to the above, throughout at least the first stage time-period 615 (and optionally throughout all of the first stage and/or all of the second stage, and/or all of times after the conclusion of the first stage and before the commencement of the second stage), an upper-skin-surface temperature of the entire fraction of the perpendicular-and-mediating skin is at always maintained at most 30° C. or at most 25° C. or at most 20° C.

For example, the mediating skin or the perpendicular-and-mediating skin includes a third skin region (e.g., 160CX and/or 160CY in FIG. 7B) whose area is equal to that of the first and second skin regions and optionally whose shape is the same as the shape of the first and second skin regions, and wherein contact-cooling is applied by the applicator 102 to the third skin-region during (e.g. for at least a majority of every 30 second interval thereof or throughout an entirety thereof) the first-stage time-period 615.

For example, the applicator 102 may include three inner walls 424A, 424B, 424C (see FIG. 4A) which all face to the mediating region respectively in first, second and third directions, where the first 424A and second 424B inner walls face each other, and the third direction is perpendicular to both of the first and second directions, and the respective first and second forward-facing transceiving surfaces 310 are respectively part of the first 424A and second 424B inner walls, and the third skin-region remains in contact with the third inner wall 424C throughout an entirety of the tissue-engaged time-period (e.g. the contact cooling is provided by the third wall 424C).

In some examples, the contact-cooling applied by the applicator 102 to the third skin-region (e.g., 160CX and/or 160CY in FIG. 7B) maintains an upper-surface-temperature thereof, throughout an entirety of the first stage time period 615, at-or-below 30° C., or at-or-below 25° C. or at-or-below 20° C.

In any of the previously described embodiments, wherein a temperature of a surface (e.g., upper surface of skin) of the skin 160 of biological tissue may be measured (e.g. by a thermocouple or any other surface-measurement device 132) and an intensity (e.g. cooling Watts) of contact cooling (e.g. Peltier cooling plate) may be controlled (e.g. by temperature controller 126) in accordance with the results of the surface temperature measurement.

For example, if the method were performed as-is other than a single modification, the single modification being a hypothetical absence of the contact cooling to the third skin-region (e.g., 160CX and/or 160CY in FIG. 7B), an upper-surface-temperature of the third skin-region would be at least 35° C., at least 38° C. or at least 40° C. or at least 42° C.

For example, a center of the third skin-region is longitudinally located midway between respective upper surfaces of the first and second skin regions.

For example, cooling of the biological tissue during the first stage time period is performed by the applicator 102 such that a ratio between a thermal-energy-outflow from the biological tissue via the third skin region which occurs during the first stage time period 615 as a result of the contact-cooling to the third skin region, and a thermal-energy-outflow from the biological tissue via the first skin region which occurs during the first stage time period 615 as a result of the contact-cooling to the first skin region or a result of the contact-cooling to the third skin region, and is at least 0.6 or at least 0.7 or at least 0.8 or at least 0.9 or at least 1 or at least 1.1 or at least 1.2 or at least 1.3.

In any of the previously described embodiments, the applicator 102 is configured and the biological tissue is engaged to the applicator such that during the tissue-engaged time-period, for at least some of the time, the applicator 102 delivers (e.g. unfocused and/or CW) ultrasound energy to the biological tissue via the third skin region (e.g., 160CX and/or 160CY in FIG. 7B). For example, no ultrasound energy may be delivered to the biological tissue via the third skin region during the first stage time period 615. In such embodiment, a ratio between an amount of ultrasound energy delivered to the biological tissue via the third skin region during the first stage time period 615 and a greater of a quantity of ultrasound energy delivered to the biological tissue via the first skin region during the first stage time period 615 and a quantity of ultrasound energy delivered to the biological tissue via the second skin region during the first stage time period 615, is at most 0.3 or at most 0.2 or at most 0.1 or at most 0.05.

In any of the previously described embodiments, the applicator 102 may include/define three inner walls 424A, 424B, 424C which all face to a mediating region respectively in first, second and third directions, where the first 424A and second 424B inner walls face each other, the third direction is perpendicular to both of the first and second directions, and the first and second forward-facing transceiving surfaces 310 are respectively part of the first 424A and second 424B inner walls. For example, third inner wall 424C bridges between the first 424A and second 424C inner walls. —The contact cooling may be applied, during at least some of the first-stage time-period 615, onto the biological tissue by the third 424C inner wall, for example such that an upper-skin-surface temperature of the entire fraction of the mediating skin is at always maintained at most 30° C. or at most 25° C. or at most 20° C. Alternatively or additionally, the contact cooling may be applied, during at least some (e.g. for a majority thereof or for a majority of every 30 second subinterval thereof) of the first-stage time-period 615, onto the biological tissue by a majority, by surface area, of the third 424C inner wall, for example such that an upper-skin-surface temperature of the entire fraction of the mediating skin is at always maintained at most 30° C. or at most 25° C. or at most 20° C.

In any of the previously described embodiments, during the second stage 214, the first transducer assembly 300A together with contact-cooling from the applicator may produce one or more (36–° C., 45+° C., 8 seconds, 60 seconds) ultrasound-heating events in throughout all lateral-locations of the first skin-portion. The second transducer assembly 300B together with contact-cooling from the applicator may produce one or more (36–° C., 45+° C., 8 seconds, 60 seconds) ultrasound-heating events throughout all lateral-locations of the second skin-portion. The first transducer assembly together 300A with contact-cooling from the applicator may produce one or more (36–° C., 47+° C., 8 seconds, 60 seconds) ultrasound-heating events throughout all lateral-locations of the first skin-portion. The second transducer assembly together 300B with the contact-cooling from the applicator may produce one more (36–° C., 47+° C., 8 seconds, 60 seconds) ultrasound-heating events throughout all lateral-locations of the second skin-portion.

The second stage 214 may include an earlier second-stage temporal interval followed, after a delay of at least 10 seconds, by a later second-stage temporal interval. For example, the first transducer assembly 300A together with contact-cooling from the applicator produces in the first skin-portion, first and second (36–° C., 45+° C., 8 seconds, 60 seconds) ultrasound-heating events which occur, respectively, during the earlier second-stage temporal interval of the second stage 214; and the later second-stage temporal interval of the second stage 214. Alternatively or additionally, the second transducer assembly 300B together with contact-cooling from the applicator produces in the second skin-portion, first and second (36–° C., 45+° C., 8 seconds, 60 seconds) ultrasound-heating events which respectively occur during (i) the earlier second-stage temporal interval of the second stage 214; and (ii) the later second-stage temporal interval of the second stage 214.

In any of the previously described embodiments, the applicator may include a third ultrasound assembly 300C having a forward-facing transceiving surface 310, where during the entirety of the tissue-engaged time-period a third skin-portion (e.g., 160CX and/or 160CY in FIG. 7B) continuously faces this surface 310 and remains in continuous contact therewith. An upper surface of the third skin-portion may be of the same area and the same shape as upper surfaces of both of the first and second skin-portions (e.g. an area of all of the first, second and third skin-portions may be at least 2 cm² or at least 3 cm² or at least 4 cm² or at least 5 cm² or at least 6 cm² or at least 7 cm² or at last 8 cm² or at least 10 cm²). The applicator 102 may include three inner walls 424A, 424B, 424C which all face to the mediating region respectively in first, second and third directions, where the first 424A and second 424B inner walls face each other, and the third direction is perpendicular to both of the first and second directions, and where the first, the second and the third forward-facing surfaces 310 are respectively part of the first 424A, the second 424B and the third 424C inner walls. The third skin-region may remain in contact with the respective forward facing-surface 310 of the third ultrasound assembly 300C throughout an entirety of the tissue-engaged time-period (e.g., the contact cooling is provided by the third wall 424C).

In any of the above examples, during the first stage time-period 615, the third ultrasound assembly 300C may not irradiate the biological tissue with ultrasound or a total energy of ultrasound transmitted by the third ultrasound assembly 300C to the biological tissue may be at most 20% (or at 10% or at most 5%) of that transmitted by the first ultrasound assembly 300A or of that transmitted by the second ultrasound assembly 300B. In some examples, during the second stage 214, the third transducer assembly 300C may deliver ultrasound to the mediating region via forward-facing surface 310 and contact-cooling be applied by the applicator 102 (e.g. by surface 310) to the tissue such that the third 300C transducer assembly together with contact-cooling from the applicator 102 produces one or more (36–° C., 45+° C., 8 seconds, 60 seconds) ultrasound-heating events in the third skin-portion. In some examples, during the second stage 214 the first transducer assembly 300A together with contact-cooling from the applicator produces one or more (36–° C., 45+° C., 8 seconds, 60 seconds) ultrasound-heating events in throughout all lateral-locations of the third skin-portion.

In some examples, the second stage 214 includes an earlier second-stage temporal interval followed, after a delay of at least 10 seconds, by a later second-stage temporal interval. For example, the third transducer assembly 300C together with contact-cooling from the applicator produces in the third skin-portion, first and second (36–° C., 45+° C., 8 seconds, 60 seconds) ultrasound-heating events which occur respectively during the earlier second-stage temporal interval of the second stage 214 and the later second-stage temporal interval of the second stage 214. The third transducer assembly 300C together with contact-cooling from the applicator may produce throughout the third skin-portion, first and second (36–° C., 45+° C., 8 seconds, 60 seconds) ultrasound-heating events which occur respectively during the earlier second-stage temporal interval of the second stage 214 and the later second-stage temporal interval of the second stage 214.

In any of the previously described embodiments, vacuum and/or negative pressure (e.g. applied directly to the third skin-portion) may be configured to urge the third skin-portion to the wall 424C and/or to the forward-facing surface 310 for an entirety of the tissue-engaged time-period.

In any of the previously described embodiments, all of the first and second and third skin-portions may be maintained flat during the entirety of the tissue-engaged time-period. Duration of the skin-engaged time period may be at least 10 minutes or at least 15 minutes or at least 20 minutes.

In any of the previously described embodiments, the treatment can be performed without causing necrosis to the mediating subdermal tissue 150 and/or performed without causing necrosis to the biological tissue.

In any of the previously described embodiments, the continuous contact between the first and/or second and/or third skin portion and the respective forward-facing surface(s) 310 of the respective transducer assembly(ies) 300A may be static so that throughout the tissue-engaged time-period there is no relative motion between the first skin portion and the respective forward-facing surface 310.

In any of the previously described embodiments, the forward-facing transceiving surface 310 of any of the transducer assemblies may be a surface of an intermediate object (e.g. plate) constructed of metal (e.g. aluminum or copper or a suitable plastic). Such surface(s) of the plate (an aluminum plate) may be of a thickness of at least 1 mm. The forward-facing surface(s) may be surface(s) of plate(s) each having a Q factor between 30 and 70 (e.g. between 30 and 40 or between 40 and 50 or between 50 and 60 or between 60 and 70).

In any of the previously described embodiments, wherein the second stage 214 may conclude no later than 45 minutes or no later than 30 minutes or no later than 20 minutes or no later than 10 minutes or no later than 5 minutes or no later than 3 minutes after the conclusion of the first stage time period 615.

In any of the previously described embodiments, an aspect-ratio of each of the first and second and third skin-portions may be between 0.3 and 3.

In any of the previously described embodiments, each of the first and second and third skin-portions may be rectangular in shape.

In any of the previously described embodiments, during the tissue-engaged time-period (e.g. during the first-stage time period 615), one or more ultrasound time-of-flight measurements is performed between the first 300A and second 300B ultrasound transducer-assemblies, and wherein one of operating parameters of the first 300A and/or second 300B ultrasound transducer-assemblies is subsequently modified in accordance with the results of one or more of the ultrasound time-of-flight measurements. For example, at least one of the operating parameters that is modified includes one or more of a power-level, a duty cycle (e.g. for delivery of CW unfocused ultrasound), and an ultrasound frequency. The one or more operating parameters may be subsequently modified to target uniform heating within the first-stage fraction Stage1_fact_Med_tiss of the mediating subdermal tissue.

In any of the previously described embodiments, negative pressure and/or vacuum may be applied to the tissue during at least some or at least most or at least all of the tissue-engaged time-period so as to urge any one of skin-portions or all of the skin portions towards the respective forward-facing surface 310.

In any of the previously described embodiments, during the tissue-engaged time-period (e.g. during the first-stage time period 615), one or more ultrasound time-of-flight measurements is performed (e.g. between the first 300A and second 300B ultrasound transducer-assemblies), and intensity of vacuum or negative pressure is regulated according to the results of the ultrasound time-of-flight measurement (e.g. in response to longer time-of-flight, an intensity of vacuum or negative pressure is increased and/or in response to shorter time-of-flight, an intensity of vacuum or negative pressure is decreased).

In some embodiments, the treatment process proceeds as follows: During a time-period when a volume of biological tissue is disposed in a region between the first and second transducer assemblies such that first and second portions of skin of the tissue face away from each other and face respectively to the first and second transducer assemblies, the volume of biological tissue is heated by operating both of the first and second transducer assemblies to emit continuous wave (CW) non-focused ultrasound energy at frequency(ies) equal to or exceeding 1 MHz, and both the first and second portions of skin are subjected to surface-cooling. The biological tissue is subjected to both first and second temperature measurements during the time-window, where the first temperature measurement is a surface-temperature measurement by thermocouple or by detecting skin-reflected energy, and the second temperature measurement is a measurement of an average temperature of the biological tissue in the mediating region. The second temperature measurement is performed in accordance with a measured ultrasound time-of-flight across the mediating region between the transducer assemblies. Strength of the surface cooling is controlled in accordance with results of the surface-temperature measurement, and power-level of the CW non-focused ultrasound energy from the first and/or second ultrasound transducer assemblies is regulated in accordance with results of the average-temperature measurement of the biological tissue in the mediating region.

The biological tissue in the mediating region may substantially span entirety of a mediating region between the transducer assemblies. 105. For example, one or more transducers of the first transducer assembly may be in direct contact with first mediating object that is in direct contact with the first portion of skin. and one or more transducers of the second transducer assembly are in direct contact with second mediating object that is in direct contact with the first portion of skin. The first and/or second mediating object may be a plate or a stack of plates.

In any of the previously described embodiments of the treatment technique, the surface-temperature measurement may include a temperature measurement of the first portion of skin, and a strength of the surface cooling at the first portion of skin may be controlled in accordance with a combination of the results of the temperature measurement of the first portion of skin, and a maximum permitted skin temperature $T_{SKIN}^{MAX\text{-}PERMITTED}$ which does not exceed 25 degrees Celsius.

In any of the previously described embodiments of the treatment technique, —the surface-temperature measurement may include a temperature measurement of the second portion of skin, and a strength of the surface cooling at the second portion of skin may be controlled in accordance with a combination of the results of the temperature measurement of the second portion of skin, and the maximum permitted skin temperature $T_{SKIN}^{MAX\text{-}PERMITTED}$.

In any of the previously described embodiments of the treatment technique, —a power-level of the CW non-focused ultrasound energy from the first and/or second ultrasound transducer assemblies may be regulated, in accordance with a combination of the results of the average-temperature measurement of the biological tissue in the mediating region, and a minimum required average-temperature for biological tissue of the medicating region $T_{MEDIATING\text{-}REGION}^{MIN\text{-}REQUIRED\text{-}AVG}$, and a value of the minimum required average-temperature for biological tissue of the medicating region $T_{MEDIATING\text{-}REGION}^{MIN\text{-}REQUIRED\text{-}AVG}$ may be at least 40 degrees Celsius.

The invention claimed is:

1. A medical device for applying heat-based tissue treatment to an individual's body part, the device comprising an applicator carrying a transducer arrangement configured and controllably operable to perform a treatment session on at least one region of interest in tissue to achieve a desired treatment effect at each of said at least one region of interest; wherein:

the applicator is configured to define a substantially U-shaped surface presenting a U-shaped interface region for attachment with the body part along said U-shaped surface such that each of the at least one region of interest is located between opposite arms of said U-shaped interface region, thereby enabling attachment of tissue being treated in a cavity defined by the U-shaped interface region;

the transducer arrangement is configured and controllably operable to perform a treatment session on each of said at least one region of interest by delivering unfocused directional radiation comprising heating radiation towards each of said at least one region of interest;

the transducer arrangement comprises first and second opposing ultrasound transducer-assemblies defining, respectively, first and second opposing ultrasound-transceiving surfaces located at the opposite arms of the U-shaped interface region, such that each of the first and second ultrasound transducer assemblies has respective forward-facing transceiving surface by which it faces the other opposing transceiving surface via the region between the opposite arms of the U-shaped interface region of the applicator;

said first and second ultrasound transducer-assemblies are configured operable to generate the first and second ultrasound radiations of respectively first and second different frequencies selected to avoid creation of or significantly reduce a standing wave effect and provide homogeneous temperature along the region of interest during the treatment session; and the first and second ultrasound transducer-assemblies are configured to transmit the unfocused directional ultrasound radiation in opposite directions, such that the unfocused directional ultrasound radiation propagates from one of said ultrasound-transceiving surfaces to the other opposing ultrasound-transceiving surface and is detected at the other opposing ultrasound-transceiving surface, providing that measured data corresponding to the detected ultrasound radiation is indicative of time-of-flight data of the ultrasound radiation between the first and second opposing ultrasound-transceiving surfaces and therefore indicative of a temperature of the region of interest between said first and second opposing ultrasound-transceiving surfaces and indicative of attachment of the tissue to the interface region, said transducer arrangement being thereby configured and controllably operable to perform the treatment session on each of said at least one region of interest, and configured and controllably operable to perform a control session comprising control of the temperature and attachment during the treatment session based on said measured data.

2. The medical device according to claim 1, wherein said first and second opposing ultrasound transducer-assemblies are configured and operable to generate said heating radiation, said first and second ultrasound transducer-assemblies being configured to generate directional first and second ultrasound heating radiations propagating in the opposite directions along the substantially coinciding first and second axes towards each of the at least one region of interest in the tissue being engaged between said opposite arms of the interface region.

3. The medical device according to claim 1, further comprising at least one of the following:

a cooling assembly configured and controllably operable to perform cooling of the interface region during the treatment session;

a control unit configured and operable to control operation of said applicator to maintain predetermined temperature pattern in the tissue during the treatment session;

a temperature control circuitry for monitoring temperature of said at least one region of interest; and an attachment control circuitry configured and operable to monitor acoustic contact between the tissue and at least a part of said interface region and control operation of the transducer arrangement accordingly.

4. The medical device according to claim 3, comprising the temperature control circuitry and the attachment control circuitry, wherein:

said temperature control circuitry is responsive to said measured data indicative of the detected ultrasound radiation from the tissue to extract from said measured data at least one of an average temperature of the region of interest at respective location in the tissue; and said attachment control circuitry is responsive to said measured data indicative of the detected ultrasound radiation from the tissue and at least a part of said interface region to control operation of the transducer arrangement accordingly.

5. The medical device according to claim 4, wherein said applicator further comprises at least one temperature sensor located in vicinity of the interface region and configured and operable to provide sensing data indicative of temperature of surface tissue regions.

6. The medical device according to claim 3, comprising the cooling assembly configured and controllably operable to perform cooling of the interface region during the treatment session and the temperature control circuitry for monitoring temperature of said at least one region of interest, the device being characterized by at least one of the following:

said temperature control circuitry is responsive to measured data indicative of an operative electric current of the cooling assembly required to cool the interface region to provide a predetermined temperature of tissue surface at the interface region to apply, based on said measured data, model-based processing utilizing thermal properties of a biological tissue under treatment and determine an average temperature of said tissue;

said control unit is configured and operable to control the operation of said ultrasound transducer arrangement and said cooling assembly to provide maximum temperature of about 30 degrees Celsius at said interface region; and said control unit is configured and operable to control the operation of said ultrasound transducer arrangement and said cooling assembly to maintain temperature of the region of interest at deep location with respect to the region of interest to be at least 45 degrees Celsius during the treatment session.

7. The medical device according to claim 3, comprising a temperature control circuitry for monitoring temperature of said at least one region of interest, wherein:

said control unit is configured and operable to control the operation of said ultrasound transducer arrangement and said cooling assembly to maintain temperature of the region of interest at deep location with respect to the region of interest to be at least 45 degrees Celsius during the treatment session, the control unit being configured and operable to maintain said temperature of the region of interest to be in a range between 45 degrees Celsius and 55 degrees Celsius by modifying at least one operational parameter of said transducer arrangement, and said at least one parameter includes at least one of power-level and duty cycle of the ultrasound radiation.

8. The medical device according to claim 3, characterized by at least one of the following:

the cooling assembly comprises one or more Peltier cooling components;

a distance between the first and second substantially flat ultrasound-transceiving surfaces at the arms of the U-shaped interface region is in a range of 2-7 cm; and each of the first and second substantially flat ultrasound-transceiving surfaces has a surface area of at least 4 cm$^2$.

9. The medical device according to claim 1, having one of the following configurations:

(i)) said applicator is configured such that its surface comprising said interface region is flexible and foldable such that it is adapted to define said substantially U-shaped interface region; and (ii) a surface of said applicator comprising the U-shaped interface region is rigid.

10. The medical device according to claim 1, wherein the measured data is indicative of the time-of-flight data of said unfocused directional radiation being pulsed ultrasound radiation between the first and second transducer assemblies and thereby corresponds to the time-of-flight of ultrasound radiation through the tissue engaged between the opposite arms of said interface region, thereby enabling real time extraction from the time-of-flight data an average temperature of said region of interest being a deep region with respect to the interface region.

11. The medical device according to claim 10, configured and operable to carry out at least one of the following:

(a) utilize calibration data indicative of tissue temperature as a function of a change in the time-of-flight of the ultrasound radiation of a given frequency passing through a given biological tissue, to evaluate, from the measured time-of-flight data, data indicative of an average temperature of the region of interest in the tissue; and (b) utilize calibration data indicative of acoustic contact of the tissue and the interface region as a function of the time-of-flight of the ultrasound radiation of a given frequency passing through a given biological tissue, to evaluate, from the measured time-of-flight data, data indicative of the acoustic contact.

12. The medical device claim 1, having at least one of the following configurations:

the first and second transducer assemblies are configured and controllable to generate the first and second ultrasound radiations of respectively first and second frequencies with a difference between them in a range of 0.5%-20%;

said first and second opposing transducer assemblies comprise, respectively, first and second arrays of independently operable transceiver elements, the ultrasound-transceiving surface of each of said first and second transducer assemblies being defined by respective one of the first and second arrays of spaced-apart surface segments associated with the first and second arrays of the transceiver elements, thereby defining at least two opposing pairs of the ultrasound transceiver elements, each pair being formed by the first and second transceiver elements generating the first and second directional ultrasound radiations propagating along substantially coinciding axes in the opposite directions towards the region of interest in the tissue being engaged between said opposing sides of the interface region;

said transducer arrangement is configured and controllably operable with a time pattern of alternating tissue treatment intervals of the treatment session and intervals of the control session;

said transducer arrangement comprises an additional transducer assembly accommodated to transmit ultrasound radiation through a base portion of the U-shaped interface region;

said transducer arrangement is configured and operable with a pulsed mode during the control session;

the ultrasound transducer arrangement is capable of selectively operating in one of the following operational modes: a continuous wave operational mode of a predetermined duty cycle, and a pulsed operational mode; and said applicator further comprises first and second temperature sensors configured and operable to measure respective first and second temperatures in vicinity of said arms of the U-shaped interface region and provide corresponding sensing data being indicative of temperature of surface tissue regions.

13. The medical device according to claim 1, wherein the first and second transducer assemblies are configured and controllable to generate the first and second ultrasound radiations of respectively first and second frequencies with a difference between them in a range of 0.5%-20%, the first and second frequencies being selected to avoid creation of the standing wave effect and provide homogeneous temperature along the region of interest during the treatment session.

14. The medical device according to claim 1, wherein said first and second opposing transducer assemblies comprise, respectively, first and second arrays of independently operable transceiver elements, the ultrasound-transceiving surface of each of said first and second transducer assemblies being defined by respective one of the first and second arrays of spaced-apart surface segments associated with the first and second arrays of the transceiver elements, thereby defining at least two opposing pairs of the ultrasound transceiver elements, each pair being formed by the first and second transceiver elements generating the first and second directional ultrasound radiations propagating along substantially coinciding axes in the opposite directions towards the region of interest in the tissue being engaged between said opposing sides of the interface region, said transducer arrangement being configured and controllably operable to concurrently perform treatment sessions on at least two regions of interest being deep and shallow tissue regions with respect to their locations from the interface region.

15. The medical device according to claim 1, wherein said transducer arrangement is configured and controllably operable with a time pattern of alternating tissue treatment intervals of the treatment session and intervals of the control session, the device being characterized by at least one of the following:

the transducer arrangement is configured and controllably operable with a time pattern of alternating tissue treatment intervals of the treatment session and intervals of the control session implemented by, respectively, two different pairs of the opposing transceiver elements;

said control session comprises temperature control of the region of interest being treated based on the detection of the ultrasound radiation passed through the region of interest, enabling real time adjustment of one or more operational parameters of the treatment session;

the control session comprises control of acoustic contact between the interface region and the tissue surface engaged by said interface region, enabling real time adjustment of the treatment session; and said transducer arrangement is controllably operated with the continuous wave operational mode during said intervals of the treatment session and controllably operated with the pulsed mode during the intervals of the control session.

16. The medical device according to claim 15, wherein said transducer arrangement is controllably operated with the continuous wave operational mode during said intervals of the treatment session and controllably operated with the pulsed mode during the intervals of the control session, the device being characterized by at least one of the following:

operational frequency of the ultrasound radiation during the treatment session is in a range of 1 MHz-4 Hz; and said region of interest being treated is a deep region with respect to the interface region.

17. The medical device according to claim 1, wherein said transducer arrangement comprises an additional transducer assembly accommodated to transmit ultrasound radiation through a base portion of the U-shaped interface region, said region of interest being a shallow region with respect to the interface region.

18. The medical device according to claim 1, wherein said transducer arrangement is configured and operable with a pulsed mode during the control session, said region of interest being a shallow region with respect to the interface region.

19. The medical device according to claim 1, wherein:

said transducer arrangement is characterized by one of the following:

said transducer arrangement comprises an additional transducer assembly accommodated to transmit ultrasound radiation through a base portion of the U-shaped interface region; and

said transducer arrangement is configured and operable with a pulsed mode during the control session;

said region of interest is a shallow region with respect to the interface region; and operational frequency of the ultrasound radiation during the treatment session is in a range of 4.5 MHz.

20. The medical device according to claim 1, wherein said interface region of the applicator has at least one of the following configurations:

said interface region of the applicator has a distal side of a substantially flat surface for contacting tissue being treated and an opposite proximate side carrying one or more elements of the transducer arrangement and one or more elements of the cooling assembly; and said interface region of the applicator is made of a heat conducting material and is configured to provide substantial impedance matching with impedance of the transducer arrangement, such that the ultrasound radiation passage through said interface region has energy losses not exceeding 10%.

21. The medical device according to claim 1, comprising:

an attachment control circuitry configured and operable to monitor acoustic contact between the tissue and at least a part of said interface region and control operation of the transducer arrangement accordingly; and a tissue attachment mechanism configured and controllably operable by said attachment control circuitry to provide a desired acoustic contact between said at least part of the interface region and the tissue under treatment.

22. The medical device according to claim 21, characterized by at least one of the following:

said tissue attachment mechanism comprises a source of negative pressure for urging the tissue towards the interface region of the applicator; and said attachment control circuitry is configured and operable to selectively increase or decrease a strength of the negative pressure upon identifying, respectively, decrease or increase in a prevailing average temperature of surface of the tissue under treatment.

23. The medical device according to claim 22, wherein said attachment control circuitry is configured and operable to increase a strength of the negative pressure upon identifying, from said measured data, an increase in a prevailing average time-of-flight of the detected ultrasound radiation.

* * * * *